United States Patent
Haq et al.

(10) Patent No.: US 9,937,161 B2
(45) Date of Patent: Apr. 10, 2018

(54) COMBINATORIAL COMPOSITIONS AND METHODS FOR TREATMENT OF MELANOMA

(71) Applicants: THE GENERAL HOSPITAL CORPORATION, Boston, MA (US); THE BRIGHAM AND WOMEN'S HOSPITAL, INC., Boston, MA (US)

(72) Inventors: Rizwan Haq, Boston, MA (US); David E. Fisher, Newton, MA (US); Hans Ragnar Widlund, Brookline, MA (US)

(73) Assignees: THE GENERAL HOSPITAL CORPORATION, Boston, MA (US); THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 14/770,994

(22) PCT Filed: Mar. 6, 2014

(86) PCT No.: PCT/US2014/021019
§ 371 (c)(1),
(2) Date: Aug. 27, 2015

(87) PCT Pub. No.: WO2014/138338
PCT Pub. Date: Sep. 12, 2014

(65) Prior Publication Data
US 2016/0008332 A1    Jan. 14, 2016

Related U.S. Application Data

(60) Provisional application No. 61/773,374, filed on Mar. 6, 2013, provisional application No. 61/881,098, filed on Sep. 23, 2013.

(51) Int. Cl.
| | |
|---|---|
| *A61K 31/06* | (2006.01) |
| *A61K 31/437* | (2006.01) |
| *A61K 31/44* | (2006.01) |
| *A61K 45/06* | (2006.01) |
| *A61K 31/352* | (2006.01) |
| *A61K 31/506* | (2006.01) |
| *A61K 31/65* | (2006.01) |
| *G01N 33/574* | (2006.01) |
| *C12Q 1/68* | (2018.01) |

(52) U.S. Cl.
CPC ............ *A61K 31/437* (2013.01); *A61K 31/06* (2013.01); *A61K 31/352* (2013.01); *A61K 31/44* (2013.01); *A61K 31/506* (2013.01); *A61K 31/65* (2013.01); *A61K 45/06* (2013.01); *C12Q 1/6886* (2013.01); *G01N 33/5743* (2013.01); *C12Q 2600/158* (2013.01)

(58) Field of Classification Search
CPC ... A61K 31/437; A61K 31/06; A61K 2300/00
See application file for complete search history.

(56) References Cited

U.S. PATENT DOCUMENTS

| | | | |
|---|---|---|---|
| 6,811,788 B2* | 11/2004 | Yu ...................... | A61K 31/4164 424/278.1 |
| 7,285,541 B2 | 10/2007 | Gleave et al. | |
| 2009/0098569 A1 | 4/2009 | Spiegelman et al. | |
| 2011/0177154 A1 | 7/2011 | Bangera et al. | |
| 2012/0329761 A1 | 12/2012 | Schimmer et al. | |
| 2013/0078252 A1* | 3/2013 | Wilson ................ | A61K 31/437 424/138.1 |

FOREIGN PATENT DOCUMENTS

| | | |
|---|---|---|
| WO | 2011/097594 A2 | 8/2011 |
| WO | 2012/159085 A2 | 11/2012 |

OTHER PUBLICATIONS

Vasquez e al. Cancer Cell, Published Feb. 2013, vol. 23, No. 3, pp. 287-301.*
Ascierto, P.A. et al., Lancet Oncol. 14(3):249-256 (Mar. 2013). doi: 10.1016/S1470-2045(13)70024-X. Epub Feb. 13, 2013. "MEK162 for patients with advanced melanoma harbouring NRAS or Val600 BRAF mutations: a non-randomised, open-label phase 2 study."
Board R.E., Br J Cancer.101(10):1724-1730 Nov. 17, 2009. Nov. doi: 10.1038/sj.bjc.6605371. Epub Oct. 27, 2009. "Detection of BRAF mutations in the tumour and serum of patients enrolled in the AZD6244 (ARRY-142886) advanced melanoma phase II study."
Bogunovic, D. et al., Proc Natl Acad Sci U S A.106(48):20429-20434, Dec. 1, 2009. doi: 10.1073/pnas.0905139106. Epub Nov. 13, 2009. "Immune profile and mitotic index of metastatic melanoma lesions enhance clinical staging in predicting patient survival."
Bollag, G. et al. Nature. 467(7315):596-599 Sep. 30, 2010. doi: 10.1038/nature09454. "Clinical efficacy of a RAF inhibitor needs broad target blockade in BRAF-mutant melanoma."
Boni, A. et al., Cancer Res.70(13):5213-5219 Jul. 1, 2010. doi: 10.1158/0008-5472.CAN-10-0118. Epub Jun. 15, 2010. "Selective BRAFV600E inhibition enhances T-cell recognition of melanoma without affecting lymphocyte function."
Bonnet, S. et al., Cancer Cell.11(1):37-51, Jan. 2007. "A mitochondria-K+ channel axis is suppressed in cancer and its normalization promotes apoptosis and inhibits cancer growth."
Garraway, L.A. et al., Nature. Garraway, L.A. et al., 436(7047):117-122 Jul. 7, 2005. "Integrative genomic analyses identify MITF as a lineage survival oncogene amplified in malignant melanoma."

(Continued)

*Primary Examiner* — Samira Jean-Louis
(74) *Attorney, Agent, or Firm* — Nixon Peabody LLP; David S. Resnick

(57) ABSTRACT

Embodiments described here are combinatorial compositions and methods using these compositions for treating melanomas having activated mutations. The compositions comprises combinations of inhibitors of a MAPK pathway, ERK inhibitors, EGFR inhibitors, oxidative phosphorylation (OXPHOS) inhibitors, inhibitors of B-Raf, mitochondrial inhibitors, c-KIT inhibitors, MEK inhibitors and tigecycline or a derivative thereof.

5 Claims, 38 Drawing Sheets

(56) References Cited

OTHER PUBLICATIONS

Gibney, G.T. et al., Lancet Oncol.14(3):186-188 (Mar. 2013). doi: 10.1016/S1470-2045(13)70054-8. Epub Feb. 13, 2013. "Expanding targeted therapy to NRAS-mutated melanoma."

Greger, J.G. et al., Mol Cancer Ther.11(4):909-920 (Apr. 2012). doi: 10.1158/1535-7163.MCT-11-0989. Epub Mar. 2, 2012. "Combinations of BRAF, MEK, and PI3K/mTOR inhibitors overcome acquired resistance to the BRAF inhibitor GSK2118436 dabrafenib, mediated by NRAS or MEK mutations."

Joseph, E.W. et al., Proc Natl Acad Sci U S A. 107(33):14903-14908 Aug. 17, 2010. doi: 10.1073/pnas.1008990107. Epub Jul. 28, 2010. "The RAF inhibitor PLX4032 inhibits ERK signaling and tumor cell proliferation in a V600E BRAF-selective manner."

Tsai, J. et al., Proc Natl Acad Sci U S A. 105(8):3041-3046 Feb. 26, 2008. doi: 10.1073/pnas.0711741105. Epub Feb. 19, 2008. "Discovery of a selective inhibitor of oncogenic B-Raf kinase with potent antimelanoma activity."

Uldry, M. et al., Cell Metab. 3(5):333-341 May 2006. "Complementary action of the PGC-1 coactivators in mitochondrial biogenesis and brown fat differentiation."

Wellbrock, C. et al.,J Cell Biol.170(5):703-708 Aug. 29, 2005. "Elevated expression of MITF counteracts B-RAF-stimulated melanocyte and melanoma cell proliferation."

Wellbrock, C. et al.,J Cell Biol.170(5):703-708 Aug. 29, 2005. "Elevated expression of MITF counteracts B-RAF-stimulated melanocyte and melanoma cell proliferation."

\* cited by examiner

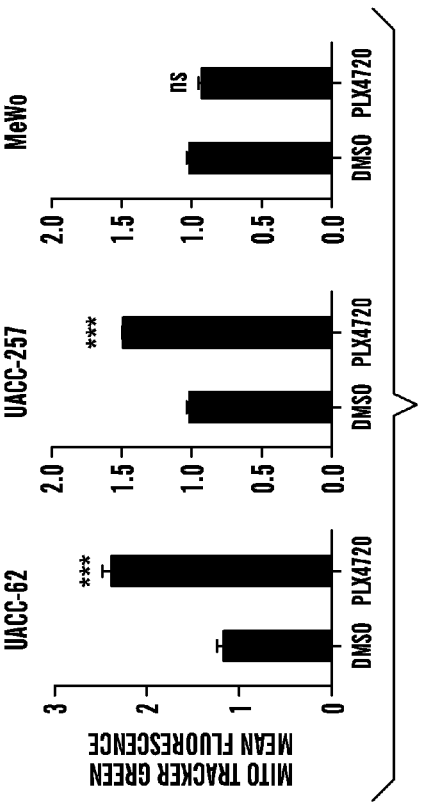
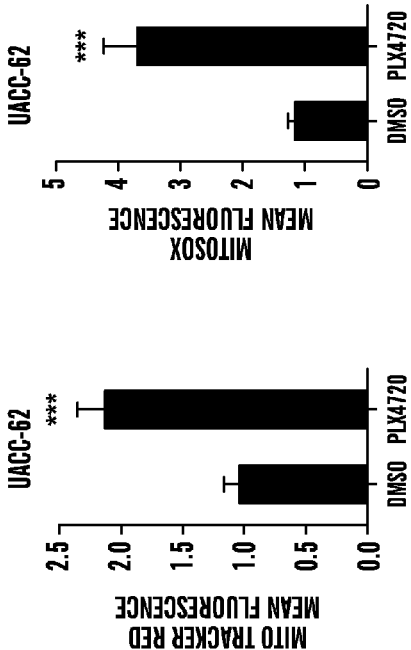
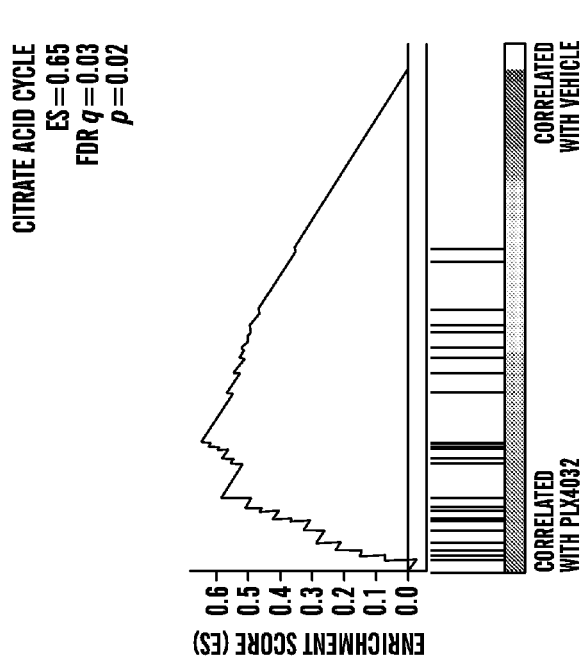
FIG. 1A  FIG. 1B  FIG. 1C  FIG. 1D

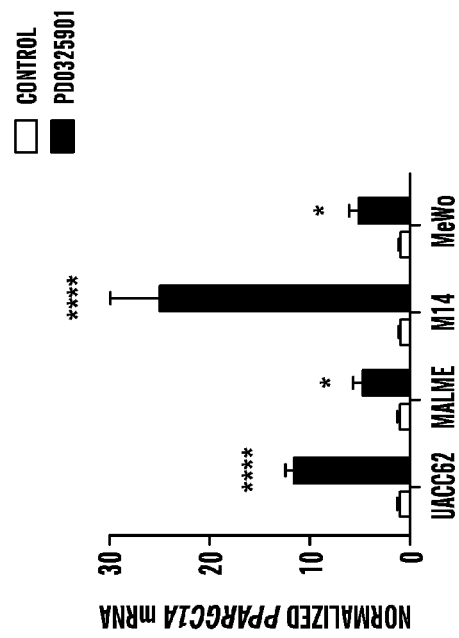
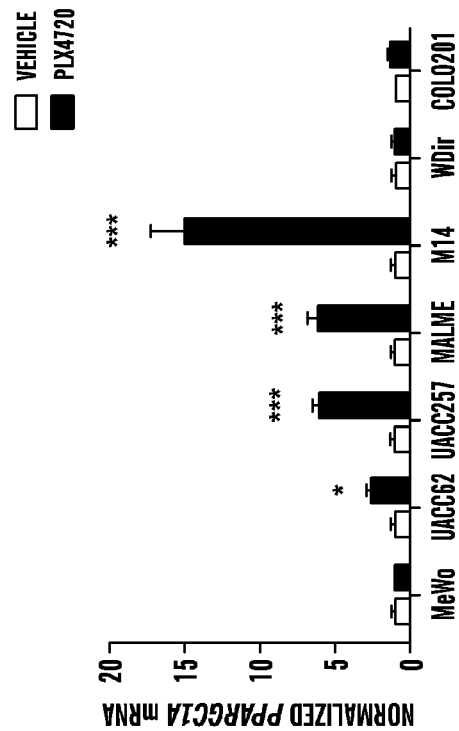
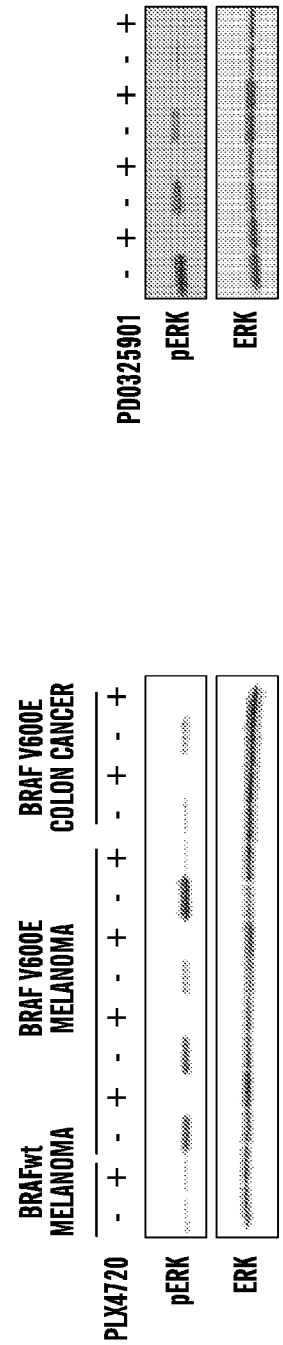
FIG. 2A
FIG. 2B
FIG. 2C
FIG. 2D

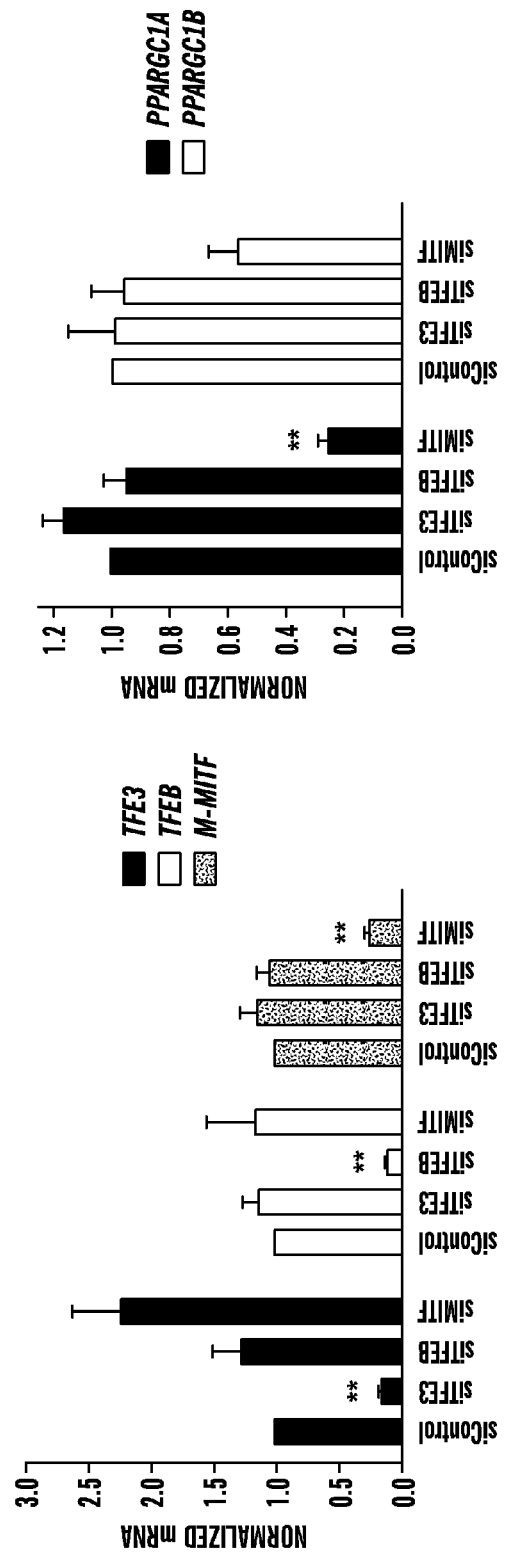

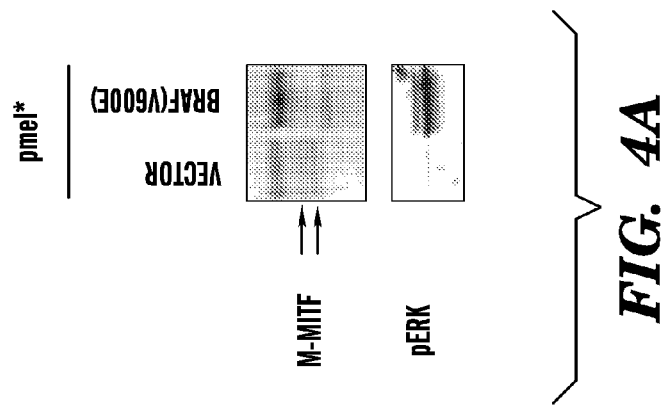
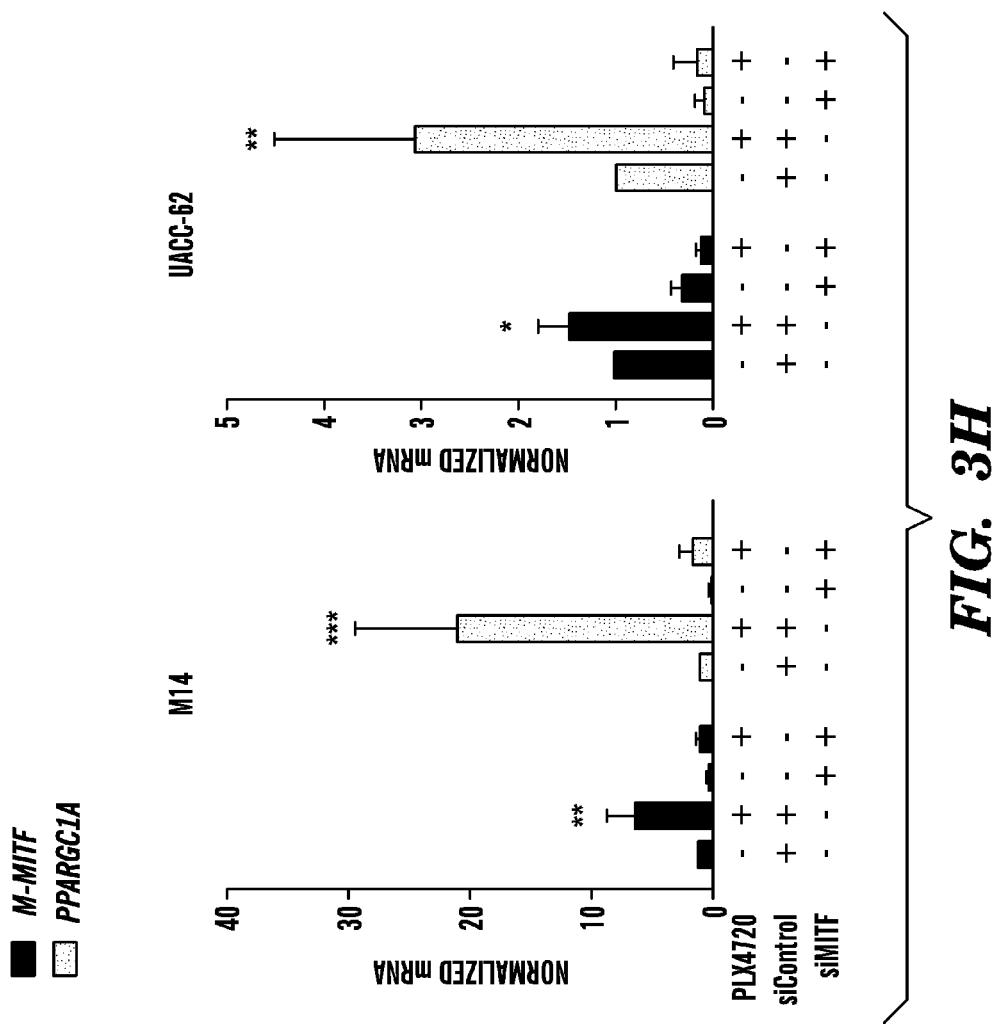

FIG. 12A

| | Gene | Description | | |
|---|---|---|---|---|
| OXIDATIVE PHOSPHORYLATION | ATP5B | ATP SYNTHASE, H+TRANSPORTING, MITOCHONDRIAL F1 COMPLEX, BETA POLYPEPTIDE | -1.515 | NA |
| | ATP5D | ATP SYNTHASE, H+TRANSPORTING, MITOCHONDRIAL F1 COMPLEX, DELTA SUBUNIT | -1.343 | NA |
| | ATP5G1 | ATP SYNTHASE, H+TRANSPORTING, MITOCHONDRIAL F0 COMPLEX, SUBUNIT C1 (SUBUNIT 9) | -1.323 | NA |
| | COX15 | COX15 HOMOLOG, CYTOCHROME C OXIDASE ASSEMBLY PROTEIN (YEAST) | -1.504 | NA |
| | CYC1 | CYTOCHROME c-1 | -1.308 | NA |
| | NDUFA8 | NADH DEHYDROGENASE (UBIQUINONE) 1 ALPHA SUBCOMPLEX, 8, 19kDa | -1.420 | NA |
| | NDUFA9 | NADH DEHYDROGENASE (UBIQUINONE) 1 ALPHA SUBCOMPLEX, 9, 39kDa | -1.297 | -117 |
| | NDUFB10 | NADH DEHYDROGENASE (UBIQUINONE) 1 BETA SUBCOMPLEX, 10, 22kDa | -1.369 | NA |
| | NDUFC2 | NADH DEHYDROGENASE (UBIQUINONE) 1, SUBCOMPLEX UNKNOWN, 2, 14.5kDa | -1.371 | NA |
| | NDUFS3 | NADH DEHYDROGENASE (UBIQUINONE) Fe-S PROTEIN 3, 30kDa (NADH-COENZYME Q REDUCTASE) | -1.367 | NA |
| | NDUFS7 | NADH DEHYDROGENASE (UBIQUINONE) Fe-S PROTEIN 7, 20kDa (NADH-COENZYME Q REDUCTASE) | -1.495 | NA |
| | PPA2 | PYROPHOSPHATASE (INORGANIC) 2 | -1.313 | NA |
| | SDHB | SUCCINATE DEHYDROGENASE COMPLEX, SUBUNIT B, IRON SULFUR (Ip) | -1.555 | 308 |
| | UQCRC1 | UBIQUINOL-CYTOCHROME C REDUCTASE CORE PROTEIN I | -1.385 | NA |
| | PPARGC1A | PEROXISOME PROLIFERATOR-ACTIVATED RECEPTOR GAMMA COACTIVATOR 1-alpha (PGC-1alpha) | -1.62 | -101 |
| | PPARGC1B | PEROXISOME PROLIFERATOR-ACTIVATED RECEPTOR GAMMA COACTIVATOR 1-beta (PGC-1beta) | -1.34 | NA |
| OXIDATIVE STRESS | SOD2 | SUPEROXIDE DISMUTASE 2, MITOCHONDRIAL | -1.64 | NA |
| | CAT | CATALASE | -1.71 | NA |

*FIG. 12F*

COMBINATORIAL COMPOSITIONS AND METHODS FOR TREATMENT OF MELANOMA

CROSS REFERENCE TO RELATED APPLICATIONS

This application is a 35 U.S.C. 371 National Stage Application of International Application No. PCT/US14/21019 filed on Mar. 6, 2014, which designates the United States, and which claims benefit under 35 U.S.C. § 119(e) of U.S. Provisional Application Ser. No. 773,374 filed on Mar. 6, 2013 and U.S. Provisional Application Ser. No. 61/881,098 filed on Sep. 23, 2013, the contents of each of which are incorporated herein by reference in their entireties.

GOVERNMENT SUPPORT

This invention was made with Government support under Grant No. R01 AR043369-16 awarded by the National Institutes of Health, and Grant Nos. R01CA163336 and P50CA093683 awarded by the National Cancer Institute. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Aug. 10, 2015, is named 030258-076723-US_SL and is 13,617 bytes in size.

FIELD OF THE INVENTION

This invention relates to compositions and the uses thereof for treatment of melanoma.

BACKGROUND OF THE INVENTION

Melanoma is a malignant tumor of melanocytes, and can originate in any part of the body that contains melanocytes. There are 160,000 new cases diagnosed each year, and about 48,000 melanoma related deaths reported each year. Melanoma is the most incurable cancer once the cancer cells have metastasize to distant part of the body. Therefore, metastatic melanomas have to be aggressively treated with current and newer therapies.

A good number of mutations have been found in melanoma. For examples, mutations in BRAF and NRAS genes have found in melanomas, and these mutations have been known to activate downstream MEK-ERK oncogenic signal transduction pathway, or MAPK pathway. The MAPK pathway is an important signaling cascade driving cell proliferation, differentiation, and survival and could have an important role in the pathogenesis of melanoma. An improved understanding of the role of genetic mutations in melanoma could result in advancements in treatments of melanoma and cancers, and a targeted therapy directed towards the specific mutations and/or MAPK pathway signaling could provide an effective treatment against tumor growth for patients.

SUMMARY OF THE INVENTION

It is the objective of this invention to provide an effective combination composition and therapy for melanoma. This is useful for metastatic melanomas. This is also useful for melanomas that have a high risk of recurrences, for example, when the lymph node of a patient test positive for the melanoma, meaning that at least the primary melanoma has spread to the nearby lymph nodes but there is no other evidence of the melanoma elsewhere besides the primary melanoma. This is also useful for melanomas that have become resistant to conventional therapies or melanomas that are susceptible to developing resistance to conventional therapies for melanoma.

It is the objective of this invention to provide an effective therapy for melanoma in general. The therapy can be useful for melanomas having at least one mutation in a gene, and the mutation is an activating mutation that activates directly or indirectly the MAPK pathway. For examples, a mutation in B-Raf (a proto-oncogene serine/threonine-protein kinase), in c-KIT (a proto-oncogene tyrosine protein kinase), a NF1 (neurofibromin 1 or neurofibromatosis-related protein), a NRAS (neuroblastoma RAS viral (v-ras) oncogene protein) or combinations of mutations therefrom.

It is also the objective of this invention to provide to a method of early monitoring or detection of the development of drug resistance in a melanoma to conventional therapies and treating the resistant melanoma. The melanoma becoming resistant to conventional therapies can be a melanoma having at least one mutation in a gene, and the mutation is an activating mutation that activates directly or indirectly the MAPK pathway. For examples, a B-Raf mutation, a c-KIT, a NRAS mutation, a NF1 mutation or combinations therefrom.

Accordingly, provided herein is a pharmaceutical composition for treating melanoma in a subject in need thereof, the composition comprising at least one inhibitor of a MAPK pathway and at least one mitochondrial inhibitor in a pharmaceutically acceptable carrier.

In one embodiment, provided herein is a composition comprising at least one inhibitor of a MAPK pathway and at least one mitochondrial inhibitor for the manufacture of medicament for treating melanoma in a subject in need thereof.

In one embodiment, provided herein is a composition comprising at least one inhibitor of a MAPK pathway and at least one mitochondrial inhibitor for use in treating melanoma in a subject in need thereof.

In one embodiment of any one of the composition described, the at least one inhibitor of a MAPK pathway is an inhibitor of B-Raf, an inhibitor of c-KIT, an inhibitor of MEK 1 or MEK2 or both, or an inhibitor of ERK.

In one embodiment of any one of the composition described, the at least one inhibitor of a MAPK pathway is an epidermal growth factor receptor (EGFR) inhibitor.

In one embodiment of any one of the composition described, the at least one inhibitor of a MAPK pathway is a platelet-derived growth factor receptor (PDGFR) inhibitor.

In one embodiment of any one of the composition described, the at least one mitochondrial inhibitor is an inhibitor of oxidative phosphorylation.

In one embodiment, provided herein is a pharmaceutical composition for treating melanoma in a subject in need thereof, the composition comprising at least one inhibitor of B-Raf and at least one mitochondrial inhibitor in a pharmaceutically acceptable carrier.

In one embodiment, provided herein is a composition comprising at least one inhibitor of B-Raf and at least one mitochondrial inhibitor for the manufacture of medicament for treating melanoma in a subject in need thereof.

In one embodiment, provided herein is a composition comprising (a) tigecycline or a derivative thereof; and (b) at least one inhibitor of B-Raf and/or at least one mitochondrial inhibitor for the manufacture of medicament for treating melanoma in a subject in need thereof.

In one embodiment, provided herein is a composition comprising at least one inhibitor of B-Raf and at least one mitochondrial inhibitor for use in treating melanoma in a subject in need thereof.

In one embodiment, provided herein is a composition comprising (a) tigecycline or a derivative thereof and (b) at least one inhibitor of B-Raf and/or at least one mitochondrial inhibitor for use in treating melanoma in a subject in need thereof.

In one embodiment, provided herein is a pharmaceutical composition for treating melanoma in a subject in need thereof, the composition comprising at least one inhibitor of c-KIT and at least one mitochondrial inhibitor in a pharmaceutically acceptable carrier.

In one embodiment, provided herein is a composition comprising at least one inhibitor of c-KIT and at least one mitochondrial inhibitor for the manufacture of medicament for treating melanoma in a subject in need thereof.

In one embodiment, provided herein is a composition comprising at least one inhibitor of c-KIT and at least one mitochondrial inhibitor for use in treating melanoma in a subject in need thereof.

In one embodiment, provided herein is a pharmaceutical composition for treating melanoma in a subject in need thereof, the composition comprising at least one inhibitor of MEK1 and at least one mitochondrial inhibitor in a pharmaceutically acceptable carrier.

In one embodiment, provided herein is a pharmaceutical composition for treating melanoma in a subject in need thereof, the composition comprising at least one inhibitor of MEK 2 and at least one mitochondrial inhibitor in a pharmaceutically acceptable carrier.

In one embodiment, provided herein is a pharmaceutical composition for treating melanoma in a subject in need thereof, the composition comprising at least one inhibitor of MEK1 and MEK2, and at least one mitochondrial inhibitor in a pharmaceutically acceptable carrier.

In one embodiment, provided herein is a composition comprising at least one inhibitor of MEK1, MEK2 or both MEK1 and MEK 2, and at least one mitochondrial inhibitor for the manufacture of medicament for treating melanoma in a subject in need thereof.

In one embodiment, provided herein is a composition comprising at least one inhibitor of MEK1, MEK2 or both MEK1 and MEK 2, and at least one mitochondrial inhibitor for use in treating melanoma in a subject in need thereof.

In one embodiment, provided herein is a pharmaceutical composition for treating melanoma in a subject in need thereof, the composition comprising at least one inhibitor of ERK and at least one mitochondrial inhibitor in a pharmaceutically acceptable carrier.

In one embodiment, provided herein is a composition comprising at least one inhibitor of ERK and at least one mitochondrial inhibitor for the manufacture of medicament for treating melanoma in a subject in need thereof.

In one embodiment, provided herein is a composition comprising at least one inhibitor of ERK and at least one mitochondrial inhibitor for use in treating melanoma in a subject in need thereof.

In one embodiment, provided herein is a pharmaceutical composition for treating melanoma in a subject in need thereof, the composition comprising at least one inhibitor of a EGFR and at least one mitochondrial inhibitor in a pharmaceutically acceptable carrier.

In one embodiment, provided herein is a composition comprising at least one inhibitor of a EGFR and at least one mitochondrial inhibitor for the manufacture of medicament for treating melanoma in a subject in need thereof.

In one embodiment, provided herein is a composition comprising at least one inhibitor of a EGFR and at least one mitochondrial inhibitor for use in treating melanoma in a subject in need thereof.

In one embodiment, provided herein is a pharmaceutical composition for treating melanoma in a subject in need thereof, the composition comprising at least one inhibitor of a PDGFR and at least one mitochondrial inhibitor in a pharmaceutically acceptable carrier.

In one embodiment, provided herein is a composition comprising at least one inhibitor of a PDGFR and at least one mitochondrial inhibitor for the manufacture of medicament for treating melanoma in a subject in need thereof.

In one embodiment, provided herein is a composition comprising at least one inhibitor of a PDGFR and at least one mitochondrial inhibitor for use in treating melanoma in a subject in need thereof.

In one embodiment of any of the compositions described, the inhibitor of B-Raf inhibits B-Raf kinase activity.

In one embodiment of any of the compositions described, the composition further comprises tigecycline or a derivative thereof.

In one embodiment of any of the compositions described, the inhibitor of B-Raf kinase activity is a small molecule.

In some embodiments of the compositions described, the small molecule inhibitor is selected from the group consisting of vemurafenib, GDC-0879, PLX-4720, Sorafenib Tosylate, Regorafenib (BAY 73-4506, Fluoro-Sorafenib), RAF265 (CHIR-265) and derivatives, NVP-BHG712, GW5074, CEP-32496, AZ628, ZM 336372, SB590885, dabrafenib (GSK2118436), and LGX818.

In one embodiment of any of the compositions described, the composition comprises PLX-4720 and tigecycline or a derivative thereof.

In one embodiment of any of the compositions described, the mitochondrial inhibitor is selected from the group consisting of NV-128, ME-344, TTFA, rotenone, 2,4-Dinitrophenol (DNP), meclizine, and oligomycin A.

In one embodiment of any of the compositions described, the OXPHOS inhibitor is selected from the group consisting of oligomycin, malonate, oxaloacetate, barbiturates, rotenone, antimycin-A and arsenate.

In one embodiment of any of the compositions described, the MEK inhibitor is selected from the group consisting of AZD 6244 (Selumetinib; ARRY-142886), PD0325901, CI-1040 (PD184352), U0126-EtOH, PD98059, GSK1120212 (JTP-74057, trametinib), BIX 02189, TAK-733, honokiol, AZD8330 (ARRY-424704), PD318088, BIX 02188, AS703026, MEK162 (ARRY-438162) and XL518.

In one embodiment of any of the compositions described, the ERK inhibitor is selected from the group consisting of SB203580, BIRB 796 (Doramapimod), SB 202190 (FHPI), LY2228820, VX-702, VX-745, PH-797804, and TAK 715.

In one embodiment of any of the compositions described, the c-KIT inhibitor is selected from the group consisting of imatinib, nilotinib, dasatinib (BMS-354825), sunitinib malate (Sutent), axitinib (AG-013736), XL184 (Cabozantinib), Pazopanib Hydrochloride (GW786034, Votrient, Armala), Dovitinib (TKI258, CHIR-258), Regorafenib (BAY 73-4506, Fluoro-Sorafenib), Masitinib (AB1010), Motesanib Diphosphate (AMG-706), AV-951 (Tivozanib, KRN-951), Vatalanib (PTK787), MP-470 (Amuvatinib), OSI-930, Telatinib (BAY 57-9352), Ki8751, Dovitinib (TKI258, CHIR258) and Pazopanib.

In one embodiment of any of the compositions described, the EFGR inhibitor is selected from the group consisting of Erlotinib HCl, Gefitinib (Iressa, ZD-1839), Lapatinib Ditosylate (GW572016, GW2016, Tykerb, Tyverb), BIBW2992 (Afatinib, Tomtovok, Tovok), CI-1033 (Canertinib), Neratinib (HKI-272), CP-724,714, AG 18 (Tyrphostin 23), WHI-P154, TAK-285, AST-1306, ARRY334543, ARRY-380, icotinib, AG-1478 (Tyrphostin AG-1478), Tyrphostin 9 (SF 6847), Dacomitinib (PF299804, PF-00299804), Desmethyl Erlotinib (CP-473420), OSI-420, AZD8931, AEE788 (NVP-AEE788), Pelitinib (EKB-569), CUDC-101, WZ8040, WZ4002, WZ3146, AG-490 (Tyrphostin B42), XL647, PD153035 HCl, and BMS-599626 (AC480).

In one embodiment of any of the compositions described, the EFGR inhibitor is selected from the group consisting of Sorafenib (Nexavar) Sorafenib Tosylate (Bay 43-9006, Nexavar), Imatinib Mesylate, Sunitinib Malate (Sutent, SU11248), Axitinib (AG-013736), BIBF1120 (Vargatef), Pazopanib Hydrochloride (GW786034, Votrient, Armala), Ponatinib (AP24534), MK-2461, Dovitinib (TKI258, CHIR258), Crenolanib (CP-868596), PP-121, DNA-PK with IC50 of 60 nM.S2231 Telatinib (BAY 57-9352) Telatinib (BAY 57-9352) is a potent Imatinib (Gleevec), KRN 633, CP 673451, TSU-68 (SU6668, Orantinib), MP-470 (Amuvatinib), AV-951 (Tivozanib, KRN-951), Masitinib (AB1010), Motesanib Diphosphate (AMG-706), Dovitinib Dilactic acid (TKI258 Dilactic acid), and Linifanib (ABT-869).

In some embodiment of any of the compositions described, the composition is formulated for topical administration or transdermal administration.

In one embodiment of any of the compositions described, the composition is formulated for localized administration and not for systemic administration.

In one embodiment of any of the compositions described, the composition is formulated for systemic administration.

In one embodiment of the use of any compositions described, the subject has been diagnosed with melanoma.

In one embodiment of the use of any compositions described, the use further comprising selecting a subject who has been diagnosed with melanoma.

In one embodiment of the use of any compositions described, the melanoma in the subject comprises at least one mutation in a B-RAF gene therein, or at least one mutation in a NRAS gene therein, at least one mutation is a NF1 gene, or at least one mutation in a c-KIT gene therein.

In one embodiment of the use of any compositions described, the at least one B-RAF gene mutation is a substitution of valine at the 600 amino acid residue of the encoded B-Raf polypeptide.

In one embodiment of the use of any compositions described, the substitution is selected from the group consisting of V600E, V600D, V600K and V600R.

In one embodiment of the use of any compositions described, the at least one B-RAF gene mutation is a substitution of the respective amino acid residue of the encoded B-Raf polypeptide at the following locations: L597S, L597Q, L597R, V600M, V600K, V600R, V600E, V600G, V600D, V600E, and K601E.

In one embodiment of the use of any compositions described, the at least one c-KIT gene mutation is a substitution of the respective amino acid residue of the encoded c-KIT polypeptide at the following locations: W557R, W557R, V559A, V559D, L576P, K642E, and D816H.

In one embodiment of the use of any compositions described, the at least one NRAS gene mutation is a substitution of the respective amino acid residue of the encoded NRAS polypeptide at the following locations: G12C, G12R, G12S, G12A, G12D, G12V, G13R, G13A, G13D, G13V, Q61E, Q61K, Q61L, Q61P, Q61R, Q61L, Q61R, Q61H and Q61H.

In one embodiment, provided herein is a method for treating melanoma in a subject in need thereof, the method comprising administering to the subject a therapeutically effective amount of any of the composition described herein.

In one embodiment, provided herein is a method for treating melanoma in a subject in need thereof, the method comprising providing a subject who has been diagnosed with melanoma; and administering to the subject a therapeutically effective amount of any of the composition described herein.

In one embodiment, provided herein is a method for treating melanoma in a subject in need thereof, the method comprising providing a subject who has been diagnosed with melanoma; analyzing that the melanoma comprises at least one mutation in a B-Raf gene therein, or at least one mutation in a NRAS gene therein, at least one mutation is a NF1 gene, or at least one mutation in a c-KIT gene therein; and administering to the subject a therapeutically effective amount of any of the composition described herein.

In one embodiment, provided herein is a method for treating melanoma in a subject in need thereof, the method comprising providing a subject who has been diagnosed with melanoma; analyzing that the melanoma comprises at least one mutation in a B-Raf gene therein, or at least one mutation in a NRAS gene therein, at least one mutation is a NF1 gene, or at least one mutation in a c-KIT gene therein; and if there is at least one mutation in a B-Raf gene therein, then administering to the subject a therapeutically effective amount of a composition comprising at least one inhibitor of B-Raf and at least one mitochondrial inhibitor in a pharmaceutically acceptable carrier described herein when the melanoma of the subject has at least one mutation in a B-Raf gene therein.

In one embodiment, provided herein is a method for treating melanoma in a subject in need thereof, the method comprising administering to the subject a therapeutically effective amount of a composition comprising at least one inhibitor of B-Raf and at least one mitochondrial inhibitor in a pharmaceutically acceptable carrier described herein.

In one embodiment, provided herein is a method for treating melanoma in a subject in need thereof, the method comprising administering to the subject a therapeutically effective amount of a composition comprising at least one inhibitor of the BRAF pathway, wherein the inhibitor is a MEK inhibitor.

In one embodiment, provided herein is a method for treating melanoma in a subject in need thereof, the method comprising providing a subject who has been diagnosed with melanoma; analyzing that the melanoma comprises at least one mutation in a B-Raf gene therein, or at least one mutation in a NRAS gene therein, at least one mutation is a NF1 gene, or at least one mutation in a c-KIT gene therein; and if there is at least one mutation in a NRAS gene therein, then administering to the subject a therapeutically effective amount of a composition comprising at least one MEK 1 and/or MEK 2 and/or ERK inhibitor and at least one mitochondrial inhibitor in a pharmaceutically acceptable carrier described herein when the melanoma of the subject has at least one mutation in a NRAS gene therein.

In one embodiment, provided herein is a method for treating melanoma in a subject in need thereof, the method comprising administering to the subject a therapeutically effective amount of a composition comprising at least one MEK 1 and/or MEK 2 and/or ERK inhibitor and at least one mitochondrial inhibitor in a pharmaceutically acceptable carrier described herein.

In one embodiment, provided herein is a method for treating melanoma in a subject in need thereof, the method comprising providing a subject who has been diagnosed with melanoma; analyzing that the melanoma comprises at least one mutation in a B-Raf gene therein, or at least one mutation in a NRAS gene therein, at least one mutation is a NF1 gene, or at least one mutation in a c-KIT gene therein; and if there is at least one mutation in a c-KIT gene therein, then administering to the subject a therapeutically effective amount of a composition comprising at least one c-KIT inhibitor and at least one mitochondrial inhibitor in a pharmaceutically acceptable carrier described herein when the melanoma of the subject has at least one mutation in a c-KIT gene therein.

In one embodiment, provided herein is a method for treating melanoma in a subject in need thereof, the method comprising administering to the subject a therapeutically effective amount of a composition comprising at least one c-KIT inhibitor and at least one mitochondrial inhibitor in a pharmaceutically acceptable carrier described herein.

In one embodiment, provided herein is a method of selecting a subject having melanoma for a treatment comprising at least one mitochondrial inhibitor comprising: the method comprising (a) providing a subject who has been diagnosed with melanoma; (b) treating the subject for melanoma for a period of time; (c) measuring the expression level of PGC1 alpha and/or MITF in the melanoma; (d) comparing the expression level of PGC1 alpha is step (c) with a reference level, wherein the reference level is the expression level of PGC1 alpha and/or MITF in the melanoma prior to treatment; (e) selecting the subject for an additional treatment if the level of a measured expression level of PGC1 alpha and/or MITF is at least 2-fold increase over that of the reference level; (f) and administering to the subject a therapeutically effective amount of at least one mitochondrial inhibitor.

In one embodiment, provided herein is a method for treating melanoma in a subject in need thereof, the method comprising (a) providing a subject who has been diagnosed with melanoma; (b) treating the subject with at least one inhibitor of a MAPK pathway for a period of time; (c) measuring the expression level of PGC1 alpha and/or MITF in the melanoma; (d) comparing the expression level of PGC1 alpha is step c with a reference level, wherein the reference level is the expression level of PGC1 alpha and/or MITF in the melanoma prior to treatment with the at least one inhibitor of a MAPK pathway; (e) selecting the subject for an additional treatment if the level of a measured expression level of PGC1 alpha and/or MITF is at least 2-fold increase over that of the reference level; and (f) administering to the subject a therapeutically effective amount of a mitochondrial inhibitor.

In one embodiment, provided herein is a method for treating melanoma in a subject in need thereof, the method comprising (a) providing a subject who has been diagnosed with melanoma; (b) treating the subject with at least one inhibitor of a B-Raf for a period of time; (c) measuring the expression level of PGC1 alpha and/or MITF in the melanoma; (d) comparing the expression level of PGC1 alpha is step c with a reference level, wherein the reference level is the expression level of PGC1 alpha and/or MITF in the melanoma prior to treatment with the at least one inhibitor of a B-Raf; (e) selecting the subject for an additional treatment if the level of a measured expression level of PGC1 alpha and/or MITF is at least 2-fold increase over that of the reference level; and (f) administering to the subject a therapeutically effective amount of a mitochondrial inhibitor.

In one embodiment, provided herein is a method for treating melanoma in a subject in need thereof, the method comprising (a) providing a subject who has been diagnosed with melanoma; (b) treating the subject with an effective amount of tigecycline for a period of time; (c) measuring the expression level of PGC1 alpha in the melanoma; (d) comparing the expression level of PGC1 alpha is step (c) with a reference level, wherein the reference level is the expression level of PGC1 alpha in the melanoma prior to treatment with tigecycline; (e) selecting the subject for an additional treatment if the level of a measured expression level of PGC1 alpha is at least 2-fold increase over that of the reference level; and (f) administering to the subject a therapeutically effective amount of a mitochondrial inhibitor. In one embodiment, the method further comprises administering to the subject a therapeutically effective amount of at least one inhibitor of B-Raf.

In one embodiment, provided herein is a method for treating melanoma in a subject in need thereof, the method comprising (a) providing a subject who has been diagnosed with melanoma; (b) treating the subject with an effective amount of tigecycline and at least one inhibitor of B-Raf for a period of time; (c) measuring the expression level of PGC1 alpha in the melanoma; (d) comparing the expression level of PGC1 alpha is step c with a reference level, wherein the reference level is the expression level of PGC1 alpha in the melanoma prior to treatment with tigecycline and at least one inhibitor of B-Raf; (e) selecting the subject for an additional treatment if the level of a measured expression level of PGC1 alpha is at least 2-fold increase over that of the reference level; and (1) administering to the subject a therapeutically effective amount of a mitochondrial inhibitor.

In one embodiment, provided herein is a method for treating melanoma in a subject in need thereof, the method comprising (a) providing a subject who has been diagnosed with melanoma; (b) treating the subject with at least one inhibitor of a NRAS for a period of time; (c) measuring the expression level of PGC1 alpha and/or MITF in the melanoma; (d) comparing the expression level of PGC1 alpha is step c with a reference level, wherein the reference level is the expression level of PGC1 alpha and/or MITF in the melanoma prior to treatment with the at least one inhibitor of a NRAS; (e) selecting the subject for an additional treatment if the level of a measured expression level of PGC1 alpha and/or MITF is at least 2-fold increase over that of the reference level; and (f) administering to the subject a therapeutically effective amount of a mitochondrial inhibitor.

In one embodiment, provided herein is a method for treating melanoma in a subject in need thereof, the method comprising (a) providing a subject who has been diagnosed with melanoma; (b) treating the subject with at least one inhibitor of a c-KIT for a period of time; (c) measuring the expression level of PGC1 alpha and/or MITF in the melanoma; (d) comparing the expression level of PGC1 alpha is step c with a reference level, wherein the reference level is the expression level of PGC1 alpha and/or MITF in the melanoma prior to treatment with the at least one inhibitor of a c-KIT kinase; (e) selecting the subject for an additional treatment if the level of a measured expression level of PGC1 alpha and/or MITF is at least 2-fold increase over that of the reference level; and (0 administering to the subject a therapeutically effective amount of a mitochondrial inhibitor.

In one embodiment, provided herein is a method for treating melanoma in a subject in need thereof, the method comprising (a) providing a subject who has been diagnosed with melanoma; (b) treating the subject with at least one inhibitor of a EGFR or a PDGFR for a period of time; (c) measuring the expression level of PGC1 alpha and/or MITF in the melanoma; (d) comparing the expression level of PGC1 alpha is step c with a reference level, wherein the reference level is the expression level of PGC1 alpha and/or MITF in the melanoma prior to treatment with the at least one inhibitor of the respective EGFR or PDGFR; (e) selecting the subject for an additional treatment if the level of a measured expression level of PGC1 alpha and/or MITF is at least 2-fold increase over that of the reference level; and (f) administering to the subject a therapeutically effective amount of a mitochondrial inhibitor.

In one embodiment, provided herein is a method of selecting a subject having melanoma for a treatment comprising at least one mitochondrial inhibitor comprising: (a) measuring the expression level of PGC1 alpha and/or MITF in the melanoma; (b) comparing the expression level of PGC1 alpha and/or MITF with a reference level, wherein the reference level is the expression level of PGC1 alpha or MITF in the melanoma prior to a treatment for melanoma; (c) selecting the subject for an additional treatment if the level of a measured expression level of PGC1 alpha and/or MITF is at least 2-fold increase over that of the reference level; and (d) administering to the subject a therapeutically effective amount of a mitochondrial inhibitor.

In one embodiment of any of the methods described, the subject has been diagnosed with melanoma.

In one embodiment of any of the methods described, the method further comprises selecting a subject who has been diagnosed with melanoma.

In one embodiment of any of the methods described, the method further comprises selecting a subject is currently being treated for melanoma.

In one embodiment of any of the methods described, the subject is treated with a composition comprising PLX-4720 and tigecycline or a derivative thereof.

In one embodiment of any of the methods described, the subject is treated with PLX-4720 and tigecycline or a derivative thereof.

In one embodiment of any of the methods described, the treatment for melanoma comprises administering at least one inhibitor of a MAPK pathway. In other embodiments of any of the methods described, the treatment for melanoma comprises administering at least one MEK 1 and/or MEK2 inhibitor and/or at least one ERK inhibitor. In other embodiments of any of the methods described, the treatment for melanoma comprises administering at least one c-KIT inhibitor. In other embodiments of any of the methods described, the treatment for melanoma comprises administering at least one B-Raf inhibitor In one embodiment of any of the method described, the method further comprises analyzing that the melanoma comprises at least one mutation in a B-Raf gene therein, or at least one mutation in a NRAS gene therein, at at least one mutation is a NF1 gene, or at least one mutation in a c-KIT gene therein; and if there is at least one mutation in a c-KIT gene therein. In other embodiments of any of the method described, the method further comprises analyzing that the melanoma comprises any mutations in a B-Raf gene, a NRAS gene, and a c-KIT therein.

In one embodiment of any of the method described, the melanoma in the subject comprises at least one mutation in a B-RAF gene therein, at least one mutation is a NF1 gene, or at least one mutation in a NRAS gene therein, or at least one mutation in a c-KIT gene therein.

In one embodiment of any of the method described, the melanoma comprises at least one mutation in the B-RAF gene therein.

In one embodiment of any of the method described, the at least one B-RAF gene mutation is a substitution of valine at the 600 amino acid residue of the encoded B-Raf polypeptide.

In one embodiment of any of the method described, the substitution is selected from the group consisting of V600E, V600D, V600K and V600R.

In one embodiment of any of the method described, the at least one B-RAF gene mutation is a substitution of the respective amino acid residue of the encoded B-Raf polypeptide at the following locations: L597S, L597Q, L597R, V600M, V600K, V600R, V600E, V600G, V600D, V600E, and K601E.

In one embodiment of any of the method described, the at least one c-KIT gene mutation is a substitution of the respective amino acid residue of the encoded c-KIT polypeptide at the following locations: W557R, W557R, V559A, V559D, L576P, K642E, and D816H.

In one embodiment of any of the method described, the at least one NRAS gene mutation is a substitution of the respective amino acid residue of the encoded NRAS polypeptide at the following locations: G12C, G12R, G12S, G12A, G12D, G12V, G13R, G13A, G13D, G13V, Q61E, Q61K, Q61L, Q61P, Q61R, Q61L, Q61R, Q61H and Q61H.

In one embodiment of any of the method described, the period of time after treatment at which the measurement of PGC1 alpha and/or MITF expression is performed is anywhere from about 2 days to about one month. In other embodiments, the measurement can be performed anywhere up to 6 months as prophylaxis against the development of drug resistance of the melanoma where prior measurements do not produced an at least two fold increase in expression level.

In one embodiment, provided herein is a method for promoting cell death in a cell, the method comprising the step of contacting a cell with an effective amount of a composition described herein. For example, the composition comprises at least one inhibitor of a MAP kinase and at least one mitochondrial inhibitor, or comprises at least one inhibitor of B-Raf and at least one mitochondrial inhibitor, or comprises at least one inhibitor of MEK1 and/or MEK 2 and/or ERK and at least one mitochondrial inhibitor, comprises or at least one inhibitor of NRAS and at least one mitochondrial inhibitor.

In one embodiment, provided herein is a method for promoting cell death of suppression of growth in a cell, the method comprising the step of providing a melanoma cell; analyzing that the melanoma cell comprises at least one gene mutation therein; and contacting the melanoma cell with an effective amount of a composition comprising at least one inhibitor of a MAP kinase and at least one mitochondrial inhibitor described herein.

In one embodiment of any methods described, the at least one gene mutation analyzed is in a B-RAF gene therein, in a NF1 gene, or in a NRAS gene therein, or in a c-KIT gene therein.

In one embodiment of any methods described, the cell is a melanoma cell.

In one embodiment of any methods described, the melanoma cell comprises at least one mutation in a B-RAF gene therein.

In one embodiment of any methods described, the at least one B-RAF gene mutation is a substitution of valine at the 600 amino acid residue of the encoded B-Raf polypeptide.

In one embodiment of any methods described, the substitution is selected from the group consisting of V600E, V600D, V600K and V600R.

In one embodiment of any of the method described, the at least one B-RAF gene mutation is a substitution of the respective amino acid residue of the encoded B-Raf polypeptide at the following locations: L597S, L597Q, L597R, V600M, V600K, V600R, V600E, V600G, V600D, V600E, and K601E.

In one embodiment of any methods described, the melanoma cell comprises at least one mutation in a NRAS gene therein.

In one embodiment of any of the method described, the at least one NRAS gene mutation is a substitution of the respective amino acid residue of the encoded NRAS polypeptide at the following locations: G12C, G12R, G12S, G12A, G12D, G12V, G13R, G13A, G13D, G13V, Q61E, Q61K, Q61L, Q61P, Q61R, Q61L, Q61R, Q61H and Q61H.

In one embodiment of any methods described, the melanoma cell comprises at least one mutation in a C-KIT gene therein.

In one embodiment of any of the method described, the at least one c-KIT gene mutation is a substitution of the respective amino acid residue of the encoded c-KIT polypeptide at the following locations: W557R, W557R, V559A, V559D, L576P, K642E, and D816H.

In one embodiment, the cell is contacted with the composition ex vivo, in vitro or in vivo.

In one embodiment of any of the methods described, the at least one inhibitor of a MAPK pathway is an inhibitor of B-Raf, an inhibitor of c-KIT, an inhibitor of MEK 1 or MEK2 or both, or an inhibitor of ERK.

In one embodiment of any one of the method described, the at least one inhibitor of a MAPK pathway is an epidermal growth factor receptor (EGFR) inhibitor.

In one embodiment of any one of the method described, the at least one inhibitor of a MAPK pathway is a platelet-derived growth factor receptor (PDGFR) inhibitor.

In one embodiment of any of the methods described, the at least one mitochondrial inhibitor is an inhibitor of oxidative phosphorylation (OXPHOS).

In one embodiment of any of the methods described, the inhibitor of B-Raf inhibits B-Raf kinase activity.

In one embodiment of any of the methods described, the inhibitor of B-Raf kinase activity is a small molecule.

In some embodiments of the methods described, the small molecule inhibitor is selected from the group consisting of vemurafenib, GDC-0879, PLX-4720, Sorafenib Tosylate, Regorafenib (BAY 73-4506, Fluoro-Sorafenib), RAF265 (CHIR-265) and derivatives, NVP-BHG712, GW5074, CEP-32496, AZ628, ZM 336372, SB590885, dabrafenib (GSK2118436), and LGX818.

In one embodiment of any of the methods described, the mitochondrial inhibitor is selected from the group consisting of NV-128, ME-344, TTFA, tigecycline, rotenone, 2,4-Dinitrophenol (DNP), meclizine, and oligomycin A.

In one embodiment of any of the methods described, the OXPHOS inhibitor is selected from the group consisting of oligomycin, malonate, oxaloacetate, barbiturates, rotenone, antimycin-A and arsenate.

In one embodiment of any of the methods described, the MEK inhibitor is selected from the group consisting of AZD 6244 (Selumetinib; ARRY-142886), PD0325901, CI-1040 (PD184352), U0126-EtOH, PD98059, GSK1120212 (JTP-74057, trametinib), BIX 02189, TAK-733, honokiol, AZD8330 (ARRY-424704), PD318088, BIX 02188, AS703026, MEK162 (ARRY-438162) and XL518.

In one embodiment of any of the methods described, the ERK inhibitor is selected from the group consisting of SB203580, BIRB 796 (Doramapimod), SB 202190 (FHPI), LY2228820, VX-702, VX-745, PH-797804, and TAK 715.

In one embodiment of any of the method described, the c-KIT inhibitor is selected from the group consisting of imatinib, nilotinib, dasatinib (BMS-354825), sunitinib malate (Sutent), axitinib (AG-013736), XL184 (Cabozantinib), Pazopanib Hydrochloride (GW786034, Votrient, Armala), Dovitinib (TKI258, CHIR-258), Regorafenib (BAY 73-4506, Fluoro-Sorafenib), Masitinib (AB1010), Motesanib Diphosphate (AMG-706), AV-951 (Tivozanib, KRN-951), Vatalanib (PTK787), MP-470 (Amuvatinib), OSI-930, Telatinib (BAY 57-9352), Ki8751, Dovitinib (TKI258, CHIR258) and Pazopanib.

In one embodiment of any of the methods described, the EFGR inhibitor is selected from the group consisting of Erlotinib HCl, Gefitinib (Iressa, ZD-1839), Lapatinib Ditosylate (GW572016, GW2016, Tykerb, Tykerb), BIBW2992 (Afatinib, Tomtovok, Tovok), CI-1033 (Canertinib), Neratinib (HKI-272), CP-724,714, AG 18 (Tyrphostin 23), WHI-P154, TAK-285, AST-1306, ARRY334543, ARRY-380, icotinib, AG-1478 (Tyrphostin AG-1478), Tyrphostin 9 (SF 6847), Dacomitinib (PF299804, PF-00299804), Desmethyl Erlotinib (CP-473420), OSI-420, AZD8931, AEE788 (NVP-AEE788), Pelitinib (EKB-569), CUDC-101, WZ8040, WZ4002, WZ3146, AG-490 (Tyrphostin B42), XL647, PD153035 HCl, and BMS-599626 (AC480).

In one embodiment of any of the methods described, the EFGR inhibitor is selected from the group consisting of Sorafenib (Nexavar) Sorafenib Tosylate (Bay 43-9006, Nexavar), Imatinib Mesylate, Sunitinib Malate (Sutent, SU11248), Axitinib (AG-013736), BIBF1120 (Vargatef), Pazopanib Hydrochloride (GW786034, Votrient, Armala), Ponatinib (AP24534), MK-2461, Dovitinib (TKI258, CHIR258), Crenolanib (CP-868596), PP-121, DNA-PK with 1050 of 60 nM.S2231 Telatinib (BAY 57-9352) Telatinib (BAY 57-9352) is a potent Imatinib (Gleevec), KRN 633, CP 673451, TSU-68 (SU6668, Orantinib), MP-470 (Amuvatinib), AV-951 (Tivozanib, KRN-951), Masitinib (AB1010), Motesanib Diphosphate (AMG-706), Dovitinib Dilactic acid (TK1258 Dilactic acid), and Linifanib (ABT-869).

As used herein, the term "comprising" or "comprises" is used in reference to methods and compositions, and respective component(s) thereof, that are essential to the invention, yet open to the inclusion of unspecified elements, whether essential or not. The use of "comprising" indicates inclusion rather than limitation.

The term "consisting of" refers to methods, and respective components thereof as described herein, which are exclusive of any element not recited in that description of the embodiment.

As used herein, the term "inhibitor" when used in reference to the MAPK pathway, B-Raf, NRAS and/or c-KIT, refers to an agent that inhibits the normal cellular activities of the proteins that are involved, that constitute, or that are participants in the MAPK pathway, or the normal cellular activities of B-Raf, NRAS and/or c-KIT.

As used herein, the term "inhibit" or "inhibition" when used in reference to the MAPK pathway, B-Raf, NRAS, NF-1 and/or c-KIT, means the reduction or prevention of the normal cellular activities of the proteins that are involved, that constitute, or that are participants in the MAPK pathway, or the normal cellular activities of B-Raf, NRAS and/or c-KIT. These proteins are mostly enzymes. Accordingly, "inhibit" or "inhibition" refers to the reduction of the catalytic activities of these enzymes. The reduction can be by about 20%, about 30%, about 40%, about 50%, about 60%, about 70%, about 80%, about 90%, about 100%, about 125%, about 150% or more compared to the catalytic activities of these enzymes in the absence of the inhibitor. Assay methods for determining enzyme activity inhibition are known in the art.

As used herein, the term "a MAPK pathway inhibitor" refers to an inhibitor of any one of a chain of proteins in the cell that communicates a signal from a receptor on the surface of the cell to the DNA in the nucleus of the cell. The chain of proteins include a kinase cascade comprising MAPK which is also known as mitogen-activated protein kinases, originally called ERK, Extracellular signal-regulated kinases, and also include Ras (a GTPase), Raf (a MAP3K), and MEK (mitogen-activated protein kinase kinase, MAPKK). Non-limiting examples of Raf inhibitors are sorafenib, SB590885, PLX4720, XL281, RAF265, LGX818, and vemurafenib. Non-limiting examples of MEK inhibitors are XL518, CI-1040, PD035901, MEK162, selumetinib, and trametinib (GSK1120212).

As used herein, the term "mitochondrial inhibitor" refers to an inhibitor of mitochondrial function which includes electron transport inhibitors, uncouplers of oxidative phosphorylation, respiratory chain inhibitors, phosphorylation inhibitors, ionophores, and Krebs cycle inhibitors. Non-limiting examples are hexokinase II inhibitor II, 3-BP; hexokinase II VDAC binding domain peptide, cell-permeable; m-iodobenzylguanidine, hemisulfate; mitochondrial division inhibitor, mdivi-1; oligomycin; tigecycline; rotenone; Ru360, and valinomycin derived from *Streptomyces fulvissimus*.

As used herein, the term "oxidative phosphorylation inhibitor" refers to inhibitors that block the process of formation of ATP. Oxidative phosphorylation (or OXPHOS in short) is the metabolic pathway in which the mitochondria in cells use their structure, enzymes, and energy released by the oxidation of nutrients to move hydrogen from ADP to phosphate to reform ATP. The "oxidative phosphorylation inhibitor" can inhibit any one of the many enzymes in the electron transport chain, because inhibition of any step in this process will halt the rest of the process. For example, if oligomycin inhibits ATP synthase, protons cannot pass back into the mitochondrion. As a result, the proton pumps are unable to operate, as the gradient becomes too strong for them to overcome. NADH is then no longer oxidized and the citric acid cycle ceases to operate because the concentration of NAD+ falls below the concentration that these enzymes can use. Non-limiting examples of an oxidative phosphorylation inhibitor are cyanide, carbon monoxide, azide, oligomycin, CCCP and 2,4-dinitrophenol (uncouples proton pumping from ATP synthesis), rotenone, and malonate and oxaloacetate (competitive inhibitors of succinate dehydrogenase (complex II)).

As used herein, the term "mutation" with respect to a gene refers to a change of the nucleotide sequence of the gene of an organism. In some embodiments, the "mutations" referred to herein can take the form of one or more nucleotides deletions, one or more nucleotides additions, or one or more nucleotides substitutions. In some embodiments, the "mutations" referred to herein have the effects of one or more amino acids deletions, one or more amino acids additions, or one or more amino acids substitutions when the mutated gene is transcribed and translated into a polypeptide.

As used herein, the term "a B-Raf mutation" refers to a change of the nucleotide sequence of the B-Raf gene such that there is one or more amino acids deletions, one or more amino acids additions, or one or more amino acids substitutions when the mutated gene is transcribed and translated into a BRAF polypeptide.

As used herein, the term "a NRAS mutation" refers to a change of the nucleotide sequence of the NRAS gene such that there is one or more amino acids deletions, one or more amino acids additions, or one or more amino acids substitutions when the mutated gene is transcribed and translated into a NRAS polypeptide.

As used herein, the term "a c-KIT mutation" refers to a change of the nucleotide sequence of the c-KIT gene such that there is one or more amino acids deletions, one or more amino acids additions, or one or more amino acids substitutions when the mutated gene is transcribed and translated into a c-KIT polypeptide.

As used herein, the term "a NF-1 mutation" refers to a change of the nucleotide sequence of the NF-1 gene such that there is one or more amino acids deletions, one or more amino acids additions, or one or more amino acids substitutions when the mutated gene is transcribed and translated into a NF-1 polypeptide.

As used herein, the term "an activated mutation" or "an activating mutation" refers to a change of the nucleotide sequence of a gene such that when the mutated gene is transcribed and translated into a mutant polypeptide, the mutated polypeptide in constitutively active, and is not responsive of any of the normal regulatory mechanism available in vivo, wherein the normal regulatory mechanism available in vivo can activate and also deactivate the normal, non-mutated polypeptide.

The term "constitutive" use herein refers to "all the time" or constantly.

As used herein, the term "gene" with references to mutations means the nucleic acid sequence which is transcribed (DNA) and translated (mRNA) into a polypeptide in vitro or in vivo when operably linked to appropriate regulatory sequences. The gene may or may not include regions preceding and following the coding region, e.g. 5' untranslated (5'UTR) or "leader" sequences and 3' UTR or "trailer" sequences, as well as intervening sequences (introns) between individual coding segments (exons).

As used herein, the term "amino acid" is intended to include naturally occurring amino acids (alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine) Amino acids can be referred to herein by either their commonly known three letter symbols or by the one-letter symbols recommended by the IUPAC-IUB Biochemical Nomenclature Commission.

As used herein, the abbreviations of amino acid substitutions for a particular amino acid residue at a particular position in a polypeptide is indicated by a first single upper case alphabet followed by a number which is then followed by a second single upper case alphabet. For example, K500L. In this example, the first single upper case alphabet is the original amino acid normally found at position 500 of the polypeptide, and the second single upper case alphabet is the substitution amino acid for the original amino acid. In this example, lysine at position 500 of the polypeptide is substituted by leucine.

As used herein, "administration" and "administering," as it applies to a subject, refers to contact of an exogenous pharmaceutical, therapeutic, or composition to the subject.

As used herein, "subject" refers to a mammal. In another embodiment, the subject is a human.

As used herein, the term "pharmaceutical composition" refers to the active agent (e.g., MAPK pathway inhibitors) in combination with a pharmaceutically acceptable carrier of chemicals and compounds commonly used in the pharmaceutical industry.

The term "effective amount" means a dosage sufficient to provide treatment for the cancer state being treated. This will vary depending on the patient, the cancer and the treatment being effected.

In one embodiment, the term "treat" or "treatment" in the context of melanoma refers to the therapeutic treatment wherein the object is to slow down, and/or halt the development or spread of cancer. Beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. In another embodiment, "treatment" can also mean prolonging survival as compared to expected survival if not receiving treatment. Those in need of treatment include those already diagnosed with cancer as well as those likely to develop secondary tumors due to metastasis. Accordingly, in another embodiment, the term "treat" or "treatment" in the context of melanoma, refers to preventative measures, wherein the object is to prophylactic prevent recurrences of the cancer after the initial or existing and known cancer lesions have been removed or growth and development have been halted.

BRIEF LISTING OF TABLES

Tables 1A, 1B and 1C. Gene expression changes following treatment of cell lines with BRAF or MEK inhibitors. Gene expression sets enriched after treatment of melanomas with vemurafenib (Table 1A) or MEK inhibitor PD0325901 (Table 1B). Gene expression sets enriched after treatment of non-melanomas with PD0325901 (Table 1C). FDR, false-discovery rate; FWER, family-wise error rate; ES, enrichment score; NES, normalized enrichment score; Size refers to gene set size. Details of statistical methods are described in (Mootha et al., 2003).

Table 2. Mutagenesis primer sequences

BRIEF DESCRIPTION OF THE DRAWINGS

FIGS. 1A-1F show that BRAF inhibitors induce mitochondrial biogenesis and oxidative metabolism.

FIG. 1A is a representative of a gene set enrichment analysis plot of melanoma cells treated with vemurafenib showing the most significantly changed gene set. FDR, false-discovery rate; ES, enrichment score.

FIG. 1B are histograms showing that MITOTRACKER® green fluorescence of BRAF mutant (UACC-62 and UACC-257) or BRAF wild-type (MeWo) melanoma cell lines treated with PLX4720 (1 µM, 72 h) and subjected to analysis by flow cytometry.

FIG. 1C are histograms showing that MITOTRACKER® red fluorescence of BRAF mutant (UACC-62) melanoma cell lines treated with PLX4720 (1 µM, 72 h) and subjected to analysis by flow cytometry.

FIG. 1D are histograms showing that MITOSOX™ of BRAF mutant (UACC-62) melanoma cell lines treated with PLX4720 (1 µM, 72 h) and subjected to analysis by flow cytometry.

FIG. 1E are representative electron micrographs of UACC-62 cells treated with PLX4720 or vehicle control. Representative photographs of cells at 22000× (upper panel) or 44000× (lower panel) are shown. Arrows indicate mitochondria.

FIG. 1F are histograms showing the lactate levels in media conditioned from the indicated cell lines treated with PLX4720 or vehicle control for 16 hours. Error bars represent SEM of at least three independent replicates. *, $p<0.001$; , $p<0.01$.

FIGS. 2A-2F show that BRAF inhibitors induce PGC1α expression.

FIG. 2A are histograms showing the expression of PGC1α mRNA in melanoma or colon cancer cells treated with PLX4720 (1 µM) for 24 h. Error bars represent SEM of at least three independent replicates. ***, $p<0.001$; *, $p<0.01$.

FIG. 2B are representative Western blots showing the ERK activity in melanoma or colon cancer cells treated with PLX4720 (1 µM) for 24 h.

FIG. 2C are histograms showing the expression of PGC1α mRNA in melanoma cells treated with the MEK inhibitor PD0325901 (10 nM) for 24 h. Error bars represent SEM of at least three independent replicates. ****, $p<0.0001$; *, $p<0.01$.

FIG. 2D are representative Western blots showing the ERK activity in melanoma cells treated with the MEK inhibitor PD0325901 (10 nM) for 24 h.

FIG. 2E shows the microarray analysis (GSE10086) of PGC1α mRNA in cell lines treated with 10 nM PD0325901 for 24 h.

FIG. 2F shows the comparison of PGC1α mRNA with MITF, melanocytic markers, and MITF targets in 105 melanoma cell cultures (Hoek et al., 2006). Pearson correlation co-efficient is shown at the bottom of each column.

FIGS. 3A-3H show that PGC1α is regulated by MITF in the melanocytic lineage.

FIG. 3A shows the top 10 transcription factors correlated to PGC1α mRNA (Lin et al., 2008). *, $q<0.05$.

FIGS. 3B-3C are histograms showing the requirement of MiT family members for PGC1α expression in M14 melanoma cells. Knockdown of each family member is shown. **, $p<0.0001$; , $p<0.01$.

FIG. 3D is a schematic diagram showing the structure of the PGC1α promoter in mammalian species indicating the location of alternative exon 1 and exon 1. Also depicted are the locations of E-box #1 and E-box #2 and primers used for chromatin immunoprecipitation.

FIG. 3E are histograms showing the chromatin immunoprecipitation of indicated genomic region with anti-MITF, or rabbit IgG in primary melanocytes. Precipitated DNA was amplified using primers depicted in (d). ***, $p<0.001$ compared to Rabbit IgG control.

FIG. 3F are histograms showing the activity of PGC1α promoters upstream of the luciferase gene mutated as depicted in response to transfection of MITF. Error bars represent SEM of at least three independent replicates. ***, $p<0.001$.

FIG. 3G are histograms showing the activity of PGC1α promoters upstream of the luciferase gene mutated as depicted in response to treatment with PLX4720. Error bars represent SEM of at least three independent replicates. ***, $p<0.001$.

FIG. 3H are histograms showing the expression of PGC1α following knockdown of MITF (48 h) and treatment with PLX4720 (1 μM, 24 h) in M14 cells (left) or UACC-62 cells (right). Error bars represent SEM of at least three independent replicates. ***, $p<0.001$.

FIGS. 4A-4F show that BRAF suppresses MITF expression and activity.

FIG. 4A are Western gel blots showing the levels of M-MITF (arrows) and phosphorylated ERK in pmel* and pmel* BRAF (V600E).

FIG. 4B shows the effects of MEK inhibitor PD0325901 on MITF mRNA and MITF targets by published microarray (Pratilas et al., 2009).

FIG. 4C are histograms showing the response of MITF and MITF targets to PLX4720 in UACC-257 cells by quantitative PCR. *, $p<0.01$; ***, $p<0.001$ relative to DMSO control.

FIG. 4D are histograms showing the effect of MITF suppression on induction of MITF-target TRPM1 by PLX4720. , $p<0.01$; *, $p<0.001$ relative to siControl. Error bars represent SEM of at least three independent replicates.

FIG. 4E shows the consequence of PLX4720 (72 h) on UACC-257 pigmentation. Equal number of cells was pelleted by centrifugation.

FIG. 4F shows the expression of MITF (left) and PGC1α in melanoma cells with high or low MAPK activation from 88 short-term melanoma cultures (Lin et al., 2008).

FIG. 5A are representative histological slides showing the expression of phospho-ERK in eight matched patient biopsies prior or during (10-14 days) of treatment with BRAF/MEK inhibitors.

FIG. 5B are histograms showing the expression of PGC1α mRNA prior and during treatment with BRAF/MEK inhibitors. Error bars represent SEM of at least three technical replicates.

FIG. 6A shows the comparison of MITF expression in melanomas with high expression of a PGC1α-target gene set (bottom) or oxidative phosphorylation gene set (top).

FIG. 6B are representative Western blots showing the expression of MITF and PGC1α in pmel* BRAF(V600E) with and without MITF overexpression.

FIG. 6C is a schematic diagram showing an isogenic system for evaluating the effect of MITF overexpression in BRAF(V600E) melanoma cells. The tumorigenicity of the paired cell lines was assessed in FoxNnu mice and the number of formed tumors per injection of each cell line is shown. Gene set enrichment analysis of the paired cell lines with the most highly induced gene sets is shown (right).

FIG. 6D are histograms showing the glucose uptake measured as relative amounts in each cell line, normalized to cell number.

FIG. 6E are histograms showing the lactate levels measured as relative amounts in each cell line, normalized to cell number. ***, $p<0.001$ compared to control cells. Error bars represent SEM of at least three independent replicates.

FIG. 6F are histograms showing the oxygen consumption measured as relative amounts in each cell line, normalized to cell number.

FIG. 6G are histograms showing the ATP levels, normalized to cell number in BRAF(V600E)+vector and BRAF (V600E)+MITF treated with PLX4032 (1 μM) for 24 h. ***, $p<0.001$ compared to control cells. Error bars represent SEM of at least three independent replicates.

FIG. 7A are histograms showing the number of BRAF (V600E)+vector and BRAF(V600E)+MITF melanoma cells following treatment with 2,4-DNP with indicated dose for 72 h.

FIG. 7B are histograms showing the levels of ATP in melanoma cell lines treated with vemurafenib (1 μM) for 24 h.

FIG. 7C are histograms showing the PGC1α mRNA in melanoma cell lines treated with vemurafenib (1 μM) for 24 h.

FIG. 7D are histograms showing the effects of 2,4-DNP (50 μg/mL, 24 h) on ATP in the indicated cell lines in vitro.

FIG. 7E are histograms showing the effects of 2,4-DNP (50 μg/mL, 24 h) on the lactate levels in the indicated cell lines in vitro.

FIG. 7F are line graphs showing the effect of 2,4-DNP (20 mg/kg/day) or vemurafenib (75 mg/kg/day) on murine melanoma xenografts of UACC-257 cell line (n=7-8 per group). , $p<0.01$ compared to vehicle group; *, $p<0.001$ compared to vehicle group. Error bars represent SEM of at least three independent replicates.

FIG. 7G are line graphs showing the effect of 2,4-DNP (20 mg/kg/day) or vemurafenib (75 mg/kg/day) on murine melanoma xenografts of A375P cell line (n=7-8 per group). , $p<0.01$ compared to vehicle group; *, $p<0.001$ compared to vehicle group. Error bars represent SEM of at least three independent replicates.

FIG. 8A shows the sensitivity of A375M melanoma cells overexpressing PGC1α to treatment with PLX4720 for 72 hours.

FIG. 8B shows the sensitivity of WM1575 melanoma cells overexpressing PGC1α to treatment with PLX4720 for 72 hours.

FIG. 8C shows the sensitivity of UACC-257 melanoma cells overexpressing PGC1α to treatment with PLX4720 for 72 hours.

FIG. 8D are representative photographs of M14 cells treated with PLX4720 (5 μM), CCCP (20 μM) or the combination for 72 hrs.

FIG. 8E shows the cell number following treatment with mitochondrial uncouplers oligomycin A (1 μM), CCCP (5 μM) or 2,4-DNP (200 μg/mL). Cell number was estimated after 72 hrs of treatment. *, $p<0.05$ compared to control; , $p<0.01$ compared to control; *, $p<0.001$ compared to control. Error bars represent SEM of at least three independent replicates.

FIG. 9A are histograms showing the induction of OXPHOS genes in A375P cell upon treatment with PLX4032.

FIG. 9B are histograms showing the induction of OXPHOS genes in MALME-3M cells upon treatment with PLX4032.

FIG. 9C are histograms showing the induction of OXPHOS genes in SK-MEL-5 upon treatment with PLX4032.

FIG. 12A is a representative expression profile showing the effect of MITF overexpression on oxidative phosphorylation gene set. Low expression is depicted in darker shades of grey, whereas higher expression is in lighter shade of grey.

FIG. 12F shows the oxidative phosphorylation or oxidative stress genes by microarray (Li et al., 2012) affected by the shMITF. Fold change after expression of shMITF are shown. Binding of MITF to the proximal promoter of each gene was determined by ChIP-on-ChIP (Li et al., 2012). Error bars represent SEM of at least three independent replicates.

FIG. 15A shows that genetic suppression of EFTu (mitochondrial translational regulator) enhances apoptosis induced of the BRAF inhibitor PLX4720 (doses listed at 0, 1 and 10 µM).

FIG. 15B shows that suppression of mitochondrial translation using tigecycline strongly potentiates apoptosis induced by BRAF inhibitor PLX4720.

DETAILED DESCRIPTION OF THE INVENTION

Figure 1F:
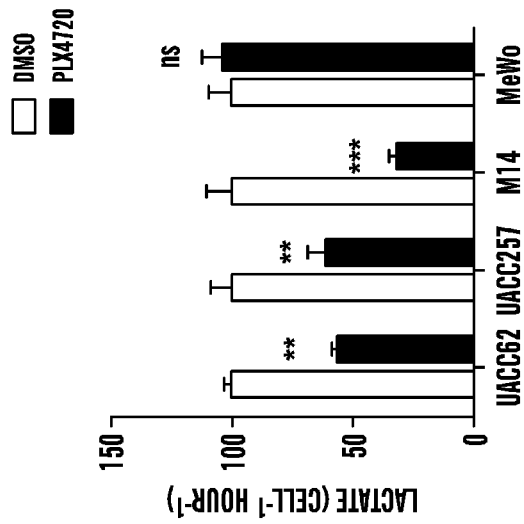

Unless otherwise explained, all technical and scientific terms used herein have the same meaning as commonly understood by one of ordinary skill in the art to which this disclosure belongs. Definitions of common terms in molecular biology may be found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8). Further, unless otherwise required by context, singular terms shall include pluralities and plural terms shall include the singular.

Unless otherwise stated, the present invention was performed using standard procedures known to one skilled in the art, for example, in Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); Current Protocols in Molecular Biology (CPMB) (Fred M. Ausubel, et al. ed., John Wiley and Sons, Inc.), Current Protocols in Immunology (CPI) (John E. Coligan, et. al., ed. John Wiley and Sons, Inc.), Current Protocols in Cell Biology (CPCB) (Juan S. Bonifacino et. al., ed John Wiley and Sons, Inc.), Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998), Methods in Molecular biology, Vol. 180, Transgenesis Techniques by Alan R. Clark editor, second edition, 2002, Humana Press, and Methods in Molecular Biology, Vo. 203, 2003, Transgenic Mouse, edited by Marten H. Hofker and Jan van Deursen, which are all herein incorporated by reference in their entireties.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used in connection with percentages will mean±1%.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

BRAF mutations are the most common genetic aberrations in melanoma but the mechanisms by which they promote oncogenesis are poorly understood. Inventors show that activated BRAF promotes metabolic reprogramming by suppression of oxidative phosphorylation through the actions of the melanocyte lineage factor MITF and the mitochondrial master regulator PGC1α. BRAF inhibitors, which transiently suppress melanoma growth in vitro and in patients, induce PGC1α and oxidative phosphorylation. This addiction to oxidative phosphorylation in melanomas treated with BRAF targeted therapy therefore indicates that mitochondrial inhibitors can be used in combination with BRAF pathway inhibitors for a more effective therapy.

Activating mutations in BRAF are a common genetic alteration in melanoma Inhibition of BRAF by small molecule inhibitors leads to cell cycle arrest and apoptosis. As disclosed herein, BRAF inhibition also induces an oxidative phosphorylation gene program, mitochondrial biogenesis, and the increased expression of the mitochondrial master regulator, PGC1α. As further disclosed herein, a target of BRAF, the melanocyte lineage factor MITF, directly regulates the expression of PGC1α. Melanomas with activation of the BRAF/MAPK pathway have suppressed levels of MITF and PGC1α, and decreased oxidative metabolism. Conversely, treatment of BRAF mutated melanomas with BRAF inhibitors renders them addicted to oxidative phosphorylation. Thus, in accordance with an embodiment herein, a novel adaptive metabolic program that limits the efficacy of BRAF inhibitors is identified.

Accordingly, embodiments of the present disclosure are related to combinatorial compositions and the uses thereof for the purpose of treating melanoma and cancer generally.

In one embodiment, provided herein is a method for treating melanoma in a subject in need thereof, the method comprising administering to the subject a therapeutically effective amount of a composition comprising at least one inhibitor of a MAPK pathway and at least one mitochondrial inhibitor in a pharmaceutically acceptable carrier.

In one embodiment, provided herein is a method for treating melanoma in a subject in need thereof, the method comprising providing a subject who has been diagnosed with melanoma; and administering to the subject a therapeutically effective amount of a composition comprising at least one inhibitor of a MAPK pathway and at least one mitochondrial inhibitor in a pharmaceutically acceptable carrier.

In one embodiment, provided herein is a method for treating melanoma in a subject in need thereof, the method comprising providing a subject who has been diagnosed with melanoma; analyzing that the melanoma comprises at least one mutation in a B-Raf gene therein, or at least one mutation in a NRAS gene therein, at least one mutation is a NF1 gene, or at least one mutation in a c-KIT gene therein; and administering to the subject a therapeutically effective amount of a composition comprising at least one inhibitor of a MAPK pathway and at least one mitochondrial inhibitor in a pharmaceutically acceptable carrier.

In one embodiment, provided herein is a method for treating melanoma in a subject in need thereof, the method comprising providing a subject who has been diagnosed with melanoma; analyzing that the melanoma comprises at least one mutation in a B-Raf gene therein, or at least one mutation in a NRAS gene therein, at least one mutation is a NF1 gene, or at least one mutation in a c-KIT gene therein; and if there is at least one mutation in a B-Raf gene therein, then administering to the subject a therapeutically effective amount of a composition comprising at least one inhibitor of B-Raf and at least one mitochondrial inhibitor in a pharmaceutically acceptable carrier described herein when the melanoma of the subject has at least one mutation in a B-Raf gene therein.

In one embodiment, provided herein is a method for treating melanoma in a subject in need thereof, the method comprising administering to the subject a therapeutically effective amount of a composition comprising at least one inhibitor of B-Raf and at least one mitochondrial inhibitor in a pharmaceutically acceptable carrier described herein.

In one embodiment, provided herein is a method for treating melanoma in a subject in need thereof, the method comprising providing a subject who has been diagnosed with melanoma; analyzing that the melanoma comprises at least one mutation in a B-Raf gene therein, or at least one mutation in a NRAS gene therein, at least one mutation is a NF1 gene, or at least one mutation in a c-KIT gene therein; and if there is at least one mutation in a NRAS gene therein, then administering to the subject a therapeutically effective amount of a composition comprising at least one MEK 1 and/or MEK 2 and/or ERK inhibitor and at least one mitochondrial inhibitor in a pharmaceutically acceptable carrier described herein when the melanoma of the subject has at least one mutation in a NRAS gene therein.

In one embodiment, provided herein is a method for treating melanoma in a subject in need thereof, the method comprising administering to the subject a therapeutically effective amount of a composition comprising at least one MEK 1 and/or MEK 2 and/or ERK inhibitor and at least one mitochondrial inhibitor in a pharmaceutically acceptable carrier described herein.

In one embodiment, provided herein is a method for treating melanoma in a subject in need thereof, the method comprising providing a subject who has been diagnosed with melanoma; analyzing that the melanoma comprises at least one mutation in a B-Raf gene therein, or at least one mutation in a NRAS gene therein, at least one mutation is a NF1 gene, or at least one mutation in a c-KIT gene therein; and if there is at least one mutation in a c-KIT gene therein, then administering to the subject a therapeutically effective amount of a composition comprising at least one c-KIT inhibitor and at least one mitochondrial inhibitor in a pharmaceutically acceptable carrier described herein when the melanoma of the subject has at least one mutation in a c-KIT gene therein.

In one embodiment, provided herein is a method for treating melanoma in a subject in need thereof, the method comprising administering to the subject a therapeutically effective amount of a composition comprising at least one c-KIT inhibitor and at least one mitochondrial inhibitor in a pharmaceutically acceptable carrier described herein.

In one embodiment, the present disclosure provides a method of treating a cancer having activating mutations in the BRAF protein kinase and/or the neuroblastoma RAS oncogene (NRAS). In another embodiment, provides a method of treating a cancer having activating mutations in the c-KIT protein kinase.

BRAF belongs to a family of serine-threonine protein kinases that includes ARAF, BRAF, and CRAF (RAF1). RAF kinases are central mediators in the MAP kinase signaling cascade and exert their effect predominantly through phosphorylation and activation of MEK. This occurs following the dimerization (hetero- or homo-) of the RAF molecules. As part of the MAP kinase pathway, RAF is involved in many cellular processes, including cell proliferation, differentiation, and transcriptional regulation.

Mutant BRAF has been implicated in the pathogenesis of several cancers, including melanoma, non-small cell lung cancer, colorectal cancer, papillary thyroid cancer, and ovarian cancer.

Mutations in BRAF are the most common genetic alterations in melanoma, found in ~50% of tumors (Davies et al., 2002; Curtin et al., 2005). The most frequent BRAF mutation is the substitution of valine at position 600 bp glutamic acid (BRAF V600E) that results in the constitutive activation of its serine/threonine kinase activity and sustained activation of MAP kinase signal transduction pathway (Davies et al., 2002; Wan et al., 2004). BRAF directly phosphorylates the dual-specificity kinases MEK1 and MEK2, which in turn phosphorylate and activate the mitogen-activated protein kinases, ERK1 and ERK2. BRAF has been shown by overexpression and knockdown experiments to be a critical mediator of melanomagenesis. In mice, activation of BRAF in combination with deletion of the tumor suppressor genes PTEN or INK4A leads to melanoma with complete penetrance (Dankort et al., 2009; Dhomen et al., 2009). Conversely, treatment of BRAF mutant melanomas in vitro with chemical inhibitors of BRAF or MEK1/2 promotes cell cycle arrest and apoptosis (Hingorani et al., 2003; Karasarides et al., 2004; Hoeflich, 2006; Wellbrock et al., 2008). Moreover, the BRAF inhibitor vemurafenib (PLX4032) leads to tumor regression and improved overall survival in patients whose melanomas have the BRAF (V600E) mutation, leading to its approval as a treatment for patients with metastatic melanoma (Flaherty et al., 2010; Chapman et al., 2011; Sosman et al., 2012). Despite the promise and dramatic initial effects of BRAF inhibitors in the clinic, patients eventually relapse within several months, suggesting that combination therapies may be needed to overcome intrinsic or acquired resistance (Gray-Schopfer et al., 2007; Poulikakos and Rosen, 2011).

The present inventors have further determined that tigecycline (trade name is TYGACIL®), when administered in combination with one or more other compositions, is useful for treating melanoma in a subject (such as a human patient) in need thereof. For example, the one or more other compositions may be PLX4720.

Specifically, tigecycline is N-[(5aR,6aS,7S,9Z,10aS)-9-[amino(hydroxy)methylidene]-4,7-bis(dimethylamino)-1,10a,12-trihydroxy-8,10,11-trioxo-5,5a,6,6a,7,8,9,10,10a,11-decahydrotetracen-2-yl]-2-(tert-butylamino)acetamide and has the following structure:

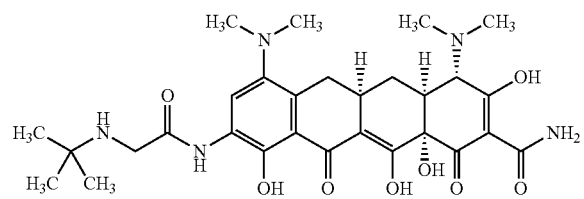 [SMILES: CN(C)c1cc(NC(=O)CNC(C)(C)C)c(O)c2c1C[C@H]1C[C@H]3[C@H](N(C)C)C(O)=C(C(N)=O)C(=O)[C@@]3(O)C(O)=C1C2=O]

It is to be understood, however, that derivatives of tigecycline may be substituted for tigecycline in the aforementioned combination compositions and methods of treating melanoma by using the same. Methods of synthesizing tigecycline and derivatives thereof are well understood in the relevant art.

PLX4720 is N-[3-[(5-Chloro-1H-pyrrolo[2,3-b]pyridin-3-yl)carbonyl]-2,4-difluorophenyl]-1-propanesulfonamide and has the following structure:

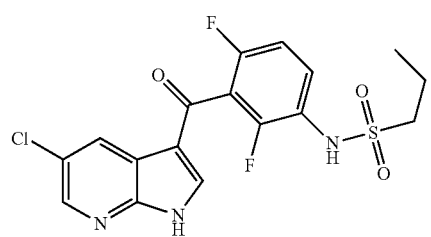 [SMILES: CCCS(=O)(=O)Nc1ccc(F)c(C(=O)c2c[nH]c3ncc(Cl)cc23)c1F]

It is to be understood, however, that derivatives of PLX4720 may be substituted for PLX4720 in the aforementioned combination compositions and methods of treating melanoma by using the same. Methods of synthesizing PLX4720 and derivatives thereof are well understood in the relevant art.

In some embodiments, the B-RAF gene mutation is a substitution of the respective amino acid residue of the encoded B-Raf polypeptide at the following locations:

L597S, L597Q, L597R, V600M, V600K, V600R, V600E, V600G, V600D, V600E, and K601E.

Three different human RAS genes have been identified: KRAS (homologous to the oncogene from the Kirsten rat sarcoma virus), HRAS (homologous to the oncogene from the Harvey rat sarcoma virus), and NRAS (first isolated from a human Neuroblastoma). The different RAS genes are highly homologous but functionally distinct. RAS proteins are small GTPases which cycle between inactive guanosine diphosphate (GDP)-bound and active guanosine triphosphate (GTP)-bound forms. RAS proteins are central mediators downstream of growth factor receptor signaling and therefore are critical for cell proliferation, survival, and differentiation. RAS can activate several downstream effectors, including the PI3K-AKT-mTOR pathway, which is involved in cell survival, and the RAS-RAF-MEK-ERK pathway, which is involved in cell proliferation.

RAS has been implicated in the pathogenesis of several cancers. Activating mutations within the RAS gene result in constitutive activation of the RAS GTPase, even in the absence of growth factor signaling. The result is a sustained proliferation signal within the cell.

Specific RAS genes are recurrently mutated in different malignancies. NRAS mutations are particularly common in melanoma, hepatocellular carcinoma, myeloid leukemias, and thyroid carcinoma Somatic mutations in NRAS have been found in ~13-25% of all malignant melanomas. In the majority of cases, these mutations are missense mutations which introduce an amino acid substitution at positions 12, 13, or 61. The result of these mutations is constitutive activation of NRAS signaling pathways. NRAS mutations are found in all melanoma subtypes, but may be slightly more common in melanomas derived from chronic sun-damaged (CSD) skin. Currently, there are no direct anti-NRAS therapies available.

In the vast majority of cases, NRAS mutations are non-overlapping with other oncogenic mutations found in melanoma (e.g., BRAF mutations, KIT mutations, etc.).

In some embodiments, the NRAS gene mutation is a substitution of the respective amino acid residue of the encoded NRAS polypeptide at the following locations: G12C, G12R, G12S, G12A, G12D, G12V, G13R, G13A, G13D, G13V, Q61E, Q61K, Q61L, Q61P, Q61R, Q61L, Q61R, Q61H and Q61H.

KIT (also called CD 117), is a receptor tyrosine kinase (RTK) expressed on a wide variety of cell types. The ligand for KIT is stem cell factor (SCF). The binding of SCF to the extracellular domain of KIT induces receptor dimerization and activation of downstream signaling pathways, including the PI3K-AKT-mTOR pathway, the RAS-RAF-MEK-ERK pathway, and the STAT3 (Signal Transducer and Activator of Transcription 3) pathway, all of which are involved in mediating pro-growth and pro-survival signals within the cell.

Mutant KIT has been implicated in the pathogenesis of several cancers including melanoma, acute leukemia, and gastrointestinal stromal tumor (GIST).

Somatic mutations in KIT have been found in ~2-6% of all malignant melanoma. KIT mutations may be found in all melanoma subtypes but are the most common in acral melanomas (10-20%) and mucosal melanomas (15-20%). Among mucosal melanomas, KIT mutations are more common in anorectal and vulvo-vaginal primaries (15-25%) than in sinonasal/oropharyngeal tumors (~7%).

Somatic point mutations in melanoma tumor specimens have been detected predominantly in the juxtamembrane domain but also in the kinase domain of KIT. They can induce ligand-independent receptor dimerization, constitutive kinase activity, and transformation. The spectrum of mutations overlaps with those found in gastrointestinal stromal tumor (GIST).

Preclinical studies have shown that KIT mutation within the juxtamembrane domain predicts sensitivity to imatinib, a small molecule inhibitor of KIT, ABL, PDGFRα, and PDGFRβ. In addition, an increasing number of case reports, retrospective, and phase II studies have demonstrated clinical responses of KIT mutated melanoma to imatinib as well as to dasatinib, sunitinib, and sorafenib.

In the majority of cases, KIT mutations are non-overlapping with other oncogenic mutations found in melanoma (e.g., NRAS mutations, BRAF mutations, etc.) (Beadling et al. 2008). In addition, in rare cases the KIT genotype of a primary lesion may differ from its metastases (Terheyden et al. 2010).

In one embodiment, the c-KIT gene mutation is a substitution of the respective amino acid residue of the encoded c-KIT polypeptide at the following locations: W557R, W557R, V559A, V559D, L576P, K642E, and D816H.

Although melanomas with BRAF mutations have constitutively active growth signals, how they sustain their growth in the setting of nutrient scarcity is not well understood. In 1930, Otto Warburg proposed that cancer cells have a high rate of glycolysis as compared to oxidative metabolism even under conditions of high oxygen, a phenomenon known as the Warburg effect (Warburg, 1956; Vander Heiden et al., 2009). Oxidative phosphorylation depends on the ability of functionally intact mitochondria to metabolize oxygen, whereas glycolysis can occur independently of mitochondria. Warburg theorized that this metabolic switch facilitated the uptake and incorporation of nutrients that were required for cellular proliferation. Although poorly understood in melanoma, the molecular mechanisms of metabolic reprogramming in cancer have been described in other tumor types. TP53-deficient tumor cells have diminished levels of the genes TIGAR and SCO2 which regulate glycolysis and assembly of the mitochondrial cytochrome c oxidase complex respectively (Bensaad et al., 2006; Matoba, 2006) Similarly, the dysregulation of the proto-oncogene MYC leads to profound effects on tumor metabolism through multiple mechanisms (reviewed in Dang, 2012). Genomic studies have also identified enzymes involved in the citric acid cycle such as succinate dehydrogenase subunits and fumarate hydratase (FH) as tumor suppressor genes indicating that metabolism impacts tumor growth and progression (Baysal et al., 2000; Niemann and Müller, 2000; Tomlinson et al., 2002; King et al., 2006).

These observations have raised the possibility of targeting key metabolic pathways to inhibit cancer growth. Yun et al. demonstrated that several colorectal cancers with KRAS or BRAF mutations have increased glucose uptake and glycolysis and survived better in low glucose conditions compared to non-mutated cell lines (Yun et al., 2009). Suppression of glycolysis with 3-bromopyruvate (a non-active intermediary in the glycolysis pathway) re-activates mitochondrial metabolism in tumor cells, induces their selective killing and suppresses cancer growth. Similarly, suppression of glycolysis by inhibiting conversion of pyruvate to lactate enhances oxidative phosphorylation and suppressed the growth of breast cancer cell lines (Fantin et al., 2006; Bonnet et al., 2007). Thus, while metabolic reprogramming is commonly found in cancer, the mechanism and details of the metabolic alterations in melanoma are unknown.

Mitochondrial biogenesis and oxidative phosphorylation are well known to be controlled by the members of the peroxisome proliferator-activated receptor γ coactivator 1 (PGC-1) family of transcriptional coactivators (PGC1α, PGC1β, PPRC1) (Lin et al., 2005a; Finck, 2006; Handschin, 2009; Leone and Kelly, 2011). The best-studied PGC-1 family member, PGC1α, potently activates coordinated gene expression programs by interacting with transcription factors, the basal transcriptional machinery, histone-modifying enzymes, and the RNA splicing machinery. PGC1α drives mitochondrial biogenesis in multiple contexts, including brown and white adiocytes (Wu et al., 1999; Uldry et al., 2006), skeletal muscle (Lin et al., 2002) and heart (Lehman et al., 2000). PGC1α mRNA expression is sensitive to numerous signaling inputs that are often implicated in cancer biology, including cAMP and adrenergic signaling (Herzig et al., 2001; Yoon et al., 2001; Chinsomboon et al., 2009) and hypoxia (Arany et al., 2008; Shoag and Arany, 2010). PGC1α protein is also highly regulated by multiple covalent modifications, including acetylation and deacetylation by GCN5 and SIRT1 (Rodgers et al., 2005; Lerin et al., 2006) and phosphorylation by p38 MAPK, AMPK and Akt (Rowe et al., 2010). PGC1β shares significant sequence homology and functional overlap with PGC1α, including the activation of mitochondrial biogenesis and oxidative phosphorylation, but also has several distinct functions in different tissues (Lin et al., 2005b; Uldry et al., 2006; Wolfrum and Stoffel, 2006). The regulation of PGC1β has been less extensively studied. Although little is known about the role of the PGCs in melanoma, they have recently been implicated in metabolic shifts in breast cancer cells and colon cancers (Eichner et al., 2010; Bhalla et al., 2011; Sahin et al., 2011; Wang and Morass, 2011; Girnun, 2012; Klimcakova et al., 2012).

As further disclosed herein, the effect of BRAF pathway activation on gene expression and metabolic effects in melanoma was evaluated. The inventors found that BRAF inhibitors lead to the induction of PGC1α expression through increasing the binding of the melanocyte lineage-specific factor MITF to its promoter. Transcriptional up-regulation of PGC1α by BRAF inhibition is therefore linked with increased oxidative phosphorylation and mitochondrial biogenesis. Furthermore, it was found that BRAF inhibitors lead to increased dependence on mitochondrial metabolism, suggesting that inhibition of mitochondrial metabolism may overcome adaptive resistance.

As an example, in accordance with various embodiments herein, a physician may provide treatment for a melanoma cancer patient by taking a blood sample or biopsy from a patient, and test the sample for the presence or absence of a B-RAF, c-KIT, NF-1 or N-RAS mutation. There are any number of tests or assays available that the physician may use, either as for example an assay that determines the presence (or absence) of the mutation by detecting a genetic variant in the sample, or it may determine the presence (or absence) of an expressed protein or biomarker. If there is a detection of the presence of a B-Raf mutation in the patient, the physician may then administer a specific treatment, such as a B-Raf inhibitor, to the patient. Alternatively, if there is a detection of the presence of an N-Ras mutation for example, the physician may administer a different specific treatment to the patient, such as an MEK inhibitor. The physician may then wait a period of time after treatment, e.g., 5 days, 1 week, 10 days or a month, after which time, the physician can take another blood sample or biopsy from the patient to test the efficacy of the treatment as well as to determine the prognosis of the disease, and then administer another specific treatment to the patient. Similarly, the physician may then wait an additional month after treatment, test for the efficacy of the previous treatment, and then administer an additional appropriate treatment to the patient.

A MEK inhibitor is a chemical or drug that inhibits MEK1 and/or MEK2 which are Mitogen-activated protein kinase enzymes (MAP2K), which is a kinase enzyme which phosphorylates mitogen-activated protein kinase (MAPK). They can be used to affect the MAPK/ERK pathway which is often overactive in some cancers.

Non-limiting examples of a MEK inhibitor are disclosed below:

AZD 6244 (Selumetinib; ARRY-142886) is highly potent to inhibit MEK1 with IC50 of 14 nM. PD0325901 is selective and non ATP-competitive MEK inhibitor with IC50 of 0.33 nM. CI-1040 (PD184352) is an ATP non-competitive MEK1/2 inhibitor with IC50 of 17 nM. U0126-EtOH is a highly selective inhibitor of MEK1 and MEK2 with IC50 of 0.07 µM and 0.06 µM, respectively. PD98059 is a non-ATP competitive MEK inhibitor with IC50 of 2 µM. GSK1120212 (JTP-74057, trametinib) is a highly specific and potent MEK1 and MEK2 inhibitor with IC50 of 0.92 nM and 1.8 nM, respectively. BIX 02189 is a selective inhibitor of MEK5 with IC50 of 1.5 nM. TAK-733 is a potent, selective, non ATP-competitive MEK inhibitor with IC50 of 3.2 nM. Honokiol Honokiol is a biphenolic compound present in the cones, bark, and leaves of *Magnolia grandifloris*. AZD8330 (ARRY-424704) is a MEK 1/2 inhibitor with IC50 of 7 nM. PD318088 is a non-ATP competitive allosteric MEK1/2 inhibitor. BIX 02188 is a selective inhibitor of MEK5 with IC50 of 4.3 nM. AS703026 is a highly selective and potent non-competitive inhibitor of MEK1/2 with IC50 of 5-11 nM. AZD8330 is a MEK inhibitor that specifically inhibits MEK 1. MEK162 (ARRY-438162) and XL518 are additional MEK inhibitors.

As understood by one of skill in the art, any number of MEK inhibitors, chemicals or drugs that inhibit MEK1 and/or MEK2 or affect signaling of the MAPK/ERK pathway are available and may be used with various embodiments described herein and the invention is in no way limited to the specific MEK inhibitors listed. Examples of MEK inhibitors include but are no way limited to trametinib, selumetinib, MEK162, PD-325901, XL518, CI-1040, and PD035901. Similarly, as readily apparent to one of skill in the art, any number of various drugs or compounds may serve as OXPHOS (oxidative phosphorylation) inhibitors and the invention is in no way limited to specific OXPHOS inhibitors listed herein. Example of OXPHOS inhibitors include but in no way limited to oligomycin, malonate, oxaloacetate, barbiturates, rotenone, antimycin-A and arsenate.

Additionally, as apparent to one of skill in the art, any number of mitochondrial inhibitors is readily available and may be used in conjunction with various embodiments herein. There are any numbers of targets that may serve as inhibitors or uncoupling of the energy harnessing process of the mitochondria. Mitochondrial inhibitors may include inhibitors of electron transport, uncoupling oxidative phosphorylation, inhibition of respiratory chain, phosphorylation, ionphores, and inhibitors of Krebs cycle. Mitochondrial inhibitors may include, but are not limited to, hexokinase II inhibitor II, mitochondrial division inhibitor, 3-nitropropionic acid, atractyloside, bongkrekic acid, carbonyl cyanide, carboxyatractyloside, erastin, and ERO1 inhibitor II.

As described herein, an inhibitor of B-Raf (and its gene BRAF) may be used in accordance with various embodiments herein. BRAF, also described as proto-oncogene B-Raf and v-Raf murine sarcoma viral oncogene homolog B1, or the protein also known as serine/threonine-protein kinase B-Raf, is involved in sending signals inside cells for directing cell growth. As apparent to one of skill in the art, various B-Raf inhibitors are readily available and the invention is in no way limited to the B-Raf inhibitors described herein. Some examples of B-Raf inhibitors include, but are in no way limited to, vemurafenib, GDC-0879, PLX-4720, Sorafenib Tosylate, dabrafenib, and LGX818.

In one embodiment, the present disclosure provides a composition comprising one or more inhibitors of B-Raf and one or more mitochondrial inhibitors. In one embodiment, the composition further comprises tigecycline or a derivative thereof.

In one embodiment, the present disclosure provides a composition comprising one or more inhibitors of B-Raf and tigecycline or a derivative thereof. In one embodiment, this composition further comprises one or more mitochondrial inhibitors.

In another embodiment of any composition, the inhibitor of B-Raf inhibits B-Raf kinase activity. In another embodiment of any composition, the inhibitor of B-Raf is a small molecule. In another embodiment of any composition, the inhibitor of B-Raf is vemurafenib, GDC-0879, PLX-4720, Sorafenib Tosylate, Regorafenib, RAF265 and derivatives, NVP-BHG712, AZ628, ZM 336372, SB590885, dabrafenib, and/or LGX818. In another embodiment of any composition, the one or more mitochondrial inhibitor is an inhibitor of oxidative phosphorylation. In another embodiment of any composition, the one or more mitochondrial inhibitors include NV-128, ME-344, TTFA, rotenone, 2,4-Dinitrophenol (DNP), and/or oligomycin A. In another embodiment of any composition, the composition is formulated for topical administration. In another embodiment of any composition, the composition is formulated for transdermal administration. In another embodiment of any composition, the composition is formulated for systemic administration. In another embodiment of any composition, the composition is formulated for localized administration and not for systemic administration.

In one embodiment, the present disclosure provides a method of treating melanoma in a subject by administering a therapeutically effective amount of the composition comprising one or more inhibitors of B-RAF and one or more mitochondrial inhibitors described herein. In one embodiment of the treatment method, this composition further comprises tigecycline or a derivative thereof.

In one embodiment, the present disclosure provides a method of treating melanoma in a subject by administering a therapeutically effective amount of the composition comprising one or more inhibitors of B-RAF and tigecycline or a derivative thereof. In one embodiment of the treatment method, this composition further comprises one or more mitochondrial inhibitors described herein.

In another embodiment of any treatment method, the composition comprises one or more inhibitors of B-RAF and one or more inhibitors of OXPHOS. In another embodiment of any treatment method, the subject has been diagnosed with melanoma. In another embodiment of any treatment method, inhibitors of OXPHOS include oligomycin, malonate, and/or oxaloacetate. In another embodiment of any treatment method, the method further comprises selecting a subject who has been diagnosed with melanoma. In another embodiment of any treatment method, the melanoma includes at least one mutation in the B-RAF gene. In another embodiment of any treatment method, the at least one B-RAF gene mutation is a substitution of valine at the 600 amino acid residue of the encoded B-Raf polypeptide.

In another embodiment of any treatment method, the substitution is selected from the group consisting of V600E, V600D, V600K and V600R. Mutations of BRAF in melanoma are known in the art and they can be found at My Cancer Center Genome period organization at the World Wide Web internet site. In another embodiment of any treatment method, the composition is administered by topical, transdermal or local administration. In another embodiment, the composition is administered systemically.

In another embodiment, the present disclosure provides a method of treating melanoma in a subject by administering a therapeutically effective amount of the composition comprising one or more inhibitors of MEK kinase and one or more mitochondrial inhibitors. In one embodiment of the treatment method, the composition further comprises tigecycline or a derivative thereof.

In another embodiment, the present disclosure provides a method of treating melanoma in a subject by administering a therapeutically effective amount of the composition comprising one or more inhibitors of MEK kinase and tigecycline or a derivative thereof. In one embodiment of the treatment method, the composition further comprises one or more mitochondrial inhibitors.

In another embodiment of any treatment method, the composition comprises one or more inhibitors of MEK kinase inhibitors and one or more OXPHOS (oxidative phosphorylation) inhibitors. In another embodiment of any treatment method, the subject has been diagnosed with melanoma. In another embodiment of any treatment method, the method further comprises selecting a subject who has been diagnosed with melanoma.

In another embodiment of any treatment method, the melanoma includes at least one mutation in the N-RAS gene. In another embodiment of any treatment method, the N-RAS gene mutation is a substitution of glutamine at the 61 amino acid residue of the encoded NRAS polypeptide. In another embodiment of any treatment method, the substitution is selected from the group consisting of NRAS exon 2 mutations Gln61Leu, Gln61Lys, and Gln61Arg. In other embodiments of any treatment method, the NRAS mutation occurs in an amino acid substitution at position 12 in NRAS, from a glycine (G) to one of the following: a cysteine (C), an arginine (R), a serine (S), an alanine (A), an aspartic acid (D) and a valine (V). Mutations of NRAS in melanoma are known in the art and they can be found at My Cancer Center Genome period organization at the World Wide Web internet site.

In another embodiment of any treatment method, the one or more inhibitors of MEK kinase is/are selected from the group consisting of MEK162, trametinib, and selumetinib. In another embodiment of any treatment method, the composition is administered by topical, transdermal or local administration.

In one embodiment, the present disclosure provides a method of treating melanoma in a subject by providing a subject who has been diagnosed with melanoma, analyzing that the melanoma comprises at least one mutation in the B-RAF gene, and administering to the subject a therapeutically effective dosage of a composition comprising one or more inhibitors of B-Raf and one or more mitochondrial inhibitors. In one embodiment of the treatment method, this composition further comprises tigecycline or a derivative thereof.

In one embodiment, the present disclosure provides a method of treating melanoma in a subject by providing a subject who has been diagnosed with melanoma, analyzing that the melanoma comprises at least one mutation in the B-RAF gene, and administering to the subject a therapeutically effective dosage of a composition comprising one or more inhibitors of B-Raf and tigecycline or a derivative thereof. In one embodiment of the treatment method, this composition further comprises one or more mitochondrial inhibitors.

In another embodiment, the present disclosure provides a method of treating melanoma in a subject by providing a subject who has been diagnosed with melanoma, analyzing that the melanoma comprises at least one mutation in the N-RAS gene, and administering to the subject a therapeutically effective dosage of a composition comprising one or more inhibitors of MEK kinase and one or more inhibitors of mitochondrial inhibitors such as an OXPHOS inhibitor. In one embodiment of the treatment method, this composition further comprises tigecycline or a derivative thereof.

In another embodiment, the present disclosure provides a method of treating melanoma in a subject by providing a subject who has been diagnosed with melanoma, analyzing that the melanoma comprises at least one mutation in the N-RAS gene, and administering to the subject a therapeutically effective dosage of a composition comprising one or more inhibitors of MEK kinase and tigecycline or a derivative thereof. In one embodiment of the treatment method, this composition further comprises one or more inhibitors of mitochondrial inhibitors such as an OXPHOS inhibitor.

In another embodiment of any treatment method, the melanoma includes one or more mutations in both the B-RAF gene and N-RAS gene. In another embodiment of any treatment method, the N-RAS gene mutation is a substitution of glutamine at the 61 amino acid residue of the encoded NRAS polypeptide. In another embodiment, the substitution is selected from the group consisting of NRAS exon 2 mutations Gln61Leu, Gln61Lys, and Gln61Arg.

In one embodiment, the present disclosure provides a method of promoting cell death in a cell where a cell is contacted with an effective amount of a composition comprising one or more inhibitors of B-Raf and one or more mitochondrial inhibitors. In one embodiment, the composition further comprises tigecycline or a derivative thereof.

In one embodiment, the present disclosure provides a method of promoting cell death in a cell where a cell is contacted with an effective amount of a composition comprising one or more inhibitors of B-Raf and tigecycline or a derivative thereof. In one embodiment, the composition further comprises one or more mitochondrial inhibitors.

In another embodiment of any method described herein, the cell is a melanoma cell. In another embodiment of any method described herein, the melanoma cell comprises at least one mutation in a B-RAF gene therein. In another embodiment of any method described herein, the at least one B-RAF gene mutation is a substitution of valine at the 600 amino acid residue of the encoded B-Raf polypeptide. In another embodiment of any method described herein, the substitution is selected from the group consisting of V600E, V600D, V600K and V600R. In another embodiment of any method described herein, the cell is contacted with the composition ex vivo, in vitro or in vivo.

In another embodiment, the present disclosure provides a method of promoting cell death in a cell where a cell is contacted with an effective amount of a composition comprising one or more inhibitors of MEK kinase and one or more mitochondrial inhibitors. In one embodiment of the method, the composition further comprises tigecycline or a derivative thereof.

In another embodiment, the present disclosure provides a method of promoting cell death in a cell where a cell is contacted with an effective amount of a composition comprising one or more inhibitors of MEK kinase and tigecycline or a derivative thereof. In one embodiment of the method, the composition further comprises one or more mitochondrial inhibitors.

In another embodiment of any method described herein, the composition comprises one or more inhibitors of MEK kinase and one or more mitochondrial inhibitors. In another embodiment of any method described herein, the one or more inhibitors of MEK kinase is selected from the group consisting of MEK162, trametinib, and selumetinib. In another embodiment of any method described herein, the cell is a melanoma cell. In another embodiment of any method described herein, the melanoma cell comprises at least one mutation in an N-RAS gene. In another embodiment of any method described herein, the N-RAS gene mutation is a substitution of glutamine at the 61 amino acid residue of the encoded NRAS polypeptide. In another embodiment of any method described herein, the substitution is selected from the group consisting of NRAS exon 2 mutations Gln61Leu, Gln61Lys, and Gln61Arg.

In one embodiment, the present disclosure provides a method of promoting cell death in a cell comprising the steps of providing a melanoma cell, analyzing that the melanoma cell comprises at least one mutation in the B-RAF gene therein wherein the at least one B-RAF gene mutation is a substitution of valine at the 600 amino acid residue of the encoded B-Raf polypeptide, and contacting the melanoma cell with an effective amount of a composition comprising one or more inhibitors of B-Raf and one or more mitochondrial inhibitors. In one embodiment of the method, the composition further comprises tigecycline or a derivative thereof.

In one embodiment, the present disclosure provides a method of promoting cell death in a cell comprising the steps of providing a melanoma cell, analyzing that the melanoma cell comprises at least one mutation in the B-RAF gene therein wherein the at least one B-RAF gene mutation is a substitution of valine at the 600 amino acid residue of the encoded B-Raf polypeptide, and contacting the melanoma cell with an effective amount of a composition comprising one or more inhibitors of B-Raf and tigecycline or a derivative thereof. In one embodiment of the method, the composition further comprises one or more mitochondrial inhibitors.

In another embodiment of any method described herein, the substitution is selected from the group consisting of V600E, V600D, V600K and V600R. In another embodiment of any method described herein, the cell is contacted with the composition ex vivo, in vitro or in vivo.

In another embodiment, the present disclosure provides a method of promoting cell death in a cell comprising the steps of providing a melanoma cell, analyzing that the melanoma cell comprises at least one mutation in the N-RAS gene therein, and contacting the melanoma cell with an effective amount of a composition comprising one or more inhibitors of MEK kinase. In one embodiment of the method, this composition further comprises tigecycline or a derivative thereof.

In another embodiment of any method described herein, the N-RAS gene mutation is a substitution of glutamine at the 61 amino acid residue of the encoded NRAS polypeptide. In another embodiment of any method described herein, the substitution is selected from the group consisting of NRAS exon 2 mutations Gln61Leu, Gln61Lys, and Gln61Arg. In another embodiment of any method described herein, the composition comprises one or more inhibitors of MEK kinase and one or more inhibitors of OXPHOS. In another embodiment of any method described herein, the one or more inhibitors of MEK kinase is/are selected from the group consisting of MEK162, trametinib, and selumetinib.

In some embodiments of any methods described, the method further comprises analyzing for at least one mutation is NF-1 gene. Examples of mutations found in the NF-1 gene in melanoma are known in the art and are described in Andersen L. B. et al., Nat Genet. 1993, 3:118-21; and Guillot B, et al., Melanoma Res. 2004, 14:159-63. These references are incorporated by reference in their entirety.

In another embodiment of any method described, the method further comprises selecting a subject who has been diagnosed with melanoma. In another embodiment, the melanoma comprises at least one mutation in the B-RAF gene therein. In another embodiment, the at least one B-RAF gene mutation is a substitution of valine at the 600 amino acid residue of the encoded B-Raf polypeptide. In another embodiment, the substitution is selected from the group consisting of V600E, V600D, V600K and V600R.

In one embodiment, the present disclosure provides a composition comprising at least one inhibitor of B-Raf and at least one mitochondrial inhibitor for use in treating melanoma in a subject in need thereof. In one embodiment, the composition further comprises tigecycline or a derivative thereof.

In one embodiment, the present disclosure provides a composition comprising at least one inhibitor of B-Raf and tigecycline or a derivative thereof for use in treating melanoma in a subject in need thereof. In one embodiment, the composition further comprises at least one mitochondrial inhibitor.

In another embodiment of any composition described, the inhibitor of B-Raf inhibits B-Raf kinase activity. In another embodiment, the inhibitor of B-Raf kinase activity is a small molecule. In another embodiment of any composition described, the small molecule inhibitor is selected from the group consisting of vemurafenib, GDC-0879, PLX-4720, Sorafenib Tosylate, Regorafenib, RAF265 and derivatives, NVP-BHG712, AZ628, ZM 336372, SB590885, dabrafenib, and LGX818. In another embodiment of any composition described, the at least one mitochondrial inhibitor is an inhibitor of oxidative phosphorylation. In another embodiment of any composition described, the mitochondrial inhibitor is selected from the group consisting of NV-128, ME-344, TTFA, rotenone, 2,4-Dinitrophenol (DNP), or oligomycin A. In another embodiment of any composition described, the composition is formulated for topical administration. In another embodiment, the composition is formulated for transdermal administration. In another embodiment of any composition described, the composition is formulated for systemic administration. In another embodiment of any composition described, the composition is formulated for localized administration and not for systemic administration. In another embodiment, the subject has been diagnosed with melanoma.

In one embodiment of any composition described herein, the composition comprises PLX-4720 and tigecycline or a derivative thereof.

In one embodiment of any composition described herein, the composition further comprises at least one pharmaceutically acceptable carrier.

In one embodiment, the present disclosure is a composition comprising at least one inhibitor of B-Raf and at least one mitochondrial inhibitor for the manufacture of medicament for treating melanoma in a subject in need thereof. In one embodiment, the composition further comprises tigecycline or a derivative thereof.

In one embodiment, the present disclosure is a composition comprising at least one inhibitor of B-Raf and tigecycline or a derivative thereof for the manufacture of medicament for treating melanoma in a subject in need thereof. In one embodiment, the composition further comprises at least one mitochondrial inhibitor.

In another embodiment of the composition, the mitochondria inhibitor is 2,4-DNP. In another embodiment, the composition comprises at least one inhibitor of MEK kinase and at least one mitochondrial inhibitor. In another embodiment, the one or more inhibitors of MEK kinase is selected from the group consisting of MEK162, trametinib, and selumetinib. In another embodiment, the composition comprises at least one OXPHOS inhibitor.

In one embodiment, provided herein is a method of selecting a subject having melanoma for a treatment comprising at least one mitochondrial inhibitor comprising: the method comprising (a) providing a subject who has been diagnosed with melanoma; (b) treating the subject for melanoma for a period of time; (c) measuring the expression level of PGC1 alpha and/or MITF in the melanoma; (d) comparing the expression level of PGC1 alpha is step (c) with a reference level, wherein the reference level is the expression level of PGC1 alpha and/or MITF in the melanoma prior to treatment; (e) selecting the subject for an additional treatment if the level of a measured expression level of PGC1 alpha and/or MITF is at least 2-fold increase over that of the reference level; (f) and administering to the subject a therapeutically effective amount of at least one mitochondrial inhibitor. In one embodiment of the treatment method, the method further comprises administering to the subject a therapeutically effective amount of tigecycline or a derivative thereof.

In one embodiment, provided herein is a method for treating melanoma in a subject in need thereof, the method comprising (a) providing a subject who has been diagnosed with melanoma; (b) treating the subject with at least one inhibitor of a MAPK pathway for a period of time; (c) measuring the expression level of PGC1 alpha and/or MITF in the melanoma; (d) comparing the expression level of PGC1 alpha is step c with a reference level, wherein the reference level is the expression level of PGC1 alpha and/or MITF in the melanoma prior to treatment with the at least one inhibitor of a MAPK pathway; (e) selecting the subject for an additional treatment if the level of a measured expression level of PGC1 alpha and/or MITF is at least 2-fold increase over that of the reference level; and (f) administering to the subject a therapeutically effective amount of a mitochondrial inhibitor. In one embodiment of the treatment method, the method further comprises administering to the subject a therapeutically effective amount of tigecycline or a derivative thereof.

In one embodiment, the present disclosure provides a method of treating melanoma in a subject in need thereof, where a subject who has been diagnosed with melanoma is treated with (a) at least one inhibitor of B-Raf, or (b) at least one inhibitor of B-Raf and tigecycline or a derivative thereof, or (c) tigecycline or a derivative thereof for a period of time, measuring the expression level of PGC1 alpha and/or MITF in the melanoma, comparing the expression level of PGC1 alpha and/or MITF with a reference level, selecting the subject for an additional treatment if the level of a measured expression level of PGC1 alpha and/or MITF is increased over that of the reference level, and administering a therapeutically effective amount of a mitochondrial inhibitor. In one embodiment, the reference level is the expression level of PGC1 alpha and/or MITF in the melanoma prior to treatment with the at least one inhibitor of a B-Raf. In another embodiment, the mitochondria inhibitor is 2,4-DNP. In another embodiment, the reference level is the expression level of PGC1 alpha and/or MITF in the melanoma prior to treatment with the at least one inhibitor of B-Raf. In another embodiment, the increase in level of expression level of PGC1 alpha and/or MITF is an at least 2-fold increase over that of the reference level. In another embodiment, the melanoma in the subject comprises at least one mutation in the B-RAF gene therein. In another embodiment, the at least one B-RAF gene mutation is a substitution of valine at the 600 amino acid residue of the encoded B-Raf polypeptide. In another embodiment, the substitution is selected from the group consisting of V600E, V600D, V600K and V600R. In another embodiment, the at least one inhibitor of B-RAF is a small molecule inhibitor. In another embodiment, the small molecule inhibitor is selected from the group consisting of vemurafenib, GDC-0879, PLX-4720, Sorafenib Tosylate, Regorafenib, RAF265 and derivatives, NVP-BHG712, AZ628, ZM 336372, SB590885, dabrafenib, and LGX818. In another embodiment, the at least one mitochondrial inhibitor is an inhibitor of oxidative phosphorylation. In another embodiment, the mitochondrial inhibitor is selected from the group consisting of NV-128, ME-344, TTFA, rotenone, 2,4-Dinitrophenol (DNP), or oligomycin A.

In another embodiment, the present invention provides a method of treating melanoma in a subject in need thereof, where a subject who has been diagnosed with melanoma is treated with (a) at least one inhibitor of MEK kinase, or (b) at least one inhibitor of MEK kinase and tigecycline or a derivative thereof, or (c) tigecycline or a derivative thereof for a period of time, for a period of time, measuring the expression level of PGC1 alpha and/or MITF in the melanoma, comparing the expression level of PGC1 alpha and/or MITF with a reference level, selecting the subject for an additional treatment if the level of a measured expression level of PGC1 alpha and/or MITF is increased over that of the reference level, and administering a therapeutically effective amount of a mitochondrial inhibitor. In another embodiment, the reference level is the expression level of PGC1 alpha and/or MITF in the melanoma prior to treatment with the at least one inhibitor of MEK kinase. In another embodiment, the mitochondria inhibitor is 2,4-DNP.

In another embodiment, the present invention provides a method of treating melanoma in a subject in need thereof, where a subject who has been diagnosed with melanoma is treated with (a) at least one inhibitor of MEK kinase, or or (b) at least one inhibitor of MEK kinase and tigecycline or a derivative thereof, or (c) tigecycline or a derivative thereof for a period of time, measuring the expression level of PGC1 alpha and/or MITF in the melanoma, comparing the expression level of PGC1 alpha and/or MITF with a reference level, selecting the subject for an additional treatment if the level of a measured expression level of PGC1 alpha and/or MITF is increased over that of the reference level, and administering a therapeutically effective amount of a OXPHOS inhibitor. In another embodiment, the reference level is the expression level of PGC1 alpha and/or MITF in the melanoma prior to treatment with the at least one inhibitor of MEK kinase. In another embodiment, the one or more inhibitors of MEK kinase is selected from the group consisting of MEK162, trametinib, and selumetinib. In another embodiment, the increase in level of expression level of PGC1 alpha and/or MITF is an at least 2-fold increase over that of the reference level. In another embodiment, the melanoma in the subject comprises at least one mutation in the N-RAS gene therein. In another embodiment, the N-RAS gene mutation is a substitution of glutamine at the 61 amino acid residue of the encoded NRAS polypeptide. In another embodiment, the substitution is selected from the group consisting of NRAS exon 2 mutations Gln61Leu, Gln61Lys, and Gln61Arg.

In one embodiment, provided herein is a method for treating melanoma in a subject in need thereof, the method comprising (a) providing a subject who has been diagnosed with melanoma; (b) treating the subject with (i) at least one inhibitor of a NRAS, or (ii) at least one inhibitor of a NRAS and tigecycline or a derivative thereof, or (iii) tigecycline or a derivative thereof for a period of time; (c) measuring the expression level of PGC1 alpha and/or MITF in the melanoma; (d) comparing the expression level of PGC1 alpha is step c with a reference level, wherein the reference level is the expression level of PGC1 alpha and/or MITF in the melanoma prior to treatment in step (b); (e) selecting the subject for an additional treatment if the level of a measured expression level of PGC1 alpha and/or MITF is at least 2-fold increase over that of the reference level; and (f) administering to the subject a therapeutically effective amount of a mitochondrial inhibitor.

In one embodiment, provided herein is a method for treating melanoma in a subject in need thereof, the method comprising (a) providing a subject who has been diagnosed with melanoma; (b) treating the subject with (i) at least one inhibitor of a c-KIT, or (ii) at least one inhibitor of a c-KIT and tigecycline or a derivative thereof, or (iii) tigecycline or a derivative thereof for a period of time; (c) measuring the expression level of PGC1 alpha and/or MITF in the melanoma; (d) comparing the expression level of PGC1 alpha is step c with a reference level, wherein the reference level is the expression level of PGC1 alpha and/or MITF in the melanoma prior to treatment in step (b); (e) selecting the subject for an additional treatment if the level of a measured expression level of PGC1 alpha and/or MITF is at least 2-fold increase over that of the reference level; and (f) administering to the subject a therapeutically effective amount of a mitochondrial inhibitor.

In one embodiment of any of the methods described, the subject has been diagnosed with melanoma.

In one embodiment of any of the methods described, the subject is treated with a composition comprising PLX-4720 and tigecycline or a derivative thereof.

In one embodiment of any of the methods described, the subject is treated with PLX-4720 and tigecycline or a derivative thereof.

In one embodiment of any of the methods described, the method further comprises selecting a subject who has been diagnosed with melanoma.

In one embodiment of any of the methods described, the method further comprises selecting a subject is currently being treated for melanoma.

In one embodiment of any of the methods described, the treatment for melanoma comprises administering at least one inhibitor of a MAPK pathway. In other embodiments of any of the methods described, the treatment for melanoma comprises administering at least one MEK 1 and/or MEK2 inhibitor and/or at least one ERK inhibitor. In other embodiments of any of the methods described, the treatment for melanoma comprises administering at least one c-KIT inhibitor. In other embodiments of any of the methods described, the treatment for melanoma comprises administering at least one B-Raf inhibitor.

In one embodiment of any of the method described, the method further comprises analyzing that the melanoma comprises at least one mutation in a B-Raf gene therein, or at least one mutation in a NRAS gene therein, or at least one mutation in a c-KIT gene therein; and if there is at least one mutation in a c-KIT gene therein. In other embodiments of any of the method described, the method further comprises analyzing that the melanoma comprises any mutations in a B-Raf gene, a NRAS gene, and a c-KIT therein.

In one embodiment of any of the method described, the melanoma in the subject comprises at least one mutation in a B-RAF gene therein, or at least one mutation in a NRAS gene therein, or at least one mutation in a c-KIT gene therein.

In one embodiment of any of the method described, the melanoma comprises at least one mutation in the B-RAF gene therein.

In one embodiment of any of the method described, the at least one B-RAF gene mutation is a substitution of valine at the 600 amino acid residue of the encoded B-Raf polypeptide.

In one embodiment of any of the method described, the substitution is selected from the group consisting of V600E, V600D, V600K and V600R.

In one embodiment of any of the method described, the at least one B-RAF gene mutation is a substitution of the respective amino acid residue of the encoded B-Raf polypeptide at the following locations: L597S, L597Q, L597R, V600M, V600K, V600R, V600E, V600G, V600D, V600E, and K601E.

In one embodiment of any of the method described, the at least one c-KIT gene mutation is a substitution of the respective amino acid residue of the encoded c-KIT polypeptide at the following locations: W557R, W557R, V559A, V559D, L576P, K642E, and D816H.

In one embodiment of any of the method described, the at least one NRAS gene mutation is a substitution of the respective amino acid residue of the encoded NRAS polypeptide at the following locations: G12C, G12R, G12S, G12A, G12D, G12V, G13R, G13A, G13D, G13V, Q61E, Q61K, Q61L, Q61P, Q61R, Q61L, Q61R, Q61H and Q61H.

In one embodiment of any of the method described, the period of time after treatment at which the measurement of PGC1 alpha and/or MITF expression is performed is can be anywhere from about 2 days to about one month. In other embodiments, the measurement can be performed anywhere up to 6 months as prophylaxis against the development of drug resistance of the melanoma where prior measurements did not produced an at least two fold increase in expression level. In some embodiments of any of the method described, the period of time can be 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, 35 days, 40 days, 45 days, 50 days, 55 days, 60 days, 65 days, 70 days, 75 days, 80 days, 85 days, 90 days, 95 days, 100 days, 120 days, 150 days, or180 days after a treatment for melanoma. For example, when a subject is newly diagnosed with melanoma, the first treatment is administered and subsequently, a biopsy sample can be taken from the subject for analysis of the PGC1 alpha and/or MITF expression in the biopsy sample. Analysis shortly after treatment commencement and frequent screening for an increase in PGC1 alpha and/or MITF expression is desired at this early phase of treatment in order to detect treatment resistance development early. In one embodiment, an emergence of treatment resistance in melanoma is indicated by an increased in PGC1 alpha and/or MITF expression compared to their respective expression levels prior treatment.

When the first analysis of PGC1 alpha and/or MITF expression level did not show any increase, the analysis can be repeated on a regular basis as long as the subject is undergoing treatment. For example, after the first negative data of PGC1 alpha and/or MITF increased expression, the analysis can be repeated every 5 days thereafter, every week thereafter, every two days thereafter etc. as long as the subject is undergoing treatment. If and when any of the analysis of PGC1 alpha and/or MITF expression level show an increase of at least 2 fold over the reference, the subject would be further administered an effective amount of one or more mitochondria inhibitor described.

In one embodiment, the present invention provides a method of selecting a subject having melanoma for a treatment comprising at least one mitochondrial inhibitor by the following steps: measuring the expression level of PGC1 alpha or MITF in the melanoma, comparing the expression level of PGC1 alpha and/or MITF with a reference level, selecting the subject for an additional treatment if the level of a measured expression level of PGC1 alpha and/or MITF is increased over that of the reference level, and administering to the subject a therapeutically effective amount of a mitochondrial inhibitor. In another embodiment, the mitochondria inhibitor is 2,4-DNP. In another embodiment, the reference level is the expression level of PGC1 alpha and/or MITF in the melanoma prior to treatment with at least one inhibitor of B-Raf. In another embodiment, the reference level is the expression level of PGC1 alpha and/or MITF in the melanoma prior to treatment with at least one MEK kinase inhibitor. In another embodiment, the reference level is the expression level of PGC1 alpha and/or MITF in the melanoma prior to treatment with at least one MAPK pathway inhibitor. In another embodiment, the reference level is the expression level of PGC1 alpha and/or MITF in the melanoma prior to treatment with at least one c-KIT inhibitor. In another embodiment, the one or more inhibitors of MEK kinase is/are selected from the group consisting of MEK162, trametinib, and selumetinib. In another embodiment, the increase in level of expression level of PGC1 alpha and/or MITF is at least a 2-fold increase over that of the reference level.

In one embodiment, the invention provides a method for prognostic evaluation of an individual diagnosed with cancer comprising determining the level of expression of PGC1 alpha, MITF and/or OXPHOS genes in a sample from an individual diagnosed with melanoma, wherein when the level of expression of PGC1 alpha, MITF and/or OXPHOS genes in the sample is higher than a reference PGC1 alpha, MITF and/or OXPHOS gene level, there is an increased likelihood of cancer metastasis and thus a poor prognosis. In another embodiment, the invention provides a method of prognosis evaluation of an individual with melanoma following a first treatment, wherein if after the first treatment the level of expression of PGC1 alpha, MITF and/or OXPHOS genes in the sample is higher than a reference PGC1 alpha MITF and/or OXPHOS gene expression level, a second treatment is administered. In another embodiment, the second treatment includes the administration of a therapeutically effective dosage of a composition comprising at least one mitochondria inhibitor to the individual. The time between administering the first treatment and determining the level of expression of PGC1 alpha, MITF and/or OXPHOS genes may be less than one month. Alternatively, the time between administering the first treatment and determining the level of expression of PGC1 alpha, MITF and/or OXPHOS genes may range between one to two months. In another embodiment, the time between administering the first treatment and determining the level of expression of PGC1 alpha, MITF and/or OXPHOS genes may range between two to three months. In another embodiment, the time between administering the first treatment and determining the level of expression of PGC1 alpha, MITF and/or OXPHOS genes may range between three to four months. In another embodiment, the time between administering the first treatment and determining the level of expression of PGC1 alpha, MITF and/or OXPHOS genes may be four months or more. In other embodiment, a series of samples and measurements of the individual may be taken over one or more months to determine the level of expression of PGC1 alpha, MITF and/or OXPHOS genes before administering a therapeutically effective dosage of mitochondria inhibitor. In another embodiment, the mitochondria inhibitor is 2,4-DNP.

In some embodiments, the changes in (MITF)-PGC1 alpha expression levels can be analyzed and measured directly by qRT-PCR described herein.

In some embodiments, the changes in (MITF)-PGC1 alpha expression levels can be analyzed and measured directly by Western blot analyses of increased protein expression.

In other embodiments, the changes in (MITF)-PGC1 alpha expression levels can be analyzed and measured indirectly by FDG-PET or similar clinical visualization method. There is a correlation between increase expression and changes in metabolic and/or glucose uptake. Fluorodeoxyglucose ($^{18}F$) or fludeoxyglucose ($^{18}F$) (INN), commonly abbreviated $^{18}F$-FDG or FDG, is a radiopharmaceutical used in the medical imaging modality positron emission tomography (PET). Chemically, it is 2-deoxy-2-($^{18}F$)fluoro-D-glucose, a glucose analog, with the positron-emitting radioactive isotope fluorine-18 substituted for the normal hydroxyl group at the 2' position in the glucose molecule. Methods using FDG-PET are known in the art and are described in Simon-Peter Williams et al., EJNMMI Research 2012, 2:35; and Hoeflich K P, et al., Cancer Res 2009, 69:3042-3051. These references are incorporated herein by reference in their entirety.

Compositions for Treatment of Melanoma

In one embodiment, provided herein is a pharmaceutical composition for treating melanoma in a subject in need thereof, the composition comprising at least one inhibitor of a MAPK pathway and at least one mitochondrial inhibitor in a pharmaceutically acceptable carrier.

In one embodiment, provided herein is a composition comprising at least one inhibitor of a MAPK pathway and at least one mitochondrial inhibitor for the manufacture of medicament for treating melanoma in a subject in need thereof.

In one embodiment, provided herein is a composition comprising at least one inhibitor of a MAPK pathway and at least one mitochondrial inhibitor for use in treating melanoma in a subject in need thereof.

In one embodiment of any one of the composition, the at least one inhibitor of a MAPK pathway is an inhibitor of B-Raf, an inhibitor of c-KIT, an inhibitor of MEK 1 or MEK2 or both, or an inhibitor of ERK.

In one embodiment of any one of the composition, the at least one inhibitor of a MAPK pathway is an EGFR inhibitor.

In one embodiment, the at least one mitochondrial inhibitor is an inhibitor of oxidative phosphorylation (OXPHOS inhibitor).

In one embodiment, provided herein is a pharmaceutical composition for treating melanoma in a subject in need thereof, the composition comprising at least one inhibitor of B-Raf and at least one mitochondrial inhibitor in a pharmaceutically acceptable carrier.

In one embodiment, provided herein is a composition comprising at least one inhibitor of B-Raf and at least one mitochondrial inhibitor for the manufacture of medicament for treating melanoma in a subject in need thereof.

In one embodiment, provided herein is a composition comprising at least one inhibitor of B-Raf and at least one mitochondrial inhibitor for use in treating melanoma in a subject in need thereof.

In one embodiment, provided herein is a pharmaceutical composition for treating melanoma in a subject in need thereof, the composition comprising at least one inhibitor of c-KIT and at least one mitochondrial inhibitor in a pharmaceutically acceptable carrier.

In one embodiment, provided herein is a composition comprising at least one inhibitor of c-KIT and at least one mitochondrial inhibitor for the manufacture of medicament for treating melanoma in a subject in need thereof.

In one embodiment, provided herein is a composition comprising at least one inhibitor of c-KIT and at least one mitochondrial inhibitor for use in treating melanoma in a subject in need thereof.

In one embodiment, provided herein is a pharmaceutical composition for treating melanoma in a subject in need thereof, the composition comprising at least one inhibitor of MEK1 and at least one mitochondrial inhibitor in a pharmaceutically acceptable carrier.

In one embodiment, provided herein is a pharmaceutical composition for treating melanoma in a subject in need thereof, the composition comprising at least one inhibitor of MEK 2 and at least one mitochondrial inhibitor in a pharmaceutically acceptable carrier.

In one embodiment, provided herein is a pharmaceutical composition for treating melanoma in a subject in need thereof, the composition comprising at least one inhibitor of MEK1 and MEK2, and at least one mitochondrial inhibitor in a pharmaceutically acceptable carrier.

In one embodiment, provided herein is a composition comprising at least one inhibitor of MEK1 kinase, MEK2 kinase or both MEK1 and MEK 2, and at least one mitochondrial inhibitor for the of medicament for treating melanoma in a subject in need thereof.

In one embodiment, provided herein is a composition comprising at least one inhibitor of MEK1, MEK2 or both MEK1 and MEK 2, and at least one mitochondrial inhibitor for use in treating melanoma in a subject in need thereof.

In one embodiment, provided herein is a pharmaceutical composition for treating melanoma in a subject in need thereof, the composition comprising at least one inhibitor of ERK and at least one mitochondrial inhibitor in a pharmaceutically acceptable carrier.

In one embodiment, provided herein is a composition comprising at least one inhibitor of ERK and at least one mitochondrial inhibitor for the manufacture of medicament for treating melanoma in a subject in need thereof.

In one embodiment, provided herein is a composition comprising at least one inhibitor of ERK and at least one mitochondrial inhibitor for use in treating melanoma in a subject in need thereof.

In one embodiment of any of the compositions described, the composition comprises at least one inhibitor of B-Raf and at least one OXPHOS inhibitor.

In one embodiment of any of the compositions described, the composition comprises at least one inhibitor of B-Raf, at least one MEK kinase inhibitor and at least one OXPHOS inhibitor.

In one embodiment of any of the compositions described, the composition comprises at least one MEK kinase inhibitor and at least one OXPHOS inhibitor.

In one embodiment of any of the compositions described, the composition comprises at least one c-KIT inhibitor and at least one OXPHOS inhibitor.

In one embodiment of any composition described herein, the composition comprises PLX-4720 and tigecycline or a derivative thereof.

In one embodiment of any composition described herein, the composition further comprises tigecycline or a derivative thereof.

In one embodiment of any of the compositions described, the inhibitor of B-Raf inhibits B-Raf kinase activity.

In one embodiment of any of the compositions described, the inhibitor of B-Raf kinase activity is a small molecule.

In some embodiments of the compositions described, the small molecule inhibitor is selected from the group consisting of vemurafenib, GDC-0879, PLX-4720, Sorafenib Tosylate, Regorafenib (BAY 73-4506, Fluoro-Sorafenib), RAF265 (CHIR-265) and derivatives, NVP-BHG712, GW5074, CEP-32496, AZ628, ZM 336372, SB590885, dabrafenib (GSK2118436), and LGX818.

In one embodiment of any of the compositions described, the mitochondrial inhibitor is selected from the group consisting of NV-128, ME-344, TTFA, rotenone, 2,4-Dinitrophenol (DNP), meclizine, and oligomycin A.

In one embodiment of any of the compositions described, the OXPHOS inhibitor is selected from the group consisting of oligomycin, malonate, oxaloacetate, barbiturates, rotenone, antimycin-A and arsenate.

In one embodiment of any of the compositions described, the MEK inhibitor is selected from the group consisting of AZD 6244 (Selumetinib; ARRY-142886), PD0325901, CI-1040 (PD184352), U0126-EtOH, PD98059, GSK1120212 (JTP-74057, trametinib), BIX 02189, TAK-733, honokiol, AZD8330 (ARRY-424704), PD318088, BIX 02188, AS703026, MEK162 (ARRY-438162) and XL518.

In one embodiment of any of the compositions described, the ERK inhibitor is selected from the group consisting of SB203580, BIRB 796 (Doramapimod), SB 202190 (FHPI), LY2228820, VX-702, VX-745, PH-797804, and TAK 715.

In one embodiment of any of the compositions described, the c-KIT inhibitor is selected from the group consisting of imatinib, nilotinib, dasatinib (BMS-354825), sunitinib malate (Sutent), axitinib (AG-013736), XL184 (Cabozantinib), Pazopanib Hydrochloride (GW786034, Votrient, Armala), Dovitinib (TKI258, CHIR-258), Regorafenib (BAY 73-4506, Fluoro-Sorafenib), Masitinib (AB1010), Motesanib Diphosphate (AMG-706), AV-951 (Tivozanib, KRN-951), Vatalanib (PTK787), MP-470 (Amuvatinib), OSI-930, Telatinib (BAY 57-9352), Ki8751, Dovitinib (TK1258, CHIR258) and Pazopanib.

In some embodiment of any of the compositions described, the composition is formulated for topical administration or transdermal administration.

In one embodiment of any of the compositions described, the composition is formulated for localized administration and not for systemic administration.

In one embodiment of any of the compositions described, the composition is formulated for systemic administration.

In one embodiment of the use of any compositions described, the subject has been diagnosed with melanoma.

In one embodiment of the use of any compositions described, the use further comprising selecting a subject who has been diagnosed with melanoma.

In one embodiment of the use of any compositions described, the melanoma in the subject comprises at least one mutation in a B-RAF gene therein, or at least one mutation in a NRAS gene therein, or at least one mutation in a c-KIT gene therein.

In one embodiment of the use of any compositions described, the at least one B-RAF gene mutation is a substitution of valine at the 600 amino acid residue of the encoded B-Raf polypeptide.

In one embodiment of the use of any compositions described, the substitution is selected from the group consisting of V600E, V600D, V600K and V600R.

In one embodiment of the use of any compositions described, the at least one B-RAF gene mutation is a substitution of the respective amino acid residue of the encoded B-Raf polypeptide at the following locations: L597S, L597Q, L597R, V600M, V600K, V600R, V600E, V600G, V600D, V600E, and K601E.

In one embodiment of the use of any compositions described, the at least one c-KIT gene mutation is a substitution of the respective amino acid residue of the encoded c-KIT polypeptide at the following locations: W557R, W557R, V559A, V559D, L576P, K642E, and D816H.

In one embodiment of the use of any compositions described, the at least one NRAS gene mutation is a substitution of the respective amino acid residue of the encoded NRAS polypeptide at the following locations: G12C, G12R, G12S, G12A, G12D, G12V, G13R, G13A, G13D, G13V, Q61E, Q61K, Q61L, Q61P, Q61R, Q61L, Q61R, Q61H and Q61H.

Detection of Gene Mutations

A variety of methods can be used to determine the presence or absence of a mutation or variant allele, such as a B-RAF, c-KIT, a NF-1 or an N-RAS mutation. As an example, enzymatic amplification of nucleic acid from an individual may be used to obtain nucleic acid for subsequent analysis. The presence or absence of a variant allele or haplotype may also be determined directly from the individual's nucleic acid without enzymatic amplification.

Analysis of the nucleic acid from an individual, whether amplified or not, may be performed using any of various techniques. Useful techniques include, without limitation, polymerase chain reaction based analysis, sequence analysis and electrophoretic analysis. As used herein, the term "nucleic acid" means a polynucleotide such as a single or double-stranded DNA or RNA molecule including, for example, genomic DNA, cDNA and mRNA. The term nucleic acid encompasses nucleic acid molecules of both natural and synthetic origin as well as molecules of linear, circular or branched configuration representing either the sense or antisense strand, or both, of a native nucleic acid molecule.

The presence or absence of a variant allele or haplotype may involve amplification of an individual's nucleic acid by the polymerase chain reaction. Use of the polymerase chain reaction for the amplification of nucleic acids is well known in the art (see, for example, Mullis et al. (Eds.), The Polymerase Chain Reaction, Birkhauser, Boston, (1994)).

A TaqmanB allelic discrimination assay available from Applied Biosystems may be useful for determining the presence or absence of a variant allele. In a TaqmanB allelic discrimination assay, a specific, fluorescent, dye-labeled probe for each allele is constructed. The probes contain different fluorescent reporter dyes such as FAM and VICTM to differentiate the amplification of each allele. In addition, each probe has a quencher dye at one end which quenches fluorescence by fluorescence resonant energy transfer (FRET). During PCR, each probe anneals specifically to complementary sequences in the nucleic acid from the individual. The 5' nuclease activity of Taq polymerase is used to cleave only probe that hybridize to the allele. Cleavage separates the reporter dye from the quencher dye, resulting in increased fluorescence by the reporter dye. Thus, the fluorescence signal generated by PCR amplification indicates which alleles are present in the sample. Mismatches between a probe and allele reduce the efficiency of both probe hybridization and cleavage by Taq polymerase, resulting in little to no fluorescent signal. Improved specificity in allelic discrimination assays can be achieved by conjugating a DNA minor grove binder (MGB) group to a DNA probe as described for example, in Kutyavin et al., "3'-minor groove binder-DNA probes increase sequence specificity at PCR extension temperature," Nucleic Acids Research 28:655-661 (2000)). Minor grove binders include, but are not limited to, compounds such as dihydrocyclopyrroloindole tripeptide (DPI).

Sequence analysis also may also be useful for determining the presence or absence of a variant allele or haplotype.

Restriction fragment length polymorphism (RFLP) analysis may also be useful for determining the presence or absence of a particular allele (Jarcho et al. in Dracopoli et al., Current Protocols in Human Genetics pages 2.7.1-2.7.5, John Wiley & Sons, New York; Innis et al., (Ed.), PCR Protocols, San Diego: Academic Press, Inc. (1990)). As used herein, restriction fragment length polymorphism analysis is any method for distinguishing genetic polymorphisms using a restriction enzyme, which is an endonuclease that catalyzes the degradation of nucleic acid and recognizes a specific base sequence, generally a palindrome or inverted repeat. One skilled in the art understands that the use of RFLP analysis depends upon an enzyme that can differentiate two alleles at a polymorphic site.

Allele-specific oligonucleotide hybridization may also be used to detect a disease-predisposing allele or mutation, such as an B-RAF mutation or N-RAS mutation. Allele-specific oligonucleotide hybridization is based on the use of a labeled oligonucleotide probe having a sequence perfectly complementary, for example, to the sequence encompassing a disease-predisposing allele. Under appropriate conditions, the allele-specific probe hybridizes to a nucleic acid containing the disease-predisposing allele but does not hybridize to the one or more other alleles, which have one or more nucleotide mismatches as compared to the probe. If desired, a second allele-specific oligonucleotide probe that matches an alternate allele also can be used. Similarly, the technique of allele-specific oligonucleotide amplification can be used to selectively amplify, for example, a disease-predisposing allele by using an allele-specific oligonucleotide primer that is perfectly complementary to the nucleotide sequence of the disease-predisposing allele but which has one or more mismatches as compared to other alleles (Mullis et al., supra, (1994)). One skilled in the art understands that the one or more nucleotide mismatches that distinguish between the disease-predisposing allele and one or more other alleles are preferably located in the center of an allele-specific oligonucleotide primer to be used in allele-specific oligonucleotide hybridization. In contrast, an allele-specific oligonucleotide primer to be used in PCR amplification preferably contains the one or more nucleotide mismatches that distinguish between the disease-associated and other alleles at the 3' end of the primer.

A heteroduplex mobility assay (HMA) is another well-known assay that may be used to detect a mutation. HMA is useful for detecting the presence of a polymorphic sequence since a DNA duplex carrying a mismatch has reduced mobility in a polyacrylamide gel compared to the mobility of a perfectly base-paired duplex (Delwart et al., Science 262:1257-1261 (1993); White et al., Genomics 12:301-306 (1992)).

The technique of single strand conformational, polymorphism (SSCP) also may be used to detect the presence or absence of a B-RAF mutation or N-RAS mutation, or a SNP and/or a haplotype (see Hayashi, K., Methods Applic. 1:34-38 (1991)). This technique can be used to detect mutations based on difference in the secondary structure of single-strand DNA that produce an altered electrophoretic mobility upon non-denaturing gel electrophoresis. Polymorphic fragments are detected by comparison of the electrophoretic pattern of the test fragment to corresponding standard fragments containing known alleles.

Denaturing gradient gel electrophoresis (DGGE) also may be used to detect a B-RAF mutation or N-RAS mutation, or a SNP and/or a haplotype. In DGGE, double-stranded DNA is electrophoresed in a gel containing an increasing concentration of denaturant; double-stranded fragments made up of mismatched alleles have segments that melt more rapidly, causing such fragments to migrate differently as compared to perfectly complementary sequences (Sheffield et al., "Identifying DNA Polymorphisms by Denaturing Gradient Gel Electrophoresis" in Innis et al., supra, 1990).

Other molecular methods useful for determining the presence or absence of mutations, SNPs, and/or haplotypes are known in the art and useful in the methods of the invention. Other well-known approaches for determining the presence or absence of a SNP and/or a haplotype include automated sequencing and RNAase mismatch techniques (Winter et al., Proc. Natl. Acad. Sci. 82:7575-7579 (1985)). Furthermore, one skilled in the art understands that, where the presence or absence of multiple alleles or haplotype(s) is to be determined, individual alleles can be detected by any combination of molecular methods. See, in general, Birren et al. (Eds.) Genome Analysis: A Laboratory Manual Volume 1 (Analyzing DNA) New York, Cold Spring Harbor Laboratory Press (1997). In addition, one skilled in the art understands that multiple alleles can be detected in individual reactions or in a single reaction (a "multiplex" assay). In view of the above, one skilled in the art realizes that the methods of the present invention for diagnosing or predicting susceptibility to or protection against melanoma or cancer in an individual may be practiced using one or any combination of the well-known assays described above or another art-recognized genetic assay.

After 18F-FDG is injected into a patient, a PET scanner can form images of the distribution of FDG around the body. The images can be assessed by a nuclear medicine physician or radiologist to provide diagnoses of various medical conditions.

Formulation and Application

In one embodiment, the compounds or combination of compounds are delivered in a pharmaceutically acceptable carrier.

In one embodiment, the term "pharmaceutically acceptable" means approved by a regulatory agency of the Federal or a state government or listed in the U.S. Pharmacopeia or other generally recognized pharmacopeia for use in animals, and more particularly in humans. Specifically, it refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations, and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in Remington's Pharmaceutical Sciences, 18th Ed., Gennaro, ed. (Mack Publishing Co., 1990). The formulation should suit the mode of administration. Additional carrier agents, such as liposomes, can be added to the pharmaceutically acceptable carrier.

Therapeutic compositions contain a physiologically tolerable carrier together with at least a compound or combination of compounds as described herein, dissolved or dispersed therein as an active ingredient. In one embodiment, the therapeutic composition is not immunogenic when administered to a mammal or human patient for therapeutic purposes. As used herein, the terms "pharmaceutically acceptable", "physiologically tolerable" and grammatical variations thereof, as they refer to compositions, carriers, diluents and reagents, are used interchangeably and represent that the materials are capable of administration to or upon a mammal without the production of undesirable physiological effects such as nausea, dizziness, gastric upset and the like. A pharmaceutically acceptable carrier will not promote the raising of an immune response to an agent with which it is admixed, unless so desired. The preparation of a pharmacological composition that contains active ingredients dissolved or dispersed therein is well understood in the art and need not be limited based on formulation. Compositions can be prepared as injectable either as liquid solutions or suspensions, however, solid forms suitable for solution, or suspensions; in liquid prior to use can also be prepared. The preparation can also be emulsified or presented as a liposome composition. The compounds or combination of compounds can also be conjugated with lipids, e.g., amphipathic lipids, for stability and delivery purposes. The conjugation bonds are reversible and are broken or dissolved when the compounds or combination of compounds are delivered to target destination. Alternatively, the compounds or combination of compounds described herein can be prepared as a solid or semi-solid or emulsion in suppository, e.g., as microspheres. The microspheres can be inserted as a solid into or targeted to a solid tumor. The compounds or combination of compounds described herein can be mixed with excipients which are pharmaceutically acceptable and compatible with the active ingredient and in amounts suitable for use in the therapeutic methods described herein. Specifically contemplated pharmaceutical compositions are compounds or combination of compounds in a preparation for delivery as described herein above, or in references cited and incorporated herein in that section. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The therapeutic composition comprising the compounds or combination of compounds described herein can include pharmaceutically acceptable salts of the components therein. Pharmaceutically acceptable salts include the acid addition salts (formed with the free amino groups of the polypeptide) that are formed with inorganic acids such as, for example, hydrochloric or phosphoric acids, or such organic acids as acetic, tartaric, mandelic and the like. Salts formed with the free carboxyl groups can also be derived from inorganic bases such as, for example, sodium, potassium, ammonium, calcium or ferric hydroxides, and such organic bases as isopropylamine, trimethylamine, 2-ethylamino ethanol, histidine, procaine and the like. Physiologically tolerable carriers are well known in the art. Exemplary liquid carriers are sterile aqueous solutions that contain no materials in addition to the active ingredients and water, or contain a buffer such as sodium phosphate at physiological pH value, physiological saline or both, such as phosphate-buffered saline. Still further, aqueous carriers can contain more than one buffer salt, as well as salts such as sodium and potassium chlorides, dextrose, polyethylene glycol and other solutes. Liquid compositions can also contain liquid phases in addition to and to the exclusion of water. Exemplary of such additional liquid phases are glycerin, vegetable oils such as cottonseed oil, and water-oil emulsions. The amount of compounds or combination of compounds or composition used in the methods described herein that will be effective in the treatment of a particular disorder or condition will depend on the nature of the disorder or condition, and can be determined by standard clinical techniques.

Routes of administration include, but are not limited to, direct injection, intradermal, intramuscular, intraperitoneal, intravenous, subcutaneous, intrauterine and oral routes. The compounds or combination of compounds or compositions described herein can be administered by any convenient route, for example by infusion, intravenous injection, suppository or bolus injection, by absorption through epithelial or mucocutaneous linings (e.g., oral mucosa, rectal and intestinal mucosa, etc.) and may be administered together with other biologically active agents. Administration can be systemic or local.

Topical administration of a pharmacologically effective amount can utilize transdermal delivery systems well known in the art. An example is a dermal patch. Alternatively the biolistic gene gun method of delivery can be used. The gene gun is a device for injecting cells with genetic information, originally designed for plant transformation. The payload is an elemental particle of a heavy metal coated with plasmid DNA. This technique is often simply referred to as biolistics.

Another instrument that uses biolistics technology is the PDS-1000/He particle delivery system. For example, inhibitor compounds, functional fragments, or variants, expression vector, and/or gene therapy virus can be coated on minute gold particles, and these coated particles are "shot" into biological tissues such as melanoma under high pressure. An example of gene gun-based method is described for DNA based vaccination of cattle by Loehr B I et. al. J. Virol. 2000, 74:6077-86.

The precise dose and formulation to be employed depends upon the potency of the compounds or combination of compounds described herein, and depends on the amounts large enough to produce the desired effect, e.g., a reduction in size and/or growth of the tumors in the subject. The dosage should not be so large as to cause unacceptable adverse side effects. Generally, the dosage will vary with the type compounds or combination of compounds, and with the age, condition, and size of the tumors in the subject are also considered. Dosage and formulation of the compounds or combination of compounds will also depend on the route of administration, and the mass and number of tumors in the subject, and should be decided according to the judgment of the practitioner and each subject's circumstances. Effective doses can be extrapolated from dose-response curves derived from in vitro or animal model test systems.

The dosage can be determined by one of skill in the art and can also be adjusted by the individual physician in the event of any complication. Typically, the dosage ranges from 0.001 mg/kg body weight to 5 g/kg body weight. In some embodiments, the dosage range is from 0.001 mg/kg body weight to 1 g/kg body weight, from 0.001 mg/kg body weight to 0.5 g/kg body weight, from 0.001 mg/kg body weight to 0.1 g/kg body weight, from 0.001 mg/kg body weight to 50 mg/kg body weight, from 0.001 mg/kg body weight to 25 mg/kg body weight, from 0.001 mg/kg body weight to 10 mg/kg body weight, from 0.001 mg/kg body weight to 5 mg/kg body weight, from 0.001 mg/kg body weight to 1 mg/kg body weight, from 0.001 mg/kg body weight to 0.1 mg/kg body weight, from 0.001 mg/kg body weight to 0.005 mg/kg body weight. Alternatively, in some embodiments the dosage range is from 0.1 g/kg body weight to 5 g/kg body weight, from 0.5 g/kg body weight to 5 g/kg body weight, from 1 g/kg body weight to 5 g/kg body weight, from 1.5 g/kg body weight to 5 g/kg body weight, from 2 g/kg body weight to 5 g/kg body weight, from 2.5 g/kg body weight to 5 g/kg body weight, from 3 g/kg body weight to 5 g/kg body weight, from 3.5 g/kg body weight to 5 g/kg body weight, from 4 g/kg body weight to 5 g/kg body weight, from 4.5 g/kg body weight to 5 g/kg body weight, from 4.8 g/kg body weight to 5 g/kg body weight. In one embodiment, the dose range is from 5 g/kg body weight to 30 g/kg body weight. Alternatively, the dose range will be titrated to maintain serum levels between 5 g/mL and 30 g/mL.

Administration of the doses recited above can be repeated for a limited period of time. In some embodiments, the doses are given once a day, or multiple times a day, for example but not limited to three times a day. In one embodiment, the doses recited above are administered daily for several weeks or months. The duration of treatment depends upon the subject's clinical progress and responsiveness to therapy, e.g., shrinkage of tumor sizes. Continuous, relatively low maintenance doses are contemplated after an initial higher therapeutic dose. As exemplary, the compounds or combination of compounds and a pharmaceutically acceptable carrier can be formulated for direct application by injection into the tumor in the subject.

Efficacy testing can be performed during the course of treatment using the methods described herein, e.g., ultrasound, MRI and CT to monitor the shrinkage in size of the cancer lesions in the treated subject. A decrease in size of the cancer lesions or tumors during and after treatment indicates that the treatment is effective in reducing tumor size. Measurements of the degree of severity of a number of symptoms associated with cancerous tumors are also noted prior to the start of a treatment and then at later specific time period after the start of the treatment. A skilled physician will be able to ascertain the tumor sizes and related symptoms by known methods in the art and those described herein.

All patents and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention can be defined in any of the following numbered paragraphs:

[1] A pharmaceutical composition for treating melanoma in a subject in need thereof, the composition comprising at least one inhibitor of B-Raf and at least one mitochondrial inhibitor in a pharmaceutically acceptable carrier.

[2] The composition of paragraph 1, wherein the inhibitor of B-Raf inhibits B-Raf kinase activity.

[3] The composition of paragraphs 1 or 2, wherein the inhibitor of B-Raf kinase activity is a small molecule.

[4] The composition of paragraph 3, wherein the small molecule inhibitor is selected from the group consisting of vemurafenib, GDC-0879, PLX-4720, Sorafenib Tosylate, Regorafenib, RAF265 and derivatives, NVP-BHG712, AZ628, ZM 336372, SB590885, dabrafenib, and LGX818.

[5] The composition of any of paragraphs 1-4, wherein the at least one mitochondrial inhibitor is an inhibitor of oxidative phosphorylation (OXPHOS inhibitor).

[6] The composition of any of paragraphs 1-4, wherein the mitochondrial inhibitor is selected from the group consisting of NV-128, ME-344, TTFA, rotenone, 2,4-Dinitrophenol (DNP), tigecycline or oligomycin A.

[7] The composition of paragraph 5, wherein the OXPHOS inhibitor is selected from the group consisting of oligomycin, malonate, oxaloacetate, barbiturates, rotenone, antimycin-A and arsenate.

[8] The composition of any of paragraphs 1-7 further comprising comprising tigecycline or a derivative thereof.

[9] A composition for treating melanoma in a subject in need thereof, the composition comprising tigecycline or a derivative thereof and at least one inhibitor of B-Raf and/or at least one mitochondrial inhibitor.

[10] The composition of paragraph 9, further comprising a pharmaceutically acceptable carrier.

[11] The composition of paragraph 9 or 10, wherein the inhibitor of B-Raf inhibits B-Raf kinase activity.

[12] The composition of any one of paragraphs 9-11, wherein the inhibitor of B-Raf kinase activity is a small molecule.
[13] The composition of paragraph 12, wherein the small molecule inhibitor is selected from the group consisting of vemurafenib, GDC-0879, PLX-4720, Sorafenib Tosylate, Regorafenib, RAF265 and derivatives, NVP-BHG712, AZ628, ZM 336372, SB590885, dabrafenib, and LGX818.
[14] The composition of any of paragraphs 9-11, wherein the at least one mitochondrial inhibitor is an inhibitor of oxidative phosphorylation (OXPHOS inhibitor).
[15] The composition of any of paragraphs 9-11, wherein the mitochondrial inhibitor is selected from the group consisting of NV-128, ME-344, TTFA, rotenone, 2,4-Dinitrophenol (DNP), or oligomycin A.
[16] The composition of paragraph 14, wherein the OXPHOS inhibitor is selected from the group consisting of oligomycin, malonate, oxaloacetate, barbiturates, rotenone, antimycin-A and arsenate.
[17] The composition of any of paragraphs 1-16, wherein the composition is formulated for topical administration.
[18] The composition of any of paragraphs 1-16, wherein the composition is formulated for transdermal administration.
[19] The composition of any of paragraphs 1-16, wherein the composition is formulated for localized administration and not for systemic administration.
[20] A method for treating melanoma in a subject in need thereof, the method comprising administering to the subject a therapeutically effective amount of a composition of any one of paragraphs 1-19.
[21] The method of paragraph 20, wherein the subject has been diagnosed with melanoma.
[22] The method of paragraph 20 or 21, further comprising selecting a subject who has been diagnosed with melanoma.
[23] The method of any one of paragraphs 20-22, wherein the melanoma comprises at least one mutation in the B-RAF gene therein.
[24] The method of paragraph 23, wherein the at least one B-RAF gene mutation is a substitution of valine at the 600 amino acid residue of the encoded B-Raf polypeptide.
[25] The method of paragraph 24, wherein the substitution is selected from the group consisting of V600E, V600D, V600K and V600R.
[26] The method of any one of paragraphs 20-25, wherein the composition is administered by topical, transdermal or local administration.
[27] A method for treating melanoma in a subject in need thereof, the method comprising providing a subject who has been diagnosed with melanoma; analyzing that the melanoma comprises at least one mutation in the B-RAF gene therein, wherein the at least one B-RAF gene mutation is a substitution of valine at the 600 amino acid residue of the encoded B-Raf polypeptide; and administering to the subject a therapeutically effective amount of a composition of any one of paragraphs 1-19.
[28] The method of paragraph 27, wherein the substitution is selected from the group consisting of V600E, V600D, V600K and V600R.
[29] The method of paragraph 28, wherein the composition is administered by topical, transdermal or local administration.
[30] The method of any one of paragraphs 20-29, wherein the subject is a human.
[31] A method for promoting cell death in a cell, the method comprising the step of contacting a cell with an effective amount of a composition of any one of paragraphs 1-19.
[32] The method of paragraph 31, wherein the cell is a melanoma cell.
[33] The method of paragraph 32, wherein the melanoma cell comprises at least one mutation in a B-RAF gene therein.
[34] The method of paragraph 33, wherein the at least one B-RAF gene mutation is a substitution of valine at the 600 amino acid residue of the encoded B-Raf polypeptide.
[35] The method of paragraph 34, wherein the substitution is selected from the group consisting of V600E, V600D, V600K and V600R.
[36] The method of any one of paragraphs 31-35, wherein the cell is contacted with the composition ex vivo, in vitro or in vivo.
[37] A method for promoting cell death and/or suppression of cell growth in a cell, the method comprising the step of providing a melanoma cell; analyzing that the melanoma cell comprises at least one mutation in the B-RAF gene therein, wherein the at least one B-RAF gene mutation is a substitution of valine at the 600 amino acid residue of the encoded B-Raf polypeptide; and contacting the melanoma cell with an effective amount of a composition of any one of paragraphs 1-19.
[38] The method of paragraph 37, wherein the substitution is selected from the group consisting of V600E, V600D, V600K and V600R.
[39] The method of paragraph 37 or 38, wherein the cell is contacted with the composition ex vivo, in vitro or in vivo.
[40] A composition comprising at least one inhibitor of B-Raf and at least one mitochondrial inhibitor for use in treating melanoma in a subject in need thereof.
[41] A composition comprising (a) tigecycline or a derivative thereof; and (b) at least one inhibitor of B-Raf and/or at least one mitochondrial inhibitor for use in treating melanoma in a subject in need thereof.
[42] The use of paragraph 40 or 41, wherein the inhibitor of B-Raf inhibits B-Raf kinase activity.
[43] The use of paragraphs 40 or 41 or 42, wherein the inhibitor of B-Raf kinase activity is a small molecule.
[44] The use of paragraph 43, wherein the small molecule inhibitor is selected from the group consisting of vemurafenib, GDC-0879, PLX-4720, Sorafenib Tosylate, Regorafenib, RAF265 and derivatives, NVP-BHG712, AZ628, ZM 336372, SB590885, dabrafenib, and LGX818.
[45] The use of any of paragraphs 40-44, wherein the at least one mitochondrial inhibitor is an inhibitor of oxidative phosphorylation (OXPHOS inhibitor).
[46] The use of any one of paragraphs 40-45, wherein the mitochondrial inhibitor is selected from the group consisting of NV-128, ME-344, TTFA, rotenone, 2,4-Dinitrophenol (DNP) and oligomycin A.
[47] The use of paragraph 45, wherein the OXPHOS inhibitor is selected from the group consisting of oligomycin, malonate, oxaloacetate, barbiturates, rotenone, antimycin-A and arsenate.

[48] The use of any of paragraphs 40-47, wherein the composition further comprises comprising tigecycline or a derivative thereof.

[49] The use of any of paragraphs 40-48, wherein the composition is formulated for topical administration.

[50] The use of any of paragraphs 40-48, wherein the composition is formulated for transdermal administration.

[51] The use of any of paragraphs 40-48, wherein the composition is formulated for localized administration and not for systemic administration.

[52] The use of any of paragraphs 40-51, wherein the subject has been diagnosed with melanoma.

[53] The use of any of paragraphs 40-52, further comprising selecting a subject who has been diagnosed with melanoma.

[54] The use of any one of paragraphs 40-53, wherein the melanoma comprises at least one mutation in the B-RAF gene therein.

[55] The use of paragraph 54, wherein the at least one B-RAF gene mutation is a substitution of valine at the 600 amino acid residue of the encoded B-Raf polypeptide.

[56] The use of paragraph 55, wherein the substitution is selected from the group consisting of V600E, V600D, V600K and V600R.

[57] A composition comprising at least one inhibitor of B-Raf and at least one mitochondrial inhibitor for the manufacture of medicament for treating melanoma in a subject in need thereof.

[58] A composition comprising (a) tigecycline or a derivative thereof; and (b) at least one inhibitor of B-Raf and/or at least one mitochondrial inhibitor for the manufacture of medicament for treating melanoma in a subject in need thereof.

[59] A method for treating melanoma in a subject in need thereof, the method comprising providing a subject who has been diagnosed with melanoma; treating the subject with at least one inhibitor of B-Raf for a period of time; measuring the expression level of PGC1 alpha in the melanoma; comparing the expression level of PGC1 alpha is step c with a reference level, wherein the reference level is the expression level of PGC1 alpha in the melanoma prior to treatment with the at least one inhibitor of B-Raf; selecting the subject for an additional treatment if the level of a measured expression level of PGC1 alpha is at least 2-fold increase over that of the reference level; and administering to the subject a therapeutically effective amount of a mitochondrial inhibitor.

[60] A method for treating melanoma in a subject in need thereof, the method comprising providing a subject who has been diagnosed with melanoma; treating the subject with an effective amount of tigecycline for a period of time; measuring the expression level of PGC1 alpha in the melanoma; comparing the expression level of PGC1 alpha is step c with a reference level, wherein the reference level is the expression level of PGC1 alpha in the melanoma prior to treatment with tigecycline; selecting the subject for an additional treatment if the level of a measured expression level of PGC1 alpha is at least 2-fold increase over that of the reference level; and administering to the subject a therapeutically effective amount of a mitochondrial inhibitor.

[61] The method of paragraph 60, further comprises administering to the subject a therapeutically effective amount of at least one inhibitor of B-Raf.

[62] A method for treating melanoma in a subject in need thereof, the method comprising providing a subject who has been diagnosed with melanoma; treating the subject with an effective amount of tigecycline and at least one inhibitor of B-Raf for a period of time; measuring the expression level of PGC1 alpha in the melanoma; comparing the expression level of PGC1 alpha is step c with a reference level, wherein the reference level is the expression level of PGC1 alpha in the melanoma prior to treatment with tigecycline and at least one inhibitor of B-Raf; selecting the subject for an additional treatment if the level of a measured expression level of PGC1 alpha is at least 2-fold increase over that of the reference level; and administering to the subject a therapeutically effective amount of a mitochondrial inhibitor.

[63] The method of any one of paragraphs 59-62, wherein the melanoma in the subject comprises at least one mutation in the B-RAF gene therein.

[64] The method of paragraph 63, wherein the at least one B-RAF gene mutation is a substitution of valine at the 600 amino acid residue of the encoded B-Raf polypeptide.

[65] The method of paragraph 64, wherein the substitution is selected from the group consisting of V600E, V600D, V600K and V600R.

[66] The method of any one of paragraphs 59-65, wherein the at least one inhibitor of B-RAF is a small molecule inhibitor.

[67] The method of paragraph 66, wherein the small molecule inhibitor is selected from the group consisting of vemurafenib, GDC-0879, PLX-4720, Sorafenib Tosylate, Regorafenib, RAF265 and derivatives, NVP-BHG712, AZ628, ZM 336372, SB590885, dabrafenib, and LGX818.

[68] The method of any of paragraphs 59-67, wherein the at least one mitochondrial inhibitor is an inhibitor of oxidative phosphorylation (OXPHOS inhibitor).

[69] The method of any one of paragraphs 59-68, wherein the mitochondrial inhibitor is selected from the group consisting of NV-128, ME-344, TTFA, rotenone, 2,4-Dinitrophenol (DNP), or oligomycin A.

[70] The method of paragraph 69, wherein the OXPHOS inhibitor is selected from the group consisting of oligomycin, malonate, oxaloacetate, barbiturates, rotenone, antimycin-A and arsenate.

[71] A method for treating melanoma in a subject in need thereof, the method comprising providing a subject who has been diagnosed with melanoma; treating the subject for the melanoma for a period of time; measuring the expression level of PGC1 alpha in the melanoma; comparing the expression level of PGC1 alpha is step c with a reference level, wherein the reference level is the expression level of PGC1 alpha in the melanoma prior to treatment; selecting the subject for an additional treatment if the level of a measured expression level of PGC1 alpha is at least 2-fold increase over that of the reference level; and administering to the subject a therapeutically effective amount of a mitochondrial inhibitor.

[72] The method of paragraph 71, wherein the melanoma is an activated mutation melanoma.

[73] The method of paragraph 72, wherein the activated mutation melanoma has a mutation in either the BRAF or NRAS gene.

[74] The method of any one of paragraphs 71-73, wherein the treatment comprises one or more BRaf inhibitors or one or more MEK inhibitors or both.

[75] The method of any one of paragraphs 59-74, wherein the period of time after treatment at which PGC1 alpha analysis is performed is about 5 days to about one month.

[76] A method of selecting a subject having melanoma for a treatment comprising at least one mitochondrial inhibitor comprising: measuring the expression level of PGC1 alpha in the melanoma; comparing the expression level of PGC1 alpha is step c with a reference level, wherein the reference level is the expression level of PGC1 alpha in the melanoma prior to treatment with the at least one inhibitor of B-Raf; selecting the subject for an additional treatment if the level of a measured expression level of PGC1 alpha is at least 2-fold increase over that of the reference level; and administering to the subject a therapeutically effective amount of a mitochondrial inhibitor.

This invention is further illustrated by the following example which should not be construed as limiting. The contents of all references cited throughout this application, as well as the figures and table are incorporated herein by reference.

Those skilled in the art will recognize, or be able to ascertain using not more than routine experimentation, many equivalents to the specific embodiments of the invention described herein. Such equivalents are intended to be encompassed by the following claims.

EXAMPLE

Materials and Methods
Gene Expression and Bioinformatics

Immortal melanocytes (pmel*) and their transformed counterparts, pmel*BRAF(V600E)-vector and pmel*BRAF(V600E)+MITF were routinely maintained as described previously (Garraway et al., 2005).

For the measurement of specific gene expression differences attributed to BRAF(V600E) expression, the pmel* and pmel* BRAF(V600E) cells were switched to the identical media conditions (DMEM with 10% fetal bovine serum) for 16 hours prior to RNA harvest and qPCR analysis.

The gene expression datasets have been submitted to the GEO repository under accession GSE38007. Gene profiles were analyzed by GenePattern, genomic analysis platform (Broad Institute of Harvard and MIT) or dChip. PGC1α mRNA expression was compared to the expression of all known and sequence-predicted human transcription factors (Medical Research Council United kingdom, DBD: Transcription factor prediction database) by Pearson correlation analysis using the GeneNeighbors module of Gene Pattern. Gene set enrichment analysis was performed using GSEA module of GenePattern. Publically available datasets used in this paper were: GSE20051 (PLX4032 treated melanomas), GSE10086 (PD0325901 treated cell lines), and MALME3M cells treated with shMITF (Li et al., 2012).

Global gene expression analysis was carried out using HG-U133A microarrays (Affymetrix). Affymetrix HT-HGU133A gene expression data for 88 melanoma samples and five normal melanocytes were obtained from the Broad Melanoma Portal (The Broad Institute, melanoma Data Base). The data were normalized using RMA (Irizarry et al., 2003) and the latest mapping of probes to RefSeq genes (Dai et al., 2005). PGC1α-responsive genes and oxidative phosphorylation gene sets were obtained from (Mootha et al., 2003). RefSeq genes corresponding to different isoforms of the same gene and having identical expression values were merged. The k-means algorithm was then used to separate the melanoma samples into two classes based on the expression indices of either the PGC1α gene set or the oxidative phosphorylation gene set. 100 random starts with 1000 maximum iterations were used to find the optimal clustering in each case. T-tests were performed the on the two classes in each clustering analysis. GSEA statistics of oxidative phosphorylation in engineered melanomas was assessed by 7000 iterations of the gene set permutations.

For the measurement of specific gene expression differences attributed to BRAF(V600E) expression, the pmel* and pmel* BRAF(V600E) cells were switched to the identical media conditions (DMEM with 10% fetal bovine serum) for 16 hours prior to RNA harvest and qPCR analysis.

Biochemicals

PLX4072 was obtained from Sai Advantium Pharma Limited (Pune, India). AZD6244 and PLX4032 were obtained from Selleck Chemicals (Houston, Tex.).

Western Blotting and Immunohistochemistry and Biopsies

Whole cell lysates were prepared in lysis buffer supplemented with protease and phosphatase inhibitors (Roche). Equal amounts of protein were resolved by electrophoresis on gradient gels (Bio-Rad).

Antibodies used were as follows: MITF (C5 hybridoma); PGC1α (Calbiochem); α-tubulin (clone DM1A, Sigma); GAPDH, phospho-ERK1/2, and ERK1/2 (Cell Signaling Technology). Melanoma biopsies prior and during treatment were sectioned, embedded in paraffin and stained with the phospho-ERK1/2 antibody (Cell Signaling Technology). PLX4720 was used at 1 μM concentration in all assays, whereas control samples were treated with an equal volume of DMSO.

Evaluation of Gene Expression in Patient Biopsies

Biopsies where obtained from patients with metastatic melanoma with the BRAF(V600E) mutation enrolled in clinical trials for treatment with a BRAF inhibitor or a combination of a BRAF inhibitor and a MEK inhibitor. Biopsies of tumor material consisted of discarded tissue obtained with informed consent as described (Johannessen et al., 2010). Treated samples were collected 10-14 days after initiation of vemurafenib treatment. Formalin-fixed tissue was analyzed by haematoxylin and eosin staining. Sequences of primers used for PCR are listed below.

RNA Isolation, Chromatin Immunoprecipitation and Quantitative Real-Time PCR (qtPCR)

Total RNA was isolated using RNEASY® RNA kits (QIAGEN®) and quantitative real-time PCR was performed on an Applied Biosystems 7700 machine.

Chromatin immunoprecipitation (ChIP) was performed in primary human melanocytes using previously described methods (Cui et al., 2007). Chromatin was immunoprecipitated using rabbit anti-MITF (polyclonal), or normal rabbit IgG (Santa Cruz) as a control. Results are normalized to input DNA.

Clinical Samples

Biopsies where obtained from patients with metastatic melanoma with the BRAF(V600E) mutation enrolled in clinical trials for treatment with a BRAF inhibitor or a combination of a RAF inhibitor and a MEK inhibitor. All patients gave informed consent for tissue acquisition as per an IRB-approved protocol (Office for Human Research Studies, Dana-Farber/Harvard Cancer Center). Tumors were biopsied before treatment (day 0), at 10-14 days during treatment and at the time of progression. Formalin-fixed tissue was analyzed by haematoxylin and eosin staining.

siRNA Delivery and Analysis siRNAs SMARTpools for MITF (M-008674-00-005), PPARGC1A (L-005111-00-0010), TFEB (L-009798-00) or TFE3 (L-009363-00-0005) or control (D-001810-10-05) were from Dharmacon. siRNAs SMARTpools (Dharmacon) were delivered into melanomas or primary melanocytes using the lipidoid delivery agent C12-133-B (Akinc et al., 2008) as described in herein and (Li et al., 2012). shRNAs targeting MITF or non-template control were from the RNAi Consortium (Broad Institute, Cambridge, Mass. USA). GFP and MITF were respectively cloned into the pCW45 lentiviral expression vector (Dana-Farber/Harvard Cancer Center DNA Resource Core). Lentivirus was prepared by transfection of packaging constructs and lentivirus plasmid in 293T cells per standard protocols (The RNAi Consortium, The Broad Institute). Amount of virus was titrated for near quantitative infection with <5% toxicity of non-template virus.

Promoter Assays and Luciferase Experiments

The murine PGC1α promoter was obtained from ADDGENE. Mutagenesis was performed using the QUICK-CHANGE® mutagenesis kit (STRATAGENE®) using primer sequences shown in Table 2. Mutant promoters were verified by sequencing. UACC-62 cells were transfected with each promoter construct, pRL-CMV Renilla control and a M-MITF overexpression vector. PLX4720 treatment was for 48 h. Results reported are averages of at least three independent experiments, normalized for transfection efficiency using Renilla luciferase.

Cell Viability, Metabolic Assays and Flow Cytometry

Cell number was calculated using the CYQUANT® assay (INVITROGEN™) or crystal violet staining. Lactate measurements were done using the Lactate Assay (BioVision or SIGMA®) per manufacturer's protocols. Indicated cell lines were plated in complete media overnight. Media was changed to serum free-media to avoid interference with the assay for 16 h with either PLX4720 (3 µM) or PLX4032 (1 µM) or vehicle control prior to harvesting cells and measurement of lactate. Results were normalized to cell number. All assays were performed in logarithmically growing cells.

MITOTRACKER® Red, Green and MITOSOX™ were obtained from INVITROGEN™ using manufacturer's recommended protocols. Mean fluorescence was determined by FlowJo software and normalized to vehicle-treated cells.

Glucose uptake (relative to total cell numbers) was measured over 24 h as trace [$^3$H]-deoxyglucose uptake in cells growing in glucose-containing media followed by plate harvest and subsequent analysis on a PerkinElmer® Wallac 1450 Microbeta scintillation counter. Oxygen consumption was measured using XF Flux Analyzer (Seahorse Biosciences) using standard protocols. ATP measurements were conducted using ENLITEN® ATP assay (PROMEGA®) according to standard trichloroacetic acid (TCA) extraction protocols.

Xenograft Tumor Studies

All mouse experiments (tumor nucleation studies and longitudinal drug treatment) were done in accordance with Institutional Animal Care and Use Committee (IACUC) approved animal protocols at Dana-Farber Cancer Institute. Engineered melanoma cells with BRAF(V600E)+vector or +MITF were inoculated subcutaneously at three flank positions (100,000 cells in 100 µL PBS per site) in NCR-FoxNu (male, 6 weeks) animals. Tumor establishment was monitored and experiment was terminated after 10 weeks. For longitudinal tumor treatment studies, melanoma cell lines (A375P and UACC257, both carrying pFUW-mCherry-puro-LUC) were injected subcutaneously into NCR-FoxNu mice (5,000,000 cells in 100 µL PBS with growth factor reduced matrigel). Initial tumor establishment and growth visualized by in vivo imaging by comparing signal obtained seven (7) days apart. Treatment was started after tumors reached mean tumor volume of 100 mm$^3$. Treatment with vemurafenib (75 mg/kg/day) or 2,4-DNP (20 mg/kg/day) was administered by oral gavage in 0.5% methyl cellulose and tumor size measured by calipers twice weekly. Mean response measured based on cohorts of 6-7 mice for each arm (and each cell line).

Electron Microscopy

Electron microscopy of UACC-62 melanoma cells treated with vehicle or PLX4720 (3 µM, 72 hrs) was performed at Massachusetts General Hospital's PMB Microscopy Core.

Cells were fixed for 1 hr at room temp in 2.0% glutaraldehyde in 0.1 M sodium cacodylate buffer, pH 7.4 (Electron Microscopy Sciences, Hatfield, Pa.). Cells were rinsed in buffer, scraped and pelleted. The pellets were treated with 1.0% osmium tetroxide (EMS) in cacodylate buffer for 1 hr at room temp. They were rinsed and then resuspended in 2.0% agarose for ease of handling. Small pieces were dehydrated through a graded series of ethanol, then infiltrated with eponate resin (Ted Pella, Redding, Calif.) overnight at room temp. They were then embedded in resin overnight at 60° C. Thin sections were cut on a Leica UC6 ultramicrotome, collected onto formvar-carbon coated slot grids and post-stained with uranyl acetate and lead citrate. They were examined in a JEOL 1011 TEM at 80 kV. Images were collected with an AMT digital imaging system (Advanced Microscopy Techniques, Danvers, Mass.). Mitochondrial density was calculated by morphometrics by standard protocols.

Microarray Data

Expression array data are deposited under GEO accession GSE38007.

Results

BRAF Regulates Metabolic Reprogramming of Melanomas

Figure 9A:
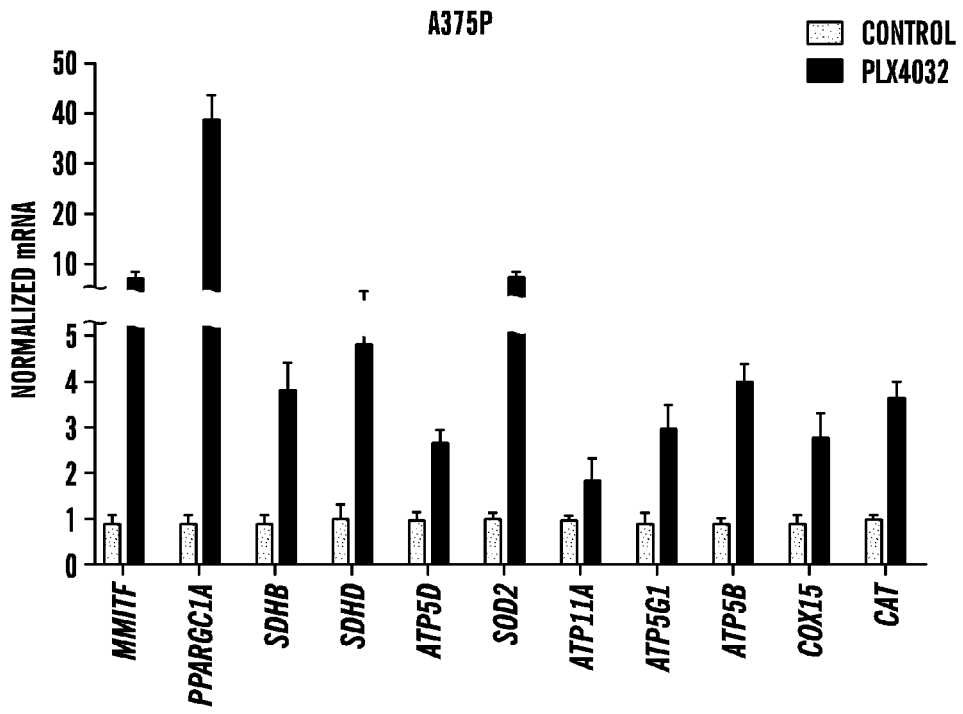
FIGS. 9A-9C show the induction of OXPHOS genes upon treatment with BRAF inhibitors. Indicated mRNAs were quantified by quantitative PCR 24 h after PLX4032 (1 μM) treatment.
Figure 9B:
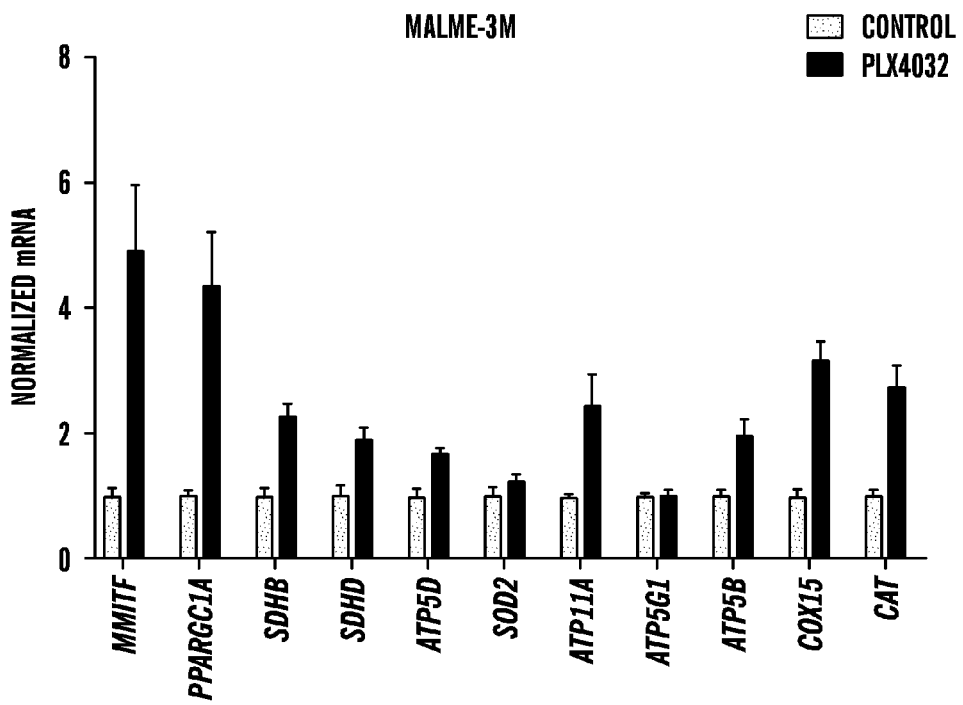
Figure 9C:
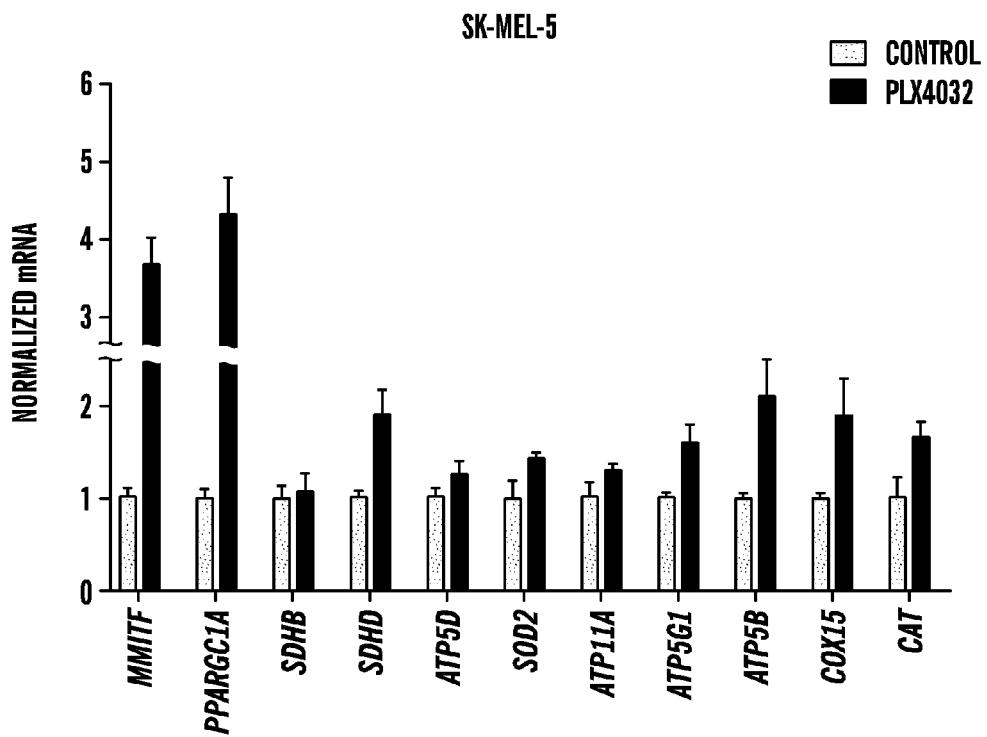

The mechanisms by which oncogenic BRAF promotes oncogenesis are incompletely understood. Gene Set Enrichment Analysis (GSEA) provides a bioinformatics approach to identify gene signatures among microarray datasets that are induced or suppressed as small coordinated changes in individual genes (Mootha et al., 2003). In order to identify gene expression programs altered by oncogenic BRAF, the previously published gene expression profiles of BRAF mutant melanomas treated with the BRAF inhibitor vemurafenib (Joseph et al., 2010) was therefore evaluated. As shown in FIG. 1A, treatment of BRAF mutant melanomas with vemurafenib (aka PLX4032) resulted in significant increases in the expression the citric acid cycle gene set (FIG. 1A) as well as multiple oxidative phosphorylation and ATP synthesis gene sets (Table 1). Similarly, melanoma cells treated with PD0325901, a pre-clinical inhibitor of the MEK1/2 protein kinases (Pratilas et al., 2009; Joseph et al., 2010) also exhibited a trend towards induction of the citric acid cycle and oxidative phosphorylation gene sets (Table 1). In contrast, no enrichment of oxidative phosphorylation, or citric acid cycle gene sets in BRAF-mutant non-melanomas treated with PD0325901 (Table 1) was found. The effects of vemurafenib on OXPHOS gene expression in three melanoma cell lines were validated by quantitative PCR (FIGS. 9A-9C).

Figure 1G:
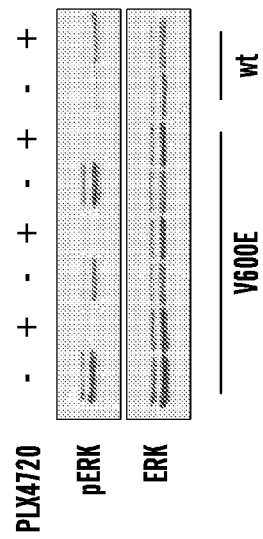
FIG. 1G are representative Western blots showing activated ERK activity in cells of FIG. 1f using phospho-ERK antibodies.
Figure 1E:
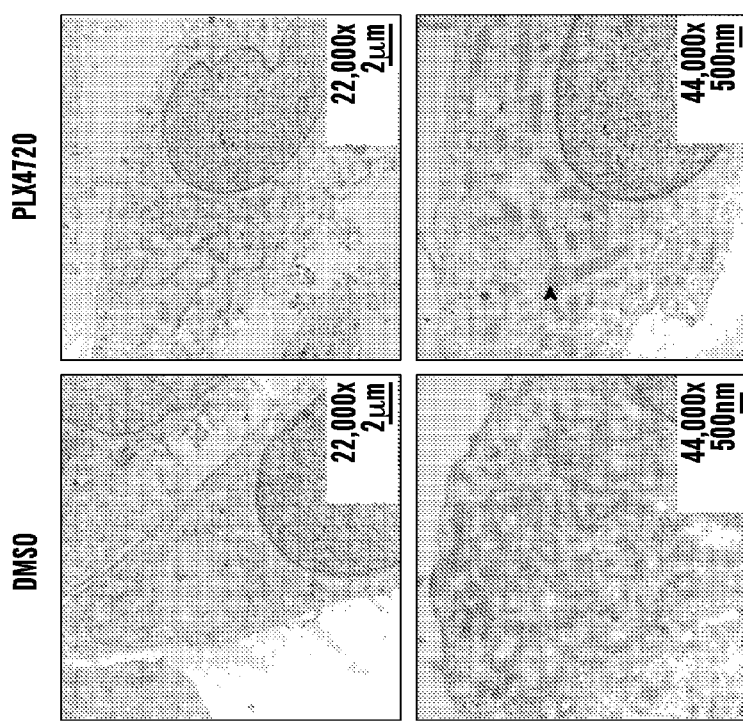
Figure 9D:
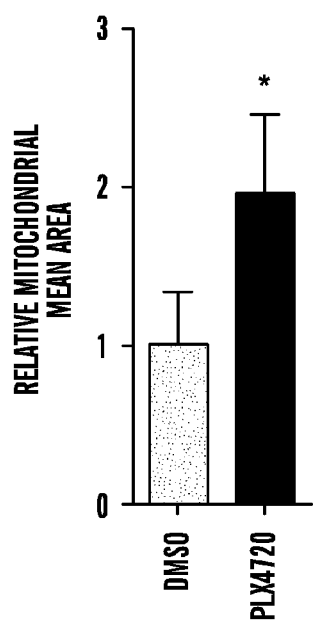
FIG. 9D are histograms showing the mitochondrial mean in UACC-62 cells treated with PLX4720 for 72 hrs. *, $p<0.05$ compared to control treated cells. Error bars represent SEM of at least three independent replicates.

To directly evaluate the effect of BRAF inhibition on oxidative phosphorylation and mitochondrial number and function, the melanoma cell lines were treated with PLX4720, a preclinical analog of vemurafenib (Tsai et al., 2008). PLX4720 increased the mitochondrial density of two BRAF mutant melanomas as detected by MITOTRACKER® Green, which localizes to mitochondria independent of membrane potential. PLX4720 did not affect the mitochondrial density of MeWo cells that are BRAF wild-type (FIG. 1B). PLX4720 also induced MITOTRACKER® Red fluorescence, a measure of mitochondrial activity and mass (FIG. 1C), and increased the production of mitochondrial oxidative stress measured by the MITOSOX™ fluorescence assay (FIG. 1D). To confirm these findings, the mitochondrial number after treatment of the BRAF mutant melanoma cell line UACC62 with PLX4720 were also evaluated by electron microscopy. As seen in FIG. 1E and FIG. 9D, inhibition of BRAF led to a significant increase in the number of mitochondria per cell.

The conversion of glucose to lactate, as noted by Warburg, can be due to the shunting of pyruvate away from oxidative phosphorylation. In line with the findings described above, PLX4720 reduced lactate levels in all BRAF mutant melanomas evaluated (FIG. 1F). Lactate levels did not change upon treatment of a melanoma cell line that does not contain the BRAF mutation, consistent with the inability of PLX4720 to suppress ERK signaling in these cells (FIG. 1G).

Collectively, the data indicated that BRAF suppresses oxidative phosphorylation gene expression and mitochondrial density in melanoma.

BRAF and MAPK Activation Suppresses PGC1α

Since oxidative phosphorylation depends on mitochondrial number and activity, their alteration can contribute to altered tumor metabolism. Candidate pathways, which physiologically regulate mitochondrial content and function include the transcription factors mitochondrial transcription factors A (TFAM) and B (TFB1M, TFB2M), nuclear respiratory factor 1 (NRF1), GA binding proteins (GABPA, GABPB2), peroxisome proliferator-activated receptors (PPARα, PPARβ), PPAR-γ coactivators (PGC1α, PGC1β), and PGC1-related coactivator 1 (PPRC1) (reviewed in Kelly, 2004).

Figure 2E:
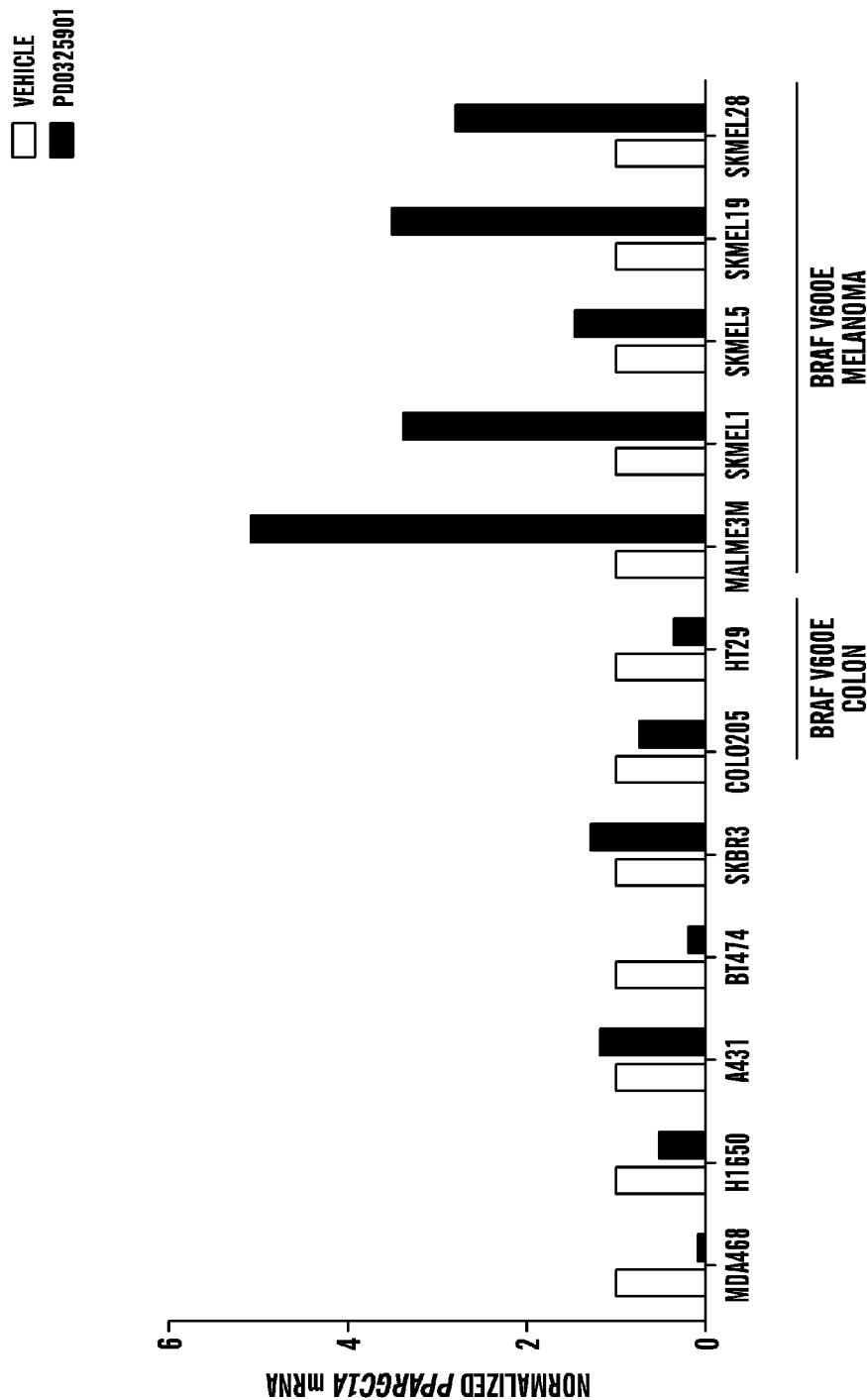
Figures 10A, 10B:
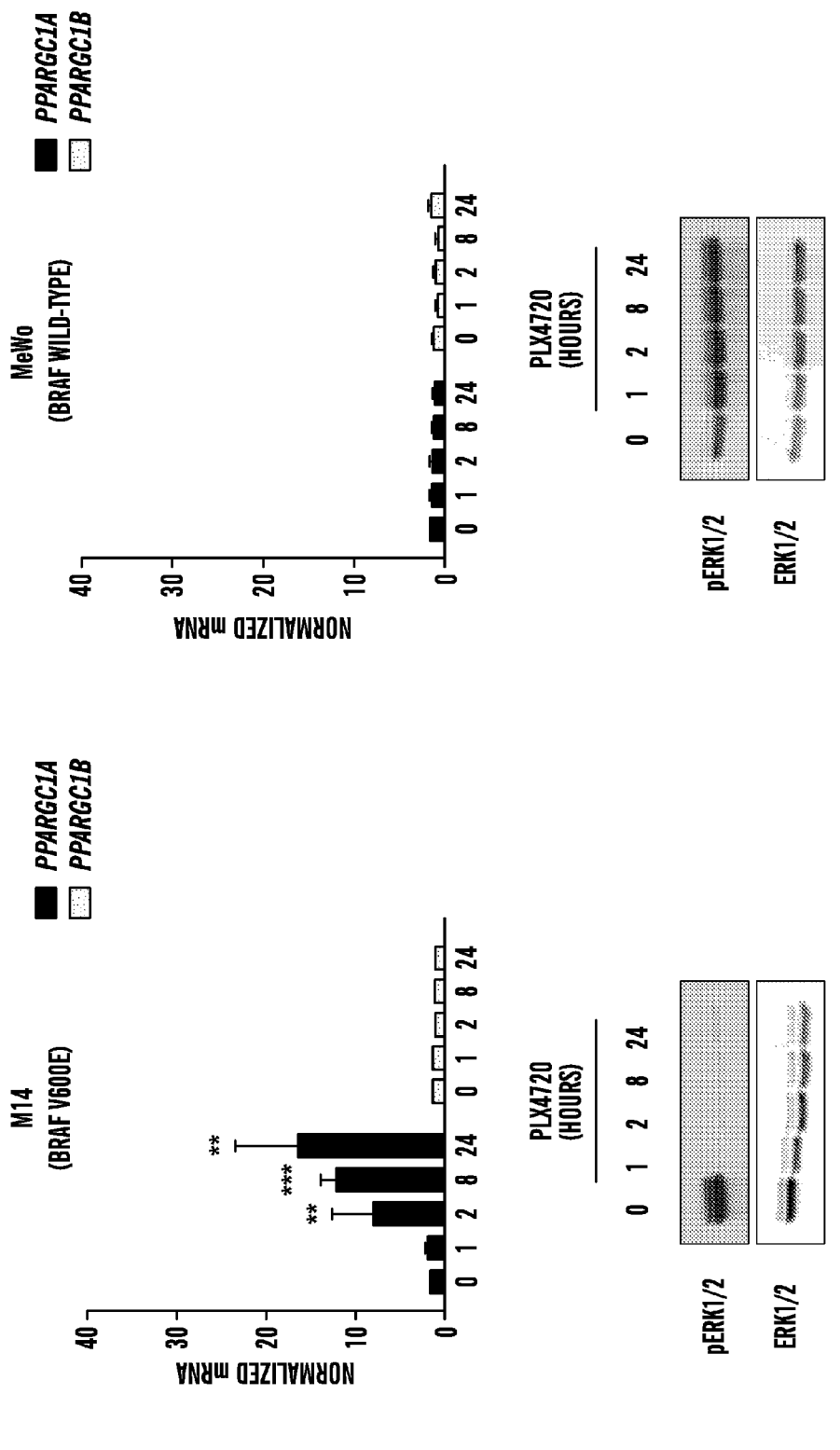
FIG. 10A are histograms showing the time course of PGC1α and PGC1βmRNA induction in BRAF mutant melanoma M14 cells (upper). The lower panel shows Western blots indicating the time course of inhibition of phospho-ERK in BRAF mutant melanoma M14 cells.
FIG. 10B are histograms showing the time course of PGC1α and PGC1βmRNA induction in BRAF-wild-type melanoma MeWo cells (upper). The lower panel shows Western blots indicating the time course of inhibition of phospho-ERK in BRAF-wild-type melanoma MeWo cells.
Figures 10C, 10D, 10E:
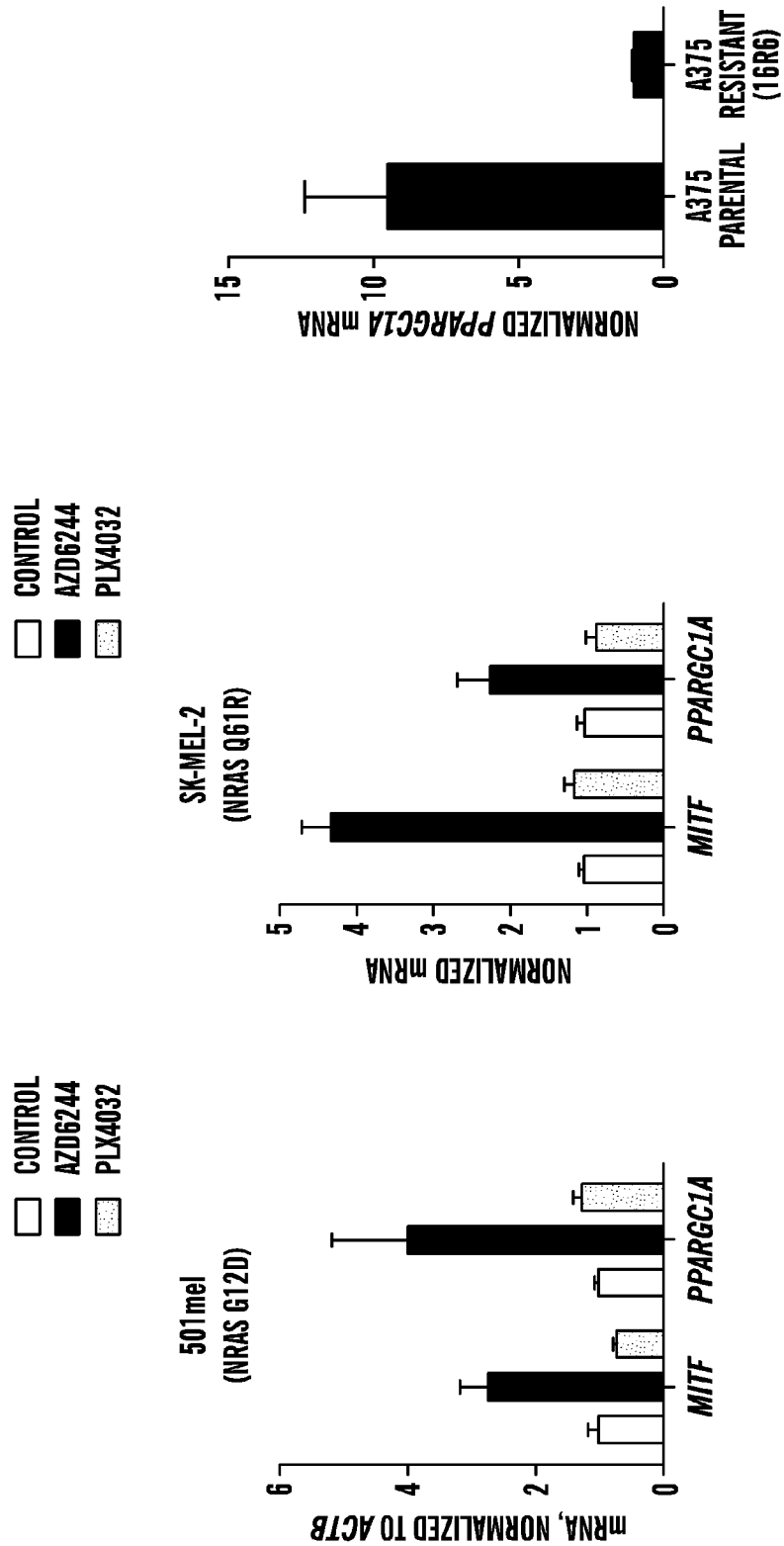
FIG. 10C are histograms showing the expression of MITF and PGC1α in NRAS-mutant cell line (NRAS-G12D) upon 24 h treatment with PLX4032 (1 µM) or AZD6244 (1 µM).
FIG. 10D are histograms showing the showing the expression of MITF and PGC1α in NRAS-mutant cell line (NRAS-G61R) upon 24 h treatment with PLX4032 (1 µM) or AZD6244 (1 µM).
FIG. 10E are histograms showing the expression of PGC1α in A375 parental cells and in BRAF inhibitor resistant clone (16R6) extracted from Greger J G et al. (2012). Error bars represent SEM of at least three independent replicates.

It was observed that BRAF(V600E) expression suppressed PGC1α, a well-known regulator of mitochondrial metabolism, in the microarray datasets above. To validate these observations, a series of BRAF-mutant melanomas and non-melanoma cell lines were treated with PLX4720 and evaluated the effect on PGC1α mRNA (FIG. 2A). In all melanomas with BRAF mutations, PLX4720 induced 3-14 fold increases in PGC1α mRNA. No change in the expression of PGC1α in a BRAF wild-type melanoma treated with PLX4720 was observed. Surprisingly, no effect of PLX4720 on PGC1α expression in two BRAF mutant colon cancer cell lines was also observed, despite suppression of ERK phosphorylation similar to that seen in melanomas (FIG. 2B). There was also no change in PGC1β mRNA upon treatment with PLX4720 or any effects in a BRAF-wild-type melanoma over 24 hours (FIGS. 10A and 10B). These data indicated that there might be lineage-specific differences in the regulation of PGC1α by BRAF. To validate these findings using a structurally unrelated small molecule, several melanoma cell lines were treated with the MEK inhibitor PD0325901. Suppression of ERK phosphorylation (FIG. 2D) and induction of PGC1α mRNA (FIG. 2C) were seen in all cell lines tested, including the BRAF wild-type melanoma MeWo, indicating that the BRAF/MEK/ERK pathway regulates PGC1α expression in melanoma cells. These results were also confirmed with additional NRAS-mutant melanoma cell lines treated with a MEK1/2 inhibitor (FIGS. 10C and 10D). Finally, the expression of PGC1α in an independent dataset of A375 melanoma cells selected for resistance to BRAF inhibitors (Greger et al., 2012) were evaluated. It was observed that PGC1α expression was 10-fold lower in cells that had acquired resistance to BRAF inhibitors (FIG. 10E), likely reflecting their higher demonstrated basal MAPK activity.

Figure 2F:
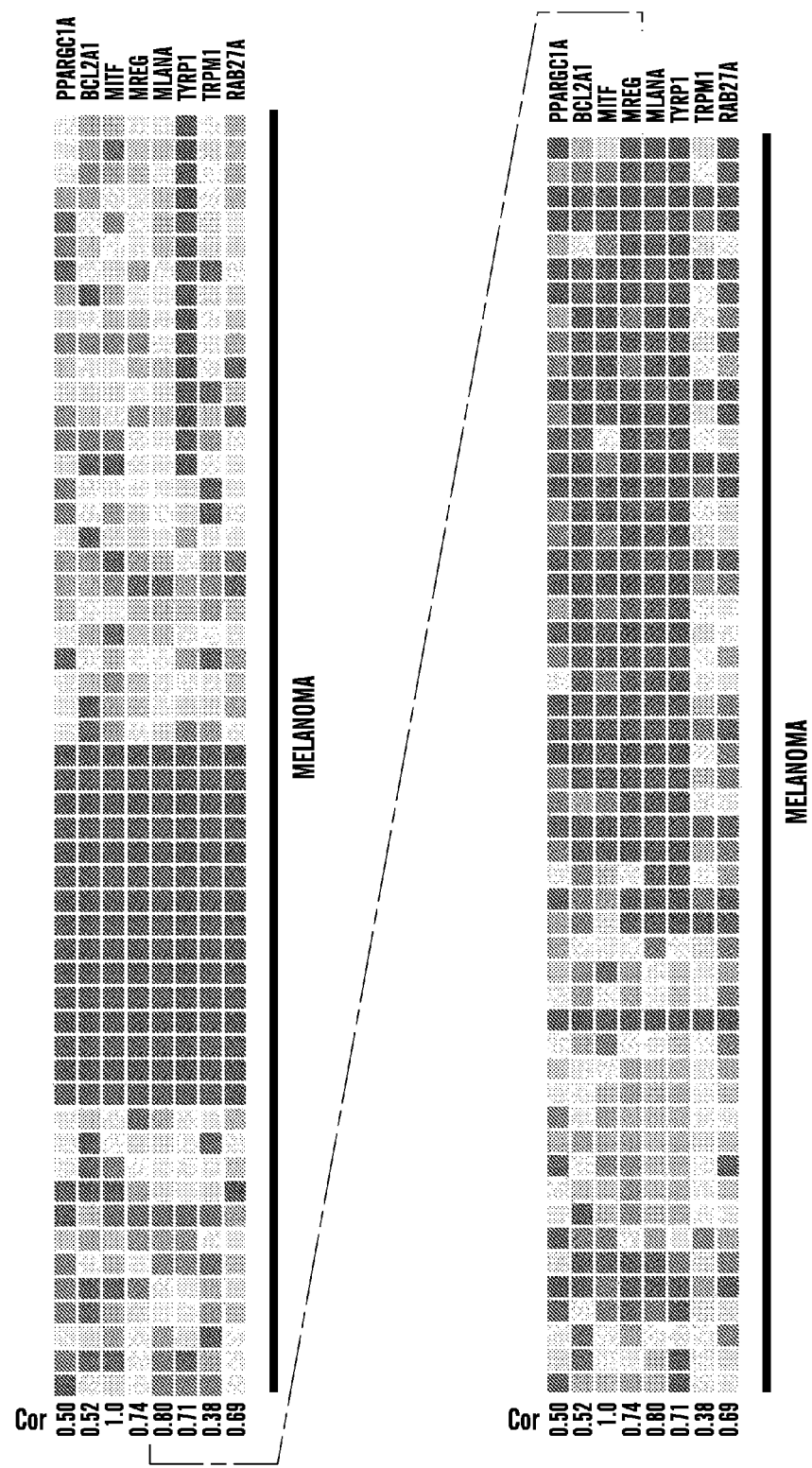

The inventors interrogated a publically available microarray of 12 breast, lung, colon and melanoma cell lines treated with PD0325901 (Joseph et al., 2010). Suppression of MEK only affected PGC1α mRNA in melanoma cell lines (FIG. 2E, p<0.0001), indicating that the regulation of PGC1α mRNA by the BRAF/MEK/ERK pathway is unique to the melanocytic lineage. Consistent with the results, it was found that PGC1α expression was significantly correlated with melanocyte-specific antigen expression in a dataset comprising of 105 melanoma cell cultures (FIG. 2F).

PGC1α mRNA is Directly Regulated by the MITF Transcription Factor

To elucidate how BRAF may regulate PGC1α, the expression pattern of all human transcription factors was compared to PGC1α in a large microarray dataset of short-term melanoma cultures (Lin et al., 2008). Among the transcription factors whose expression most closely paralleled PGC1α, it was observed that both transcription factor EB (TFEB) and the micropthalmia-associated transcription factor (MITF) were significantly associated with PGC1α expression (q<0.001) (FIG. 3A). Both TFEB and MITF are members of a four-member family of distinctly encoded transcription factors (TFEB, TFEC, TFE3 and MITF) that share a common structure, binding recognition sequence, and function (Haq and Fisher, 2011). Whereas TFEB, TFEC, and TFE3 are ubiquitously expressed, MITF is largely restricted to the melanocytic lineage. The correlation of PGC1α to MITF was therefore interesting in light of our data suggesting BRAF regulation of PGC1α in melanoma but not in other lineages (see FIGS. 2A, 2F). MITF expression correlated to PGC1α as shown above (see FIG. 2E).

Figure 11B:
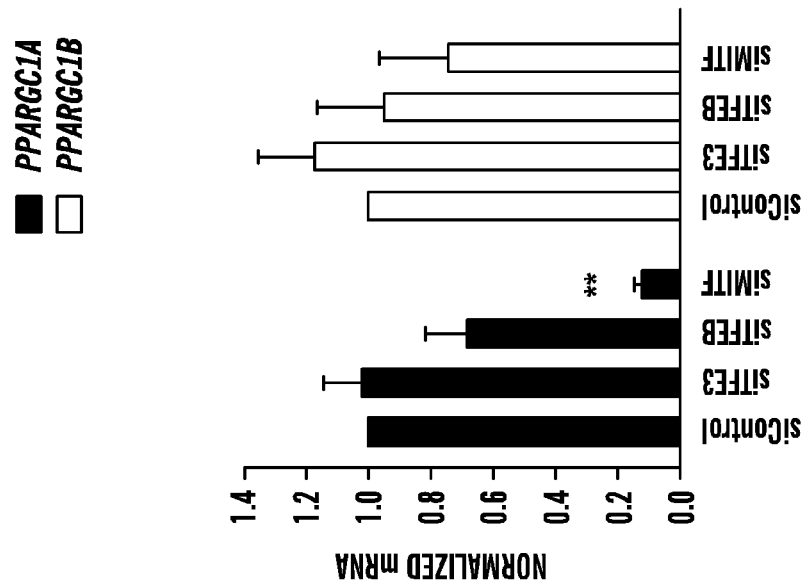
FIG. 11B are histograms showing the effect of knockdown of respective MiT family members on expression of the PGC1α and PGC1β(b) in primary human melanocytes.
Figure 11A:
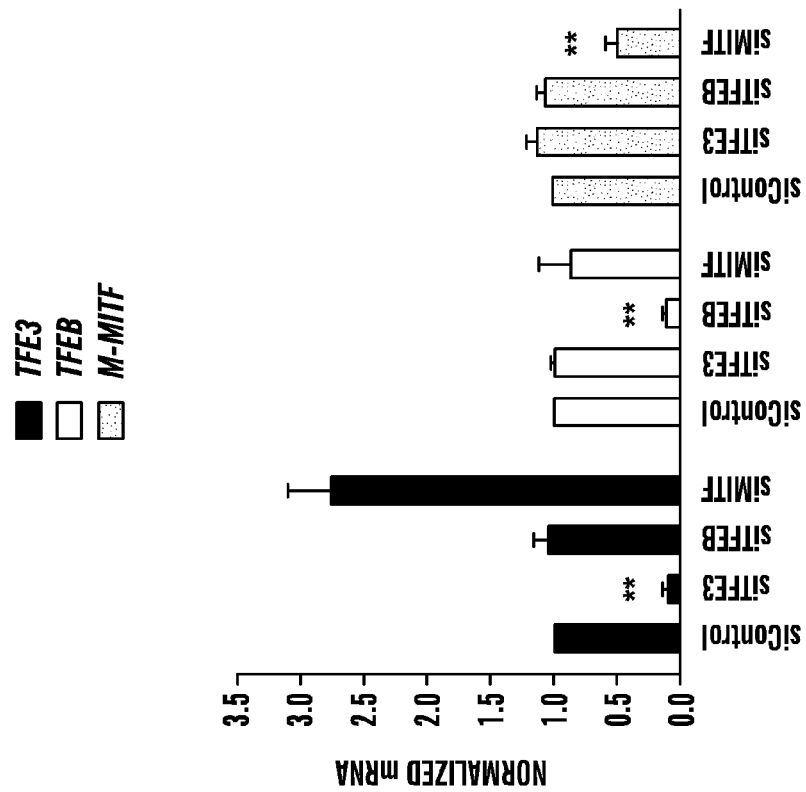
FIG. 11A are histograms showing the effect of knockdown of respective MiT family members on expression of the individual MiT family members in primary human melanocytes.
Figures 11C, 11D:
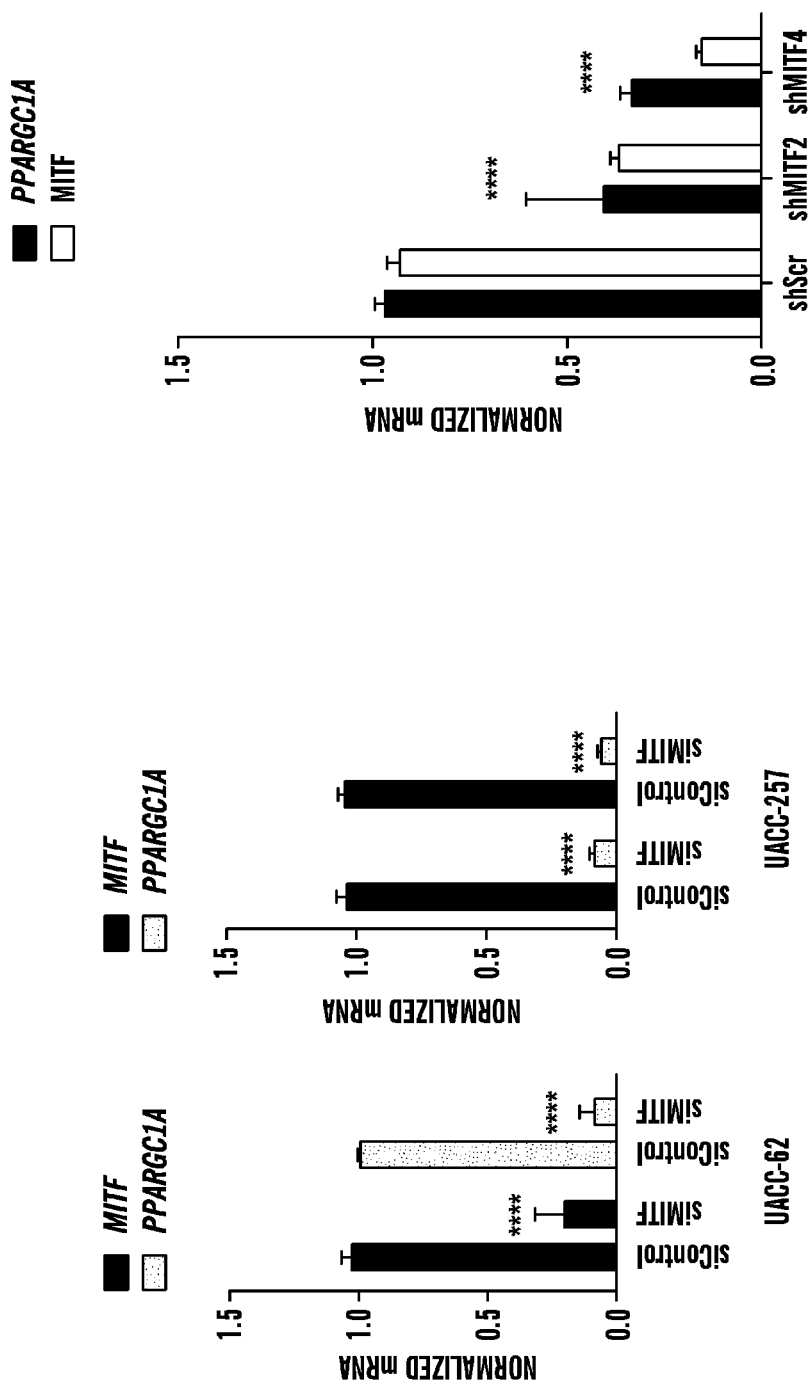
FIG. 11C are histograms showing the effect of MITF knockdown in two additional melanoma cell lines, UACC-62 and UACC-257.
FIG. 11D are histograms showing the effect of MITF knockdown with two distinct shRNAs in MALME melanoma cells on PGC1α and MITF mRNA. Error bars represent SEM of at least three independent replicates.

The inventors therefore proceeded to evaluate the requirement of TFE3, TFEB and MITF for the expression of PGC1α by siRNA. In both M14 melanoma cells and primary human melanocytes, suppression of MITF but not TFEB or TFE3 led to a significant suppression of PGC1α (FIG. 3C, 11B) despite similar knockdown efficiency (FIG. 3B, 11A). The inventors were unable to reliably detect TFEC expression in the cell lines tested (data not shown). MITF suppression in two other melanomas lines also significantly reduced PGC1α expression (FIG. 11C), which was validated using two independent shRNAs (FIG. 11D).

Figure 3D:
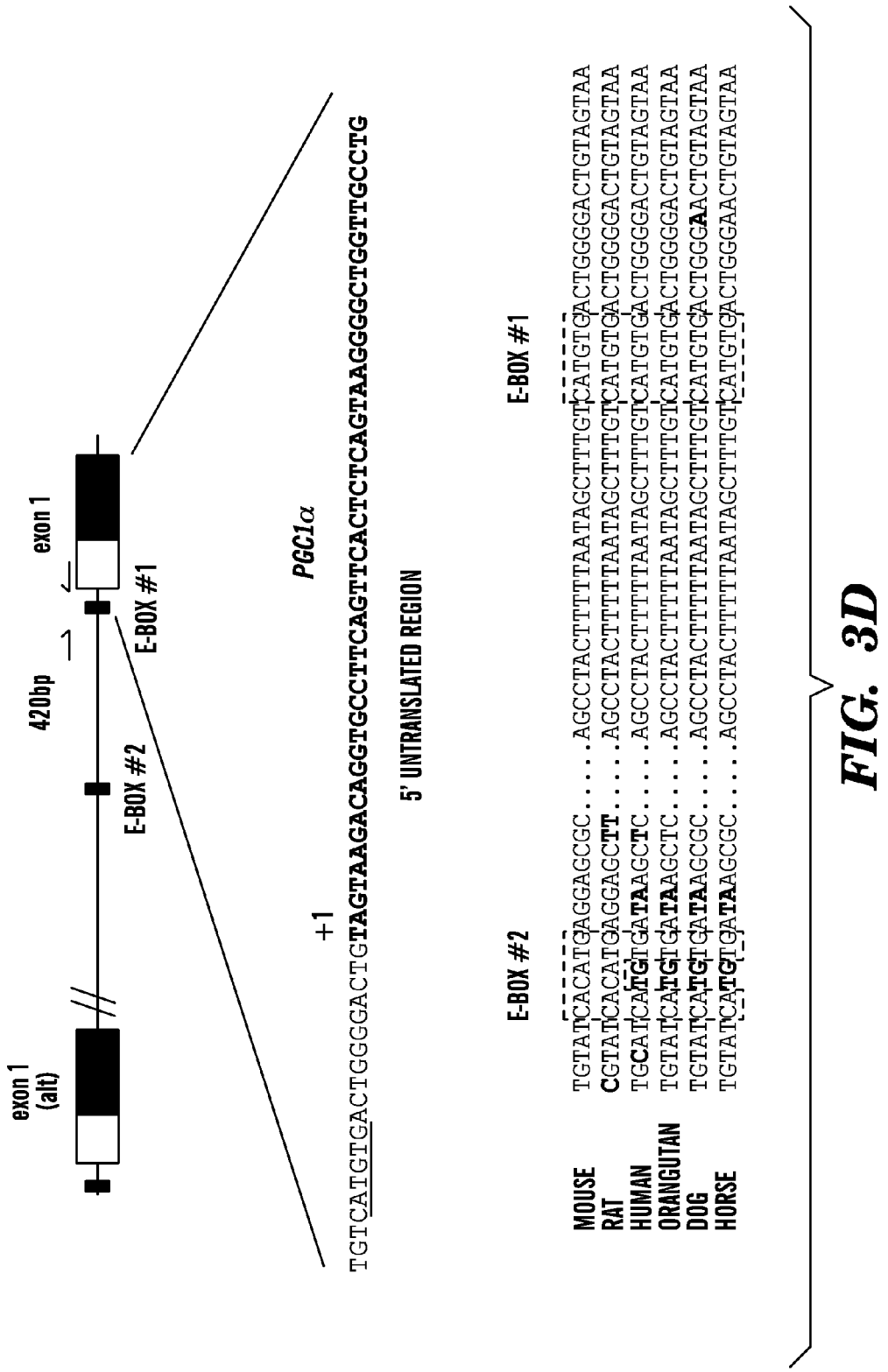
Figure 3E:
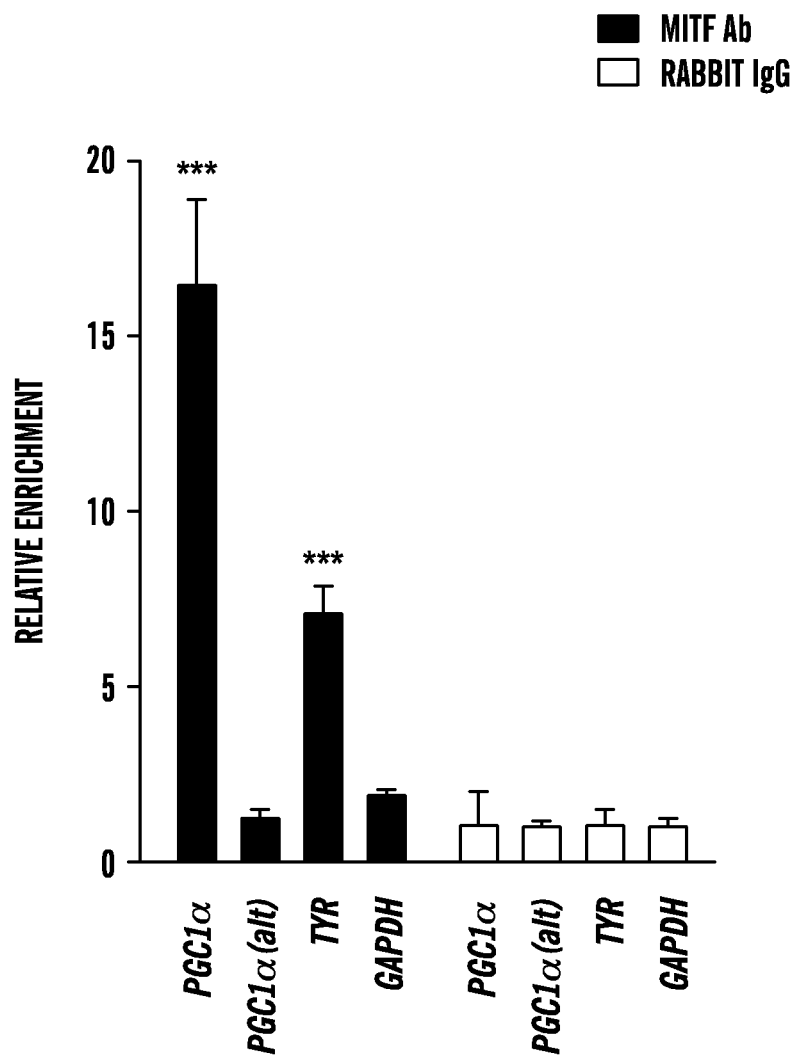
Figure 3F:
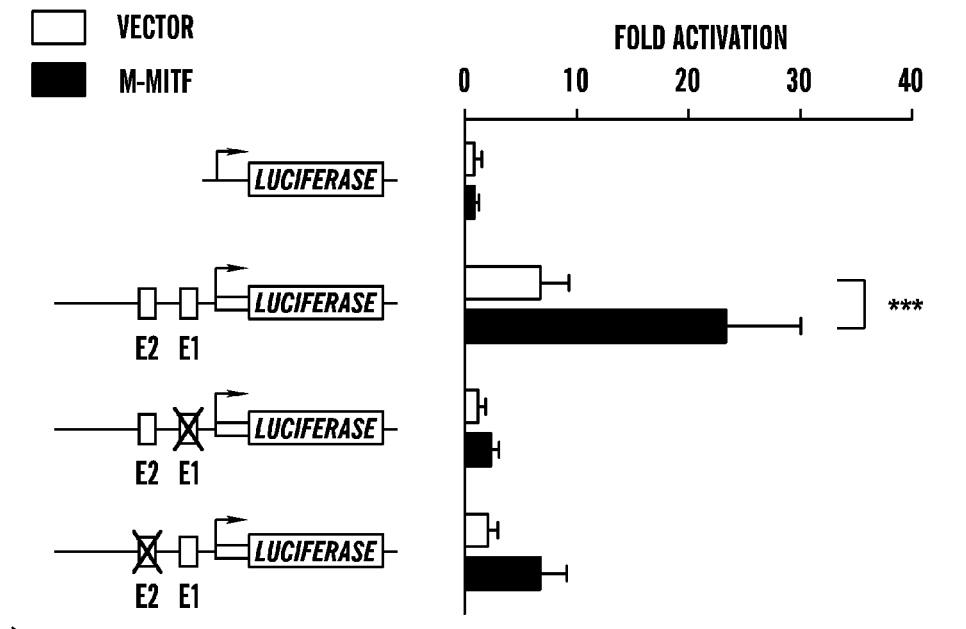
Figure 3G:
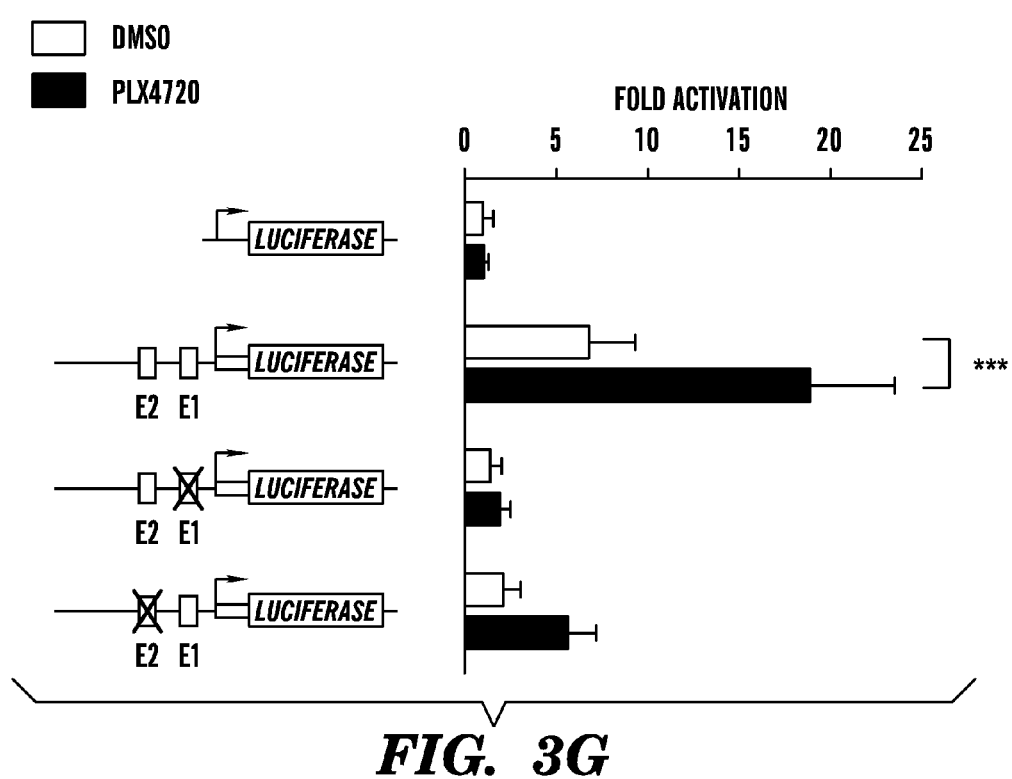

In sillico analysis of the PGC1α promoter identified three putative MITF recognition sequences ('E-boxes'), which were conserved among mammalian species. One E-box was located approximately 420 bp upstream of the transcriptional start site, whereas a proximal E-box was located within 20 bp of the start site (FIG. 3D). Another E-box was located approximately 10 kilobases upstream of these sequences, in the promoter sequences of an alternative exon 1 (PGC1α-alt) (Miura et al., 2008; Chinsomboon et al., 2009). To evaluate if MITF could directly bind to the PGC1α promoter, chromatin immunoprecipitation was performed using primers located either near alternative exon 1 or exon 1 (see FIG. 3D). As shown in FIG. 3E, MITF was found to bind to the proximal PGC1α promoter but not to the PGC1α-alt promoter in primary melanocytes. Due to limits in the resolution of this assay, we were unable to distinguish if MITF binds to E-box #1, E-box #2 or both. The inventors therefore utilized a PGC1α promoter cloned upstream of the luciferase reporter gene (Handschin et al., 2003) and mutated each E-box by site-directed mutagenesis (FIG. 3F). MITF overexpression (FIG. 3F) or treatment with PLX4720 (FIG. 3G) led to the induction of the wild-type promoter, whereas mutation of either of the two E-boxes significantly inhibited this response. Collectively, these data indicate that MITF binds and directly regulates the PGC1α gene in the melanocyte lineage. To evaluate if BRAF regulates PGC1α via MITF, MITF expression in cells was suppressed by siRNA, and the cells were then treated with PLX4720. As shown in FIG. 3H, treatment with PLX4720 strongly induced PGC1α mRNA in M14 cells and 3 fold in UACC62 cells and this induction was absent in cells in which MITF was knocked down by siRNA. These data indicate that BRAF regulates PGC1α via MITF.

BRAF Negatively Regulates MITF Activity

Figure 4B:
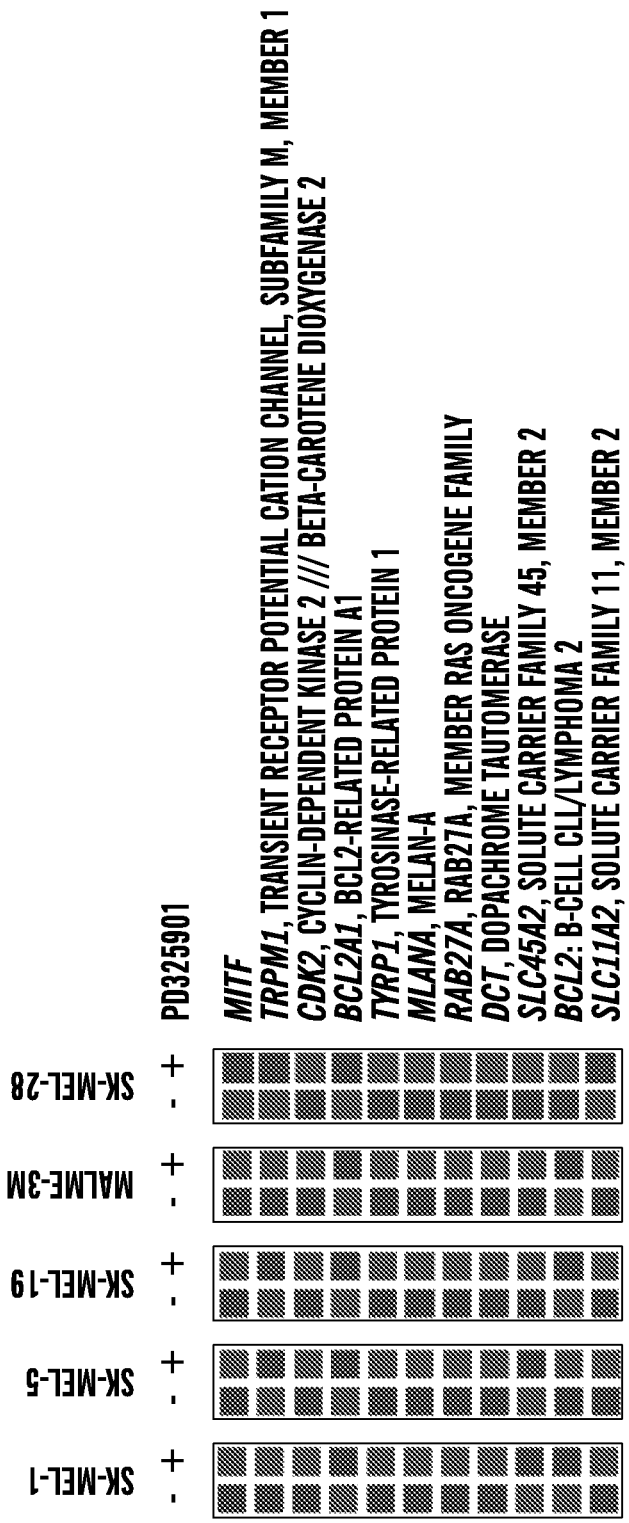
Figure 4C:
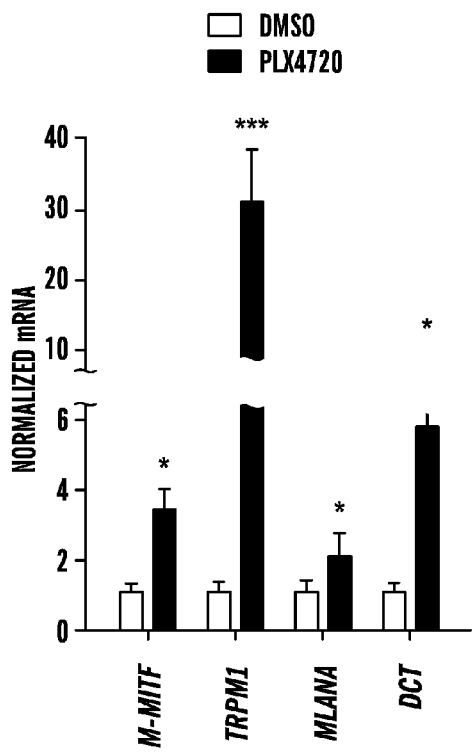
Figure 4D:
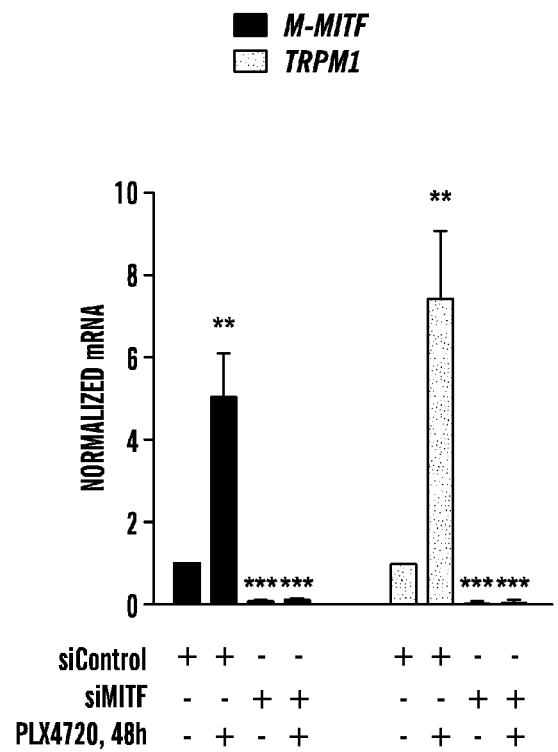
Figure 4E:
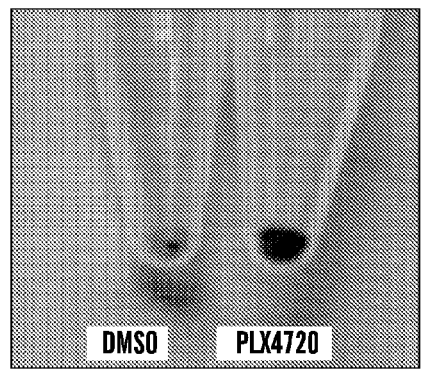

The relationship between BRAF and MITF is poorly understood since oncogenic BRAF and the ERK pathway promotes MITF activation but also leads to its degradation (Hemesath et al., 1998; Wu et al., 2000; Wellbrock, 2005; Wellbrock et al., 2008; Boni et al., 2010). The inventors therefore examined the consequences of ectopic BRAF (V600E) expression in immortalized melanocytes. Introduction of oncogenic BRAF was associated with decreased levels of M-MITF protein (the melanocyte-specific isoform) but not with other isoforms (FIG. 4A). Conversely, the MEK inhibitor PD0325901 induced the expression of TRPM1 and other direct targets of MITF in published microarrays (FIG. 4B) and by qtPCR (FIG. 4C). These effects on MITF targets were dependent on MITF, since knockdown of MITF blocked induction of TRPM1 (FIG. 4D). In line with these findings, it was observed that treatment of UACC-257 cells with PLX4720 for 72 h lead to increased pigmentation, reflecting MITF's essential role in melanin synthesis and pigmentation (FIG. 4E).

Figure 4F:
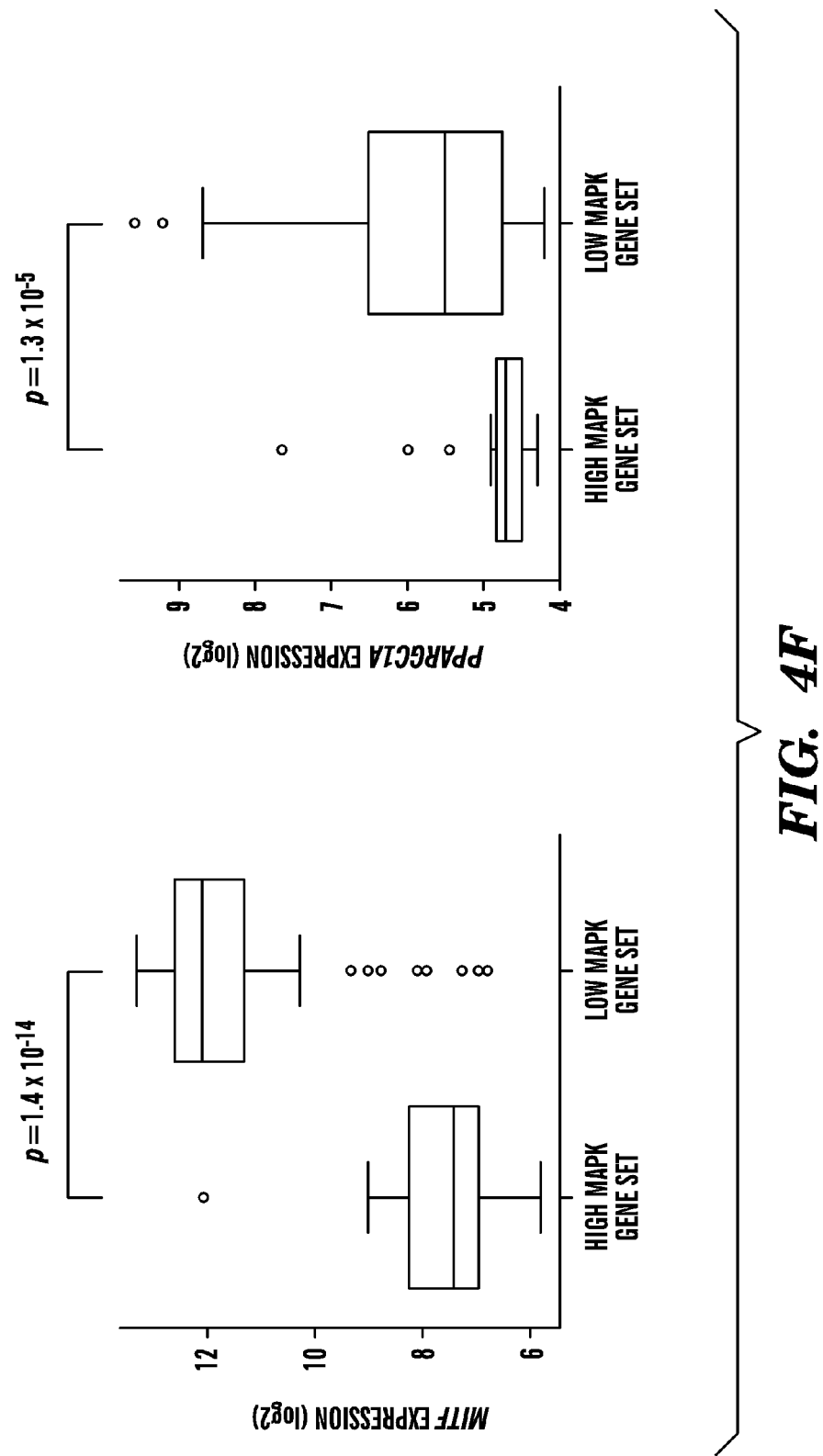

The inventors were unable to detect a correlation between BRAF mutation status and PGC1α or MITF expression in short-term cultures. Given the prevalence of MAPK pathway mutations other than BRAF(V600E) in melanoma, the expression of PGC1α and MITF in melanomas with either high or low expression of a MAPK activation gene signature were evaluated. Both MITF (t-test, $p=1.4\times10^{-14}$) and PGC1α (t-test, $p=1.34\times10^{-5}$) expression inversely correlated with MAPK activity (FIG. 4F). Collectively, these data suggest that BRAF/MAPK inhibition leads to activation of MITF mRNA and protein and that this induction leads to induction of MITF targets including PGC1α.

Figure 5A:
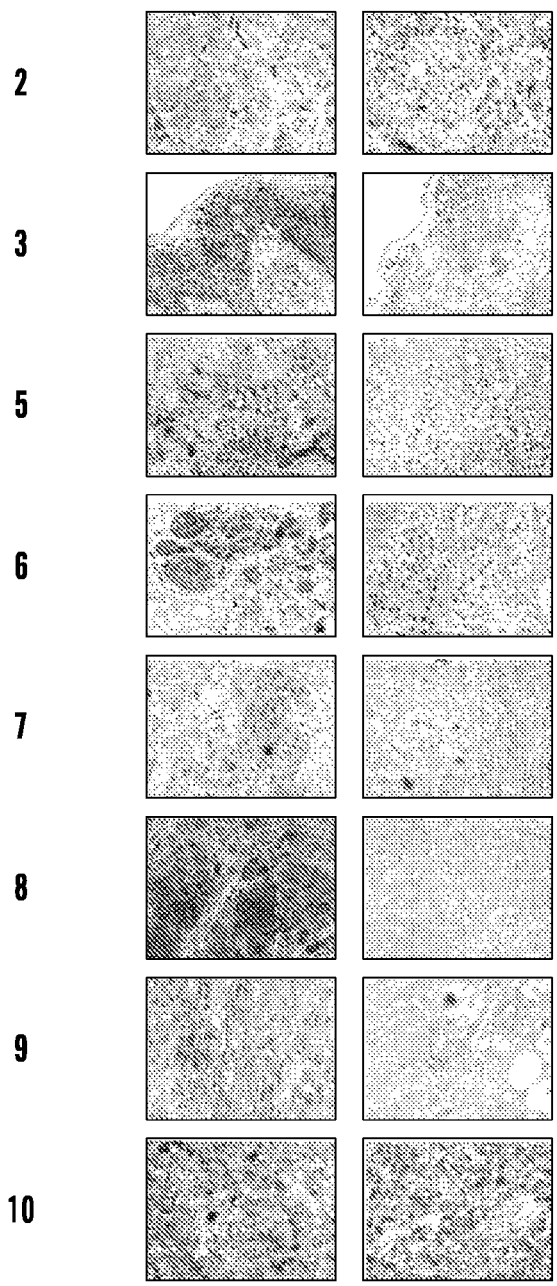
FIGS. 5A-5B show the validation of induction of PGC1α pathway in vivo following BRAF inhibition.
Figure 5B:
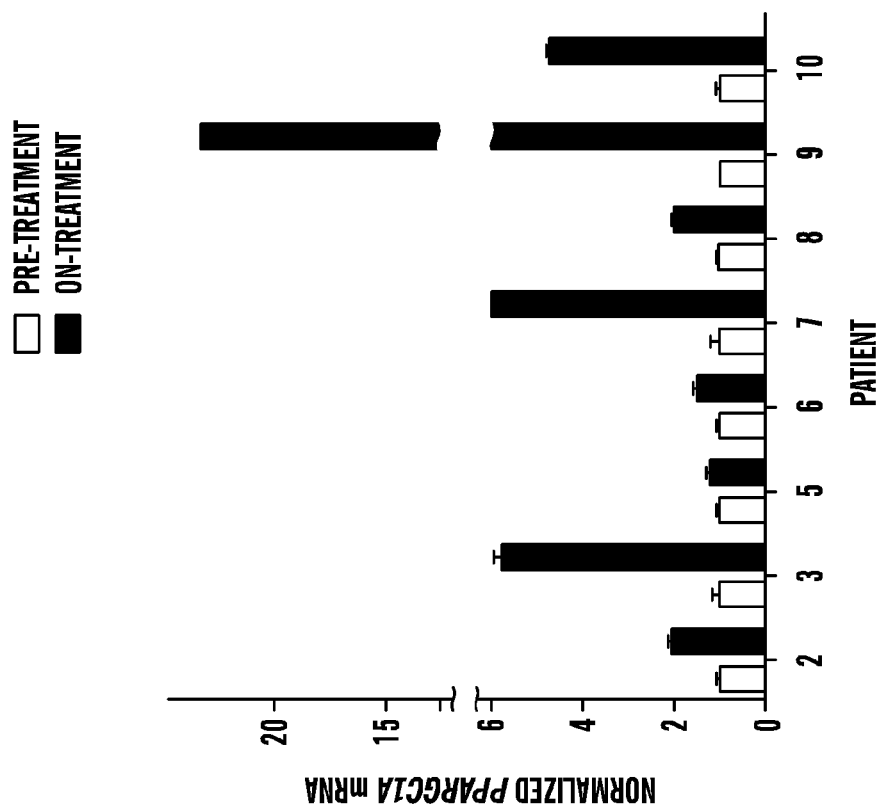

To evaluate if BRAF suppression alters the BRAF/MITF/PGC1α pathway described here in vivo we obtained serial biopsies from 11 patients prior to treatment with BRAF/MEK inhibitors and 10-14 days after beginning treatment (patient characteristics described in Straussman et al., 2012). Of eight samples that had detectable phosphorylated ERK at baseline, all had induction of PGC1α upon treatment (FIG. 5B). Comparison to separately analyzed levels of M-MITF induction following BRAF targeted therapy revealed a significant correlation to PGC1α induction within these patient-derived specimens (Wargo J et al., manuscript in preparation). Together these data indicate that the OXPHOS adaptive response described here exists in vivo.

MITF Promotes Expression of Oxidative Phosphorylation Genes

Figure 6A:
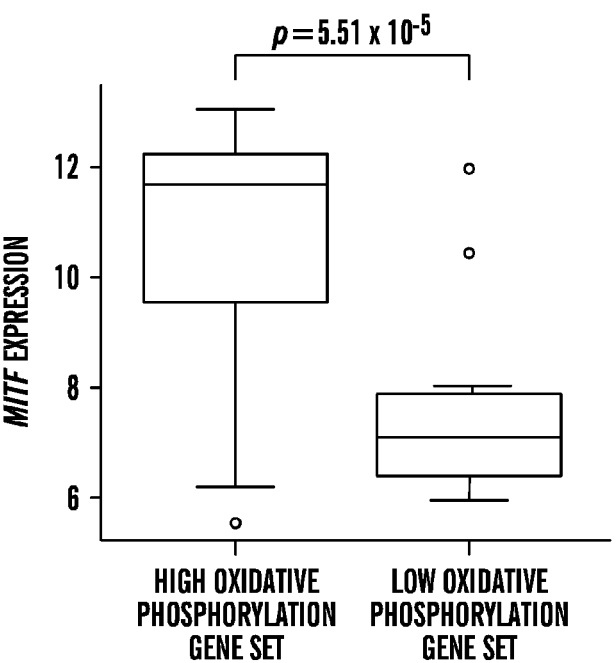
FIGS. 6A-6G show that MITF regulates oxidative phosphorylation.
Figure 6A:
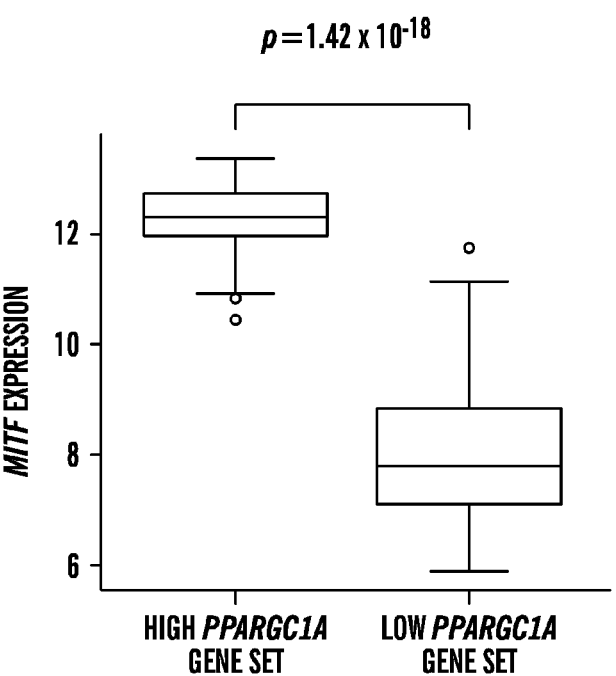

Up to 30% of melanomas harbor genomic amplifications of MITF (Garraway et al., 2005), and MITF is required for the survival of at least a subset of melanomas. Activating point mutations have also been identified in melanoma (Bertolotto et al., 2011; Yokoyama et al., 2011). These data have led to the designation of MITF as a lineage-specific melanoma oncogene (Garraway et al., 2005). Comprehensive expression profiling approaches have identified roles for MITF in promoting cell growth and survival, organelle biogenesis, oxidative stress response and miRNA regulation (Vachtenheim and Borovanský, 2010; Haq and Fisher, 2011). However a role for MITF in regulating metabolism has not been previously described. The inventors therefore tested if MITF expression correlated with oxidative phosphorylation by classifying melanomas into two groups based on a previously defined oxidative phosphorylation signature. As seen in FIG. 6A, melanomas with high MITF expression had significantly higher oxidative phosphorylation gene expression ($p=5.51\times10-5$). Similarly, MITF expression correlated with PGC1α-regulated gene expression ($p=1.42\times10^{-}$15).

Figure 6B:
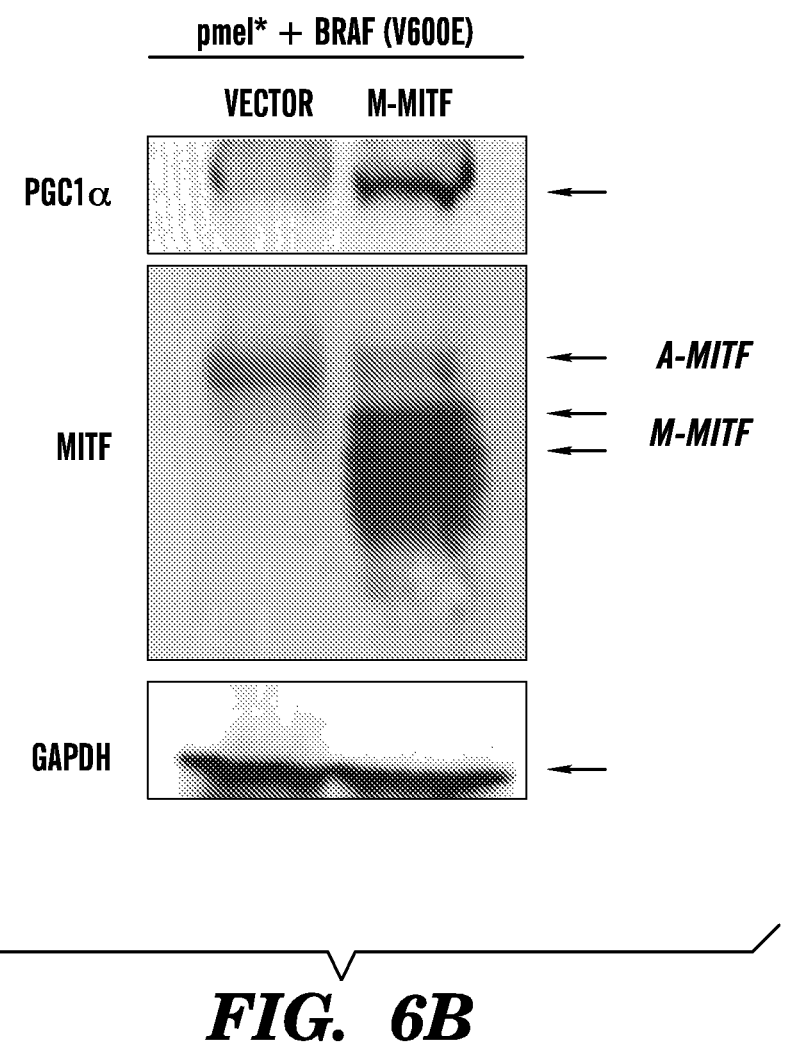
Figure 6C:
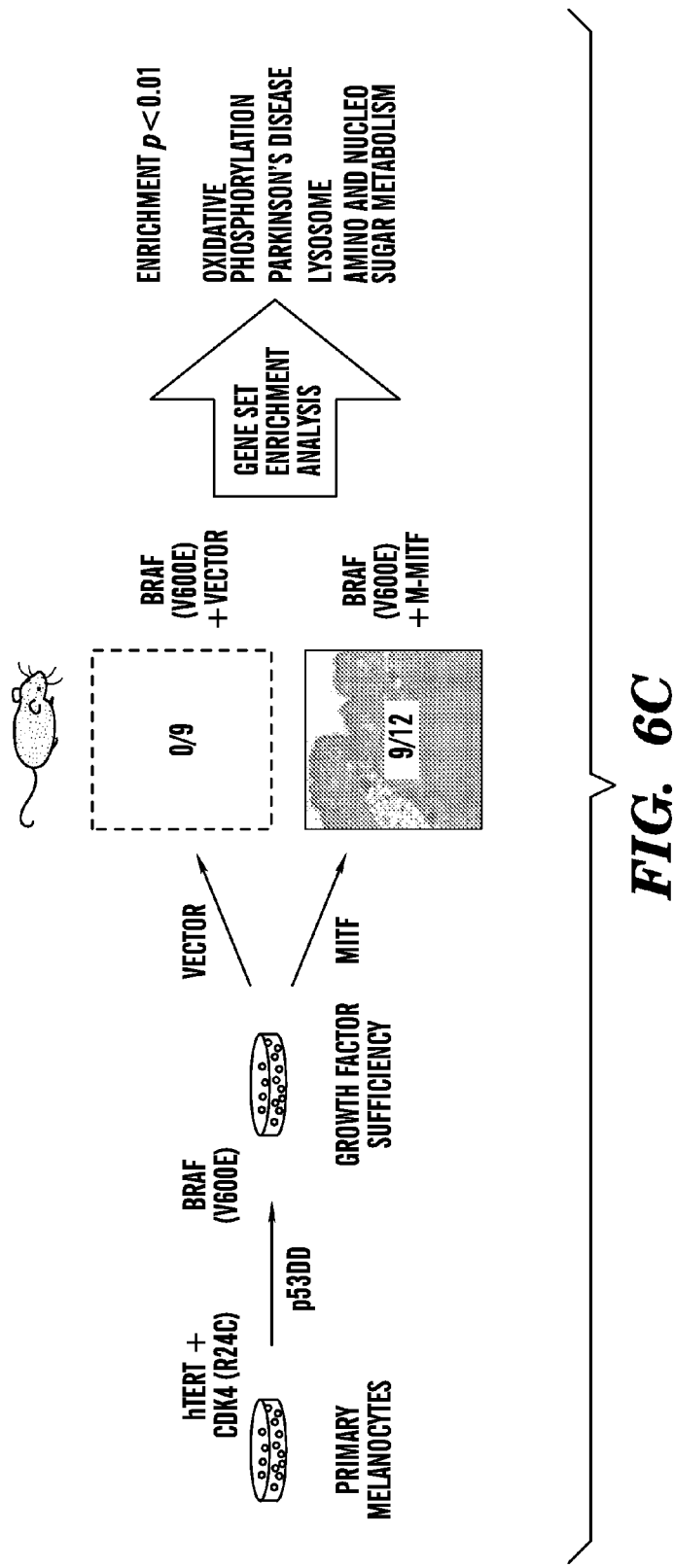
Figure 12A:
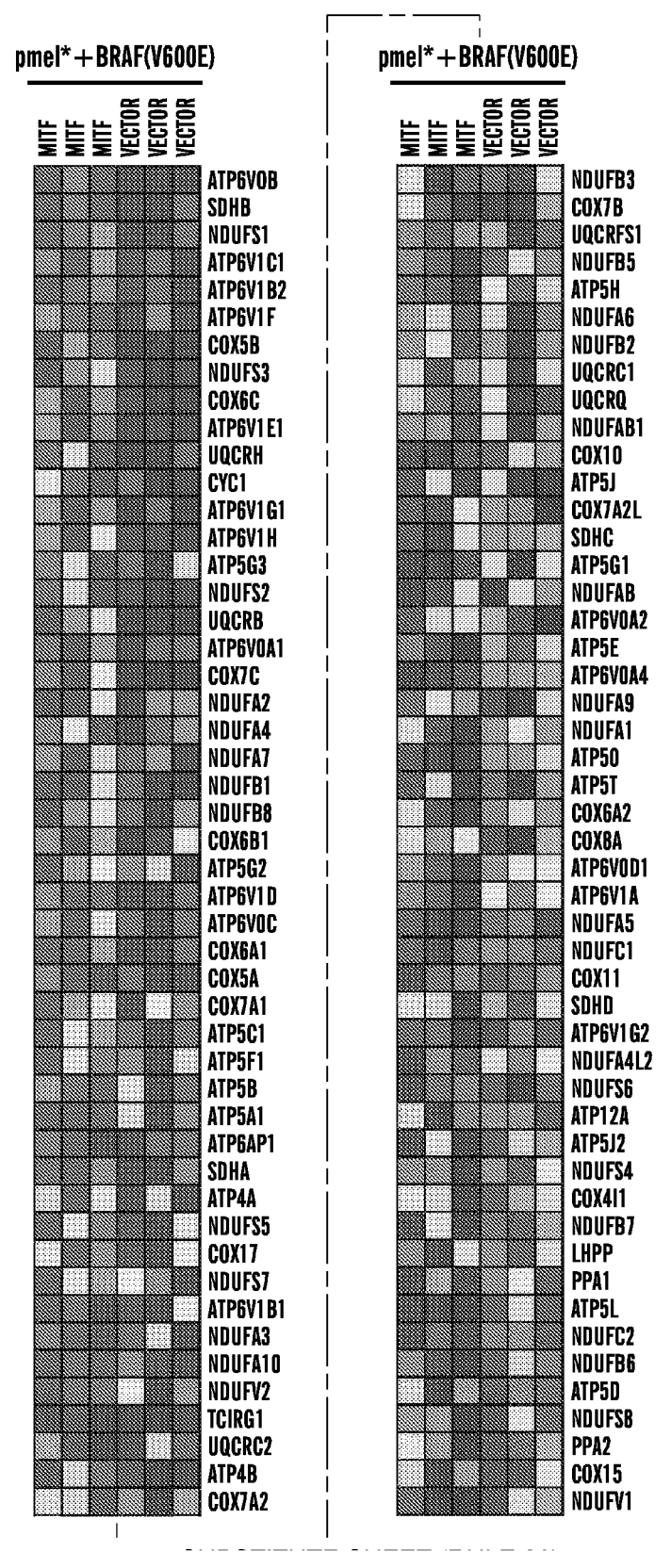
Figure 12C:
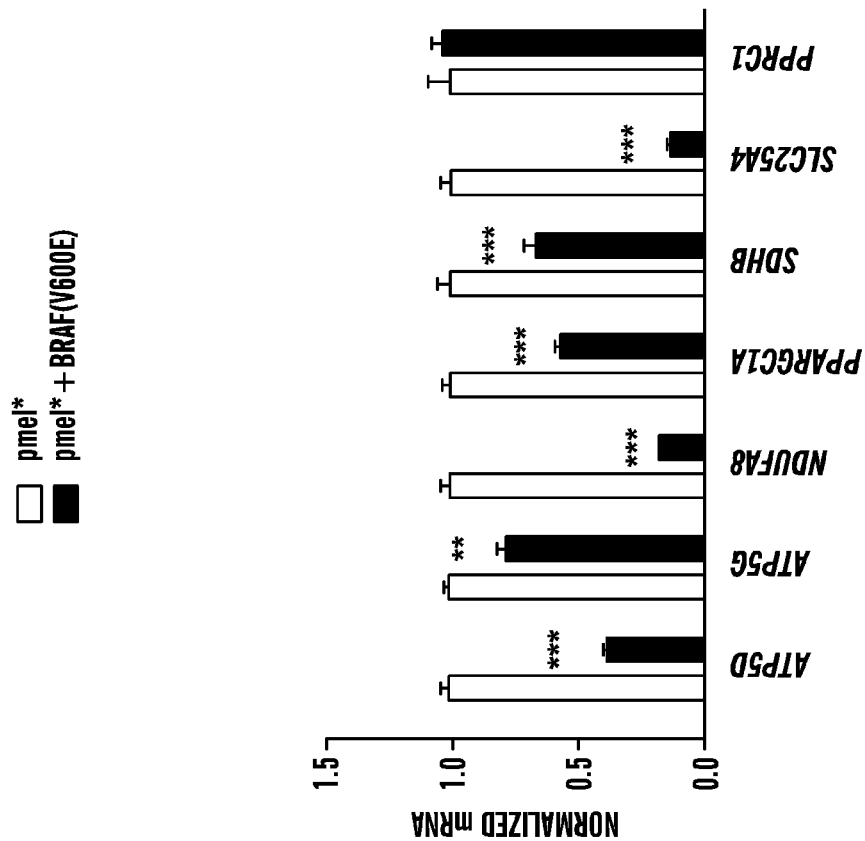
FIG. 12C are histograms showing the expression of oxidative phosphorylation genes in pmel* and pmel*+ BRAF(V600E) cells by qtPCR. , $p<0.01$; *, $p<0.001$. Error bars represent SEM of at least three independent replicates.
Figure 12B:
FIG. 12B are histograms showing the effect of MITF overexpression on oxidative phosphorylation gene set as determined by qtPCR. Error bars represent SEM of at least three independent replicates.

To evaluate if MITF was sufficient to drive oxidative phosphorylation in melanoma, two matched human cell lines derived from primary melanocytes were evaluated. These two cell lines (termed pmel*+BRAF(V600E) and pmel*+BRAF(V600E)+MITF) are derived from primary normal human melanocytes by immortalization using telomerase, with a constitutively active allele of cyclin-dependent kinase 4 and dominant negative p53 (Garraway et al., 2005). These cells are therefore isogenic with the exception of the expression of MITF. Consistent with published reports (Garraway et al., 2005) and the results above, expression of M-MITF protein was undetectable in pmel*+BRAF(V600E) cells, but strongly expressed in the derived MITF-expressing cells, which correlated with PGC1α expression (FIG. 6B). BRAF(V600E) cells expressing MITF were able to form tumors in immunocompromised mice whereas control cells were not (FIG. 6C), paralleling previous data from soft-agar growth (Garraway et al., 2005). Similar to our findings with BRAF inhibition, Gene Set Enrichment Analysis of microarray data identified a highly significant induction of oxidative phosphorylation gene set in MITF expressing cells compared to control cells ($q=0.0$, $p<5\times10^{-4}$; see FIG. 6C). It was found that a large majority of the oxidative phosphorylation gene set was induced by MITF overexpression (FIG. 12A), consistent with the ability of PGC1α to strongly upregulate many oxidative phosphorylation genes (Mootha et al., 2003). The expression of differentially expressed genes (chosen to represent different mitochondrial processes) were validated by qtPCR (FIG. 12B) and found significant increases in several oxidative phosphorylation genes.

Figure 6D:
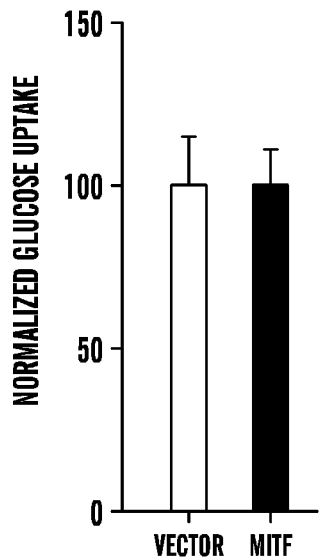
Figure 6E:
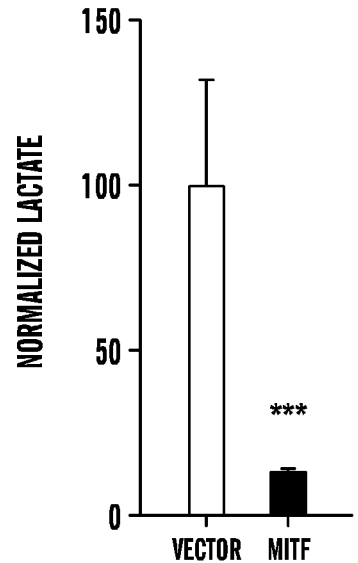
Figure 6F:
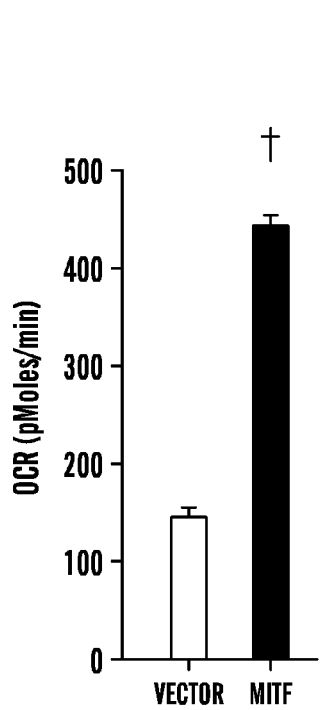
Figure 12E:
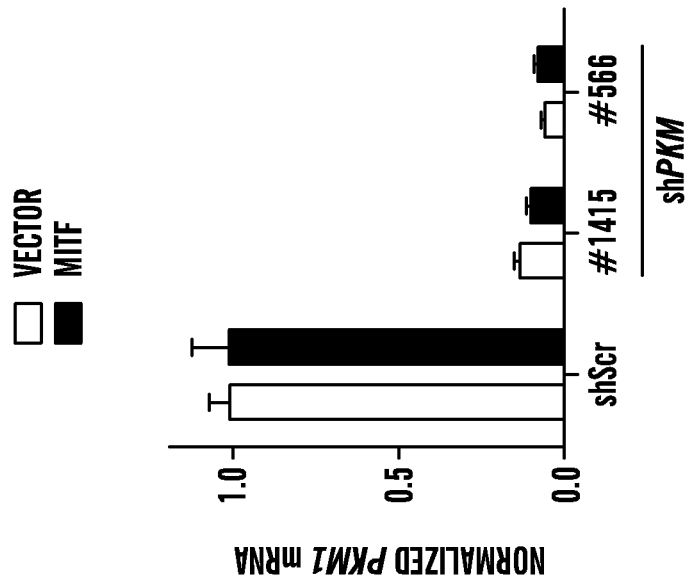
FIG. 12E are histograms showing the knockdown efficiency of PKM shRNAs in BRAF(V600E)+vector and BRAF(V600E)+MITF cells by quantitative PCR 96 hours after infection. Error bars represent SEM of at least three independent replicates.
Figure 12D:
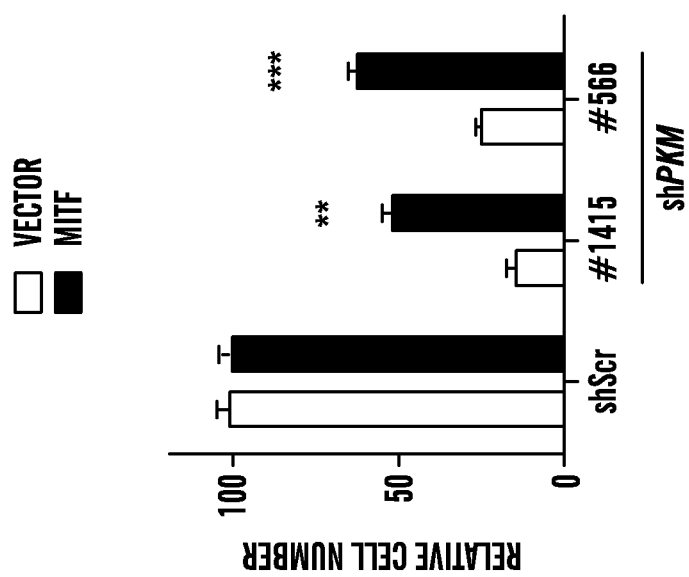
FIG. 12D are histograms showing the effect of suppression of muscle-isoform of pyruvate kinase M (PKM), using independent shRNA sequences, on cell number 96 h after infection of BRAF(V600E)+vector and BRAF(V600E)+ MITF cells. , $p<0.01$; *, $p<0.001$. Error bars represent SEM of at least three independent replicates.

To evaluate the metabolomic consequence of MITF overexpression directly, glycolysis and oxidative phosphorylation in the isogenic cells were evaluated. Overexpression of MITF did not increase glucose uptake (FIG. 6D), but strikingly had decreased lactate production (FIG. 6E) and oxygen consumption (FIG. 6F), consistent with increased mitochondrial metabolism. Conversely, BRAF(V600E) cells had elevated sensitivity to knockdown of pyruvate kinase (muscle isoform), the final step in the glycolysis pathway, compared to isogenic cells expressing MITF (FIG. 12D), despite similar degrees of knockdown efficiency in the two cell lines (FIG. 12E).

To further validate these findings in patient-derived melanomas, we suppressed MITF by shRNA and performed gene expression profiling. Several genes involved in oxidative phosphorylation were identified to be dependent on MITF (FIG. 12F), consistent with the above gene expression data. With the exception of PGC1α, which was found to be directly bound by MITF, oxidative phosphorylation targets were not bound by MITF but have been identified as PGC1α targets in other cell lineages (Mootha et al., 2003). The inventors concluded that MITF overexpression is sufficient and necessary to drive oxidative metabolism gene signature and metabolic reprogramming in the melanocyte lineage.

BRAF Inhibition Leads to Bioenergic Adaptation by Induction of MITF and PGC1α

Collectively, the data above support the notion that BRAF inhibition endangers ATP production, which is rescued by concomitant induction of MITF, PGC1α and oxidative metabolism.

Figure 6G:
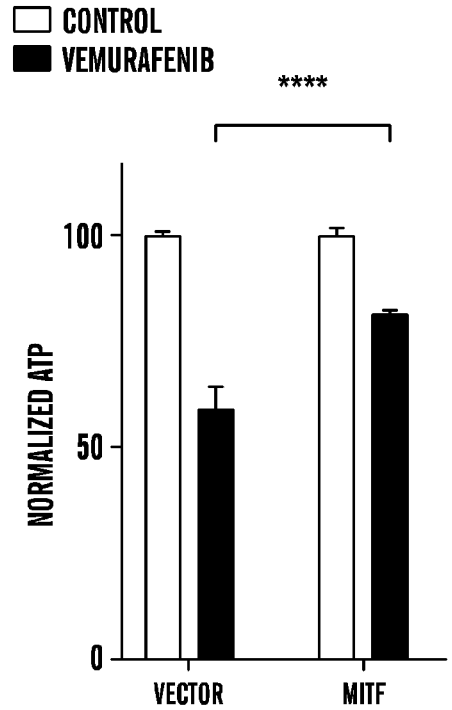
Figure 7B:
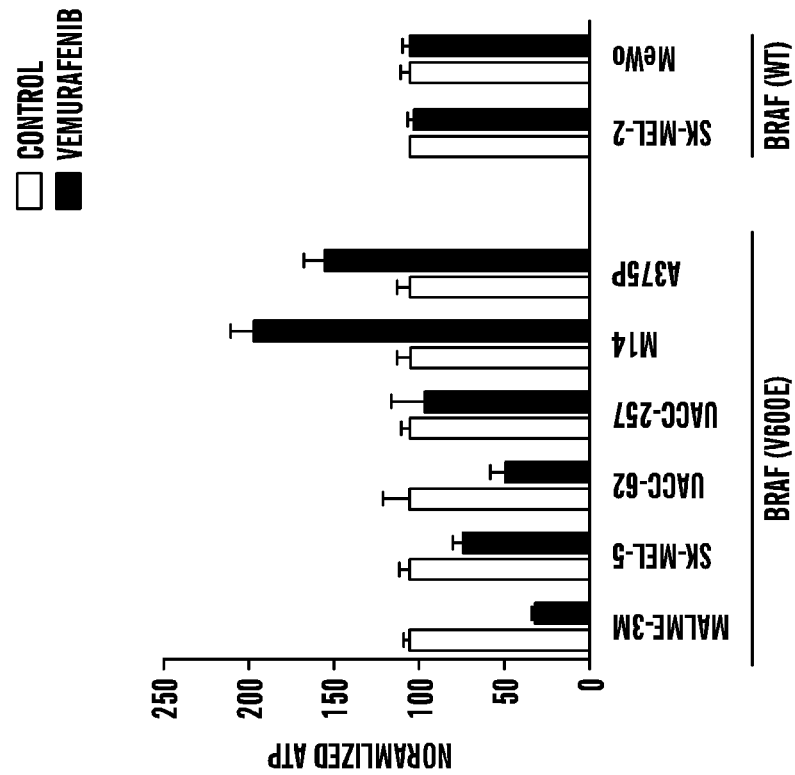
FIGS. 7A-7G show the effects of 2,4-DNP on growth melanoma cells in vitro and in vivo.
Figure 7A:
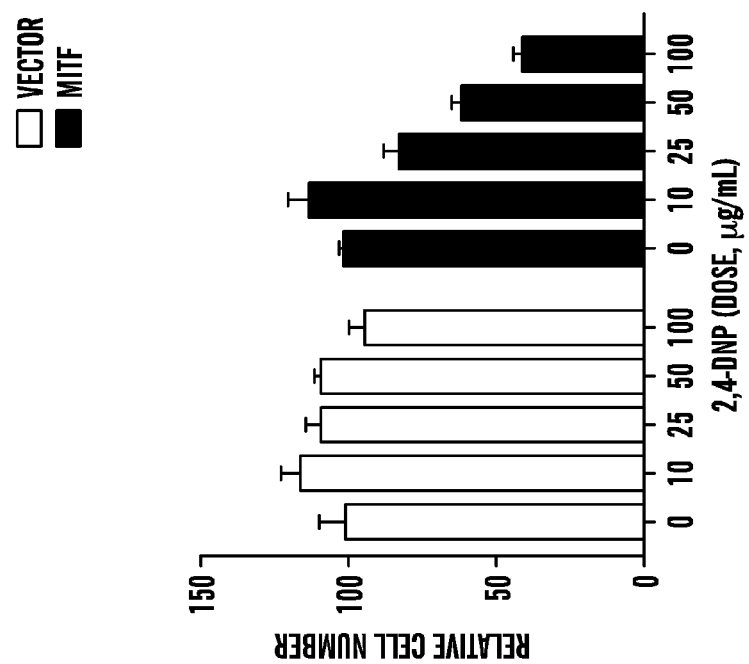

To experimentally test this hypothesis, the response of the isogenic cell lines expressing BRAF(V600E) with or without M-MITF overexpression to PLX4032 were evaluated Inhibition of BRAF resulted in 42% drop in ATP in BRAF (V600E) parental cells whereas the magnitude of this drop was reduced in MITF overexpressing cells (FIG. 6G), despite similar basal ATP concentrations. Consistent with MITF effects on oxidative metabolism, BRAF(V600E)+ MITF cells were significantly more sensitive to the mitochondrial uncoupler 2,4-dinitrophenol (DNP; FIG. 7A).

Figures 7C, 7D, 7E:
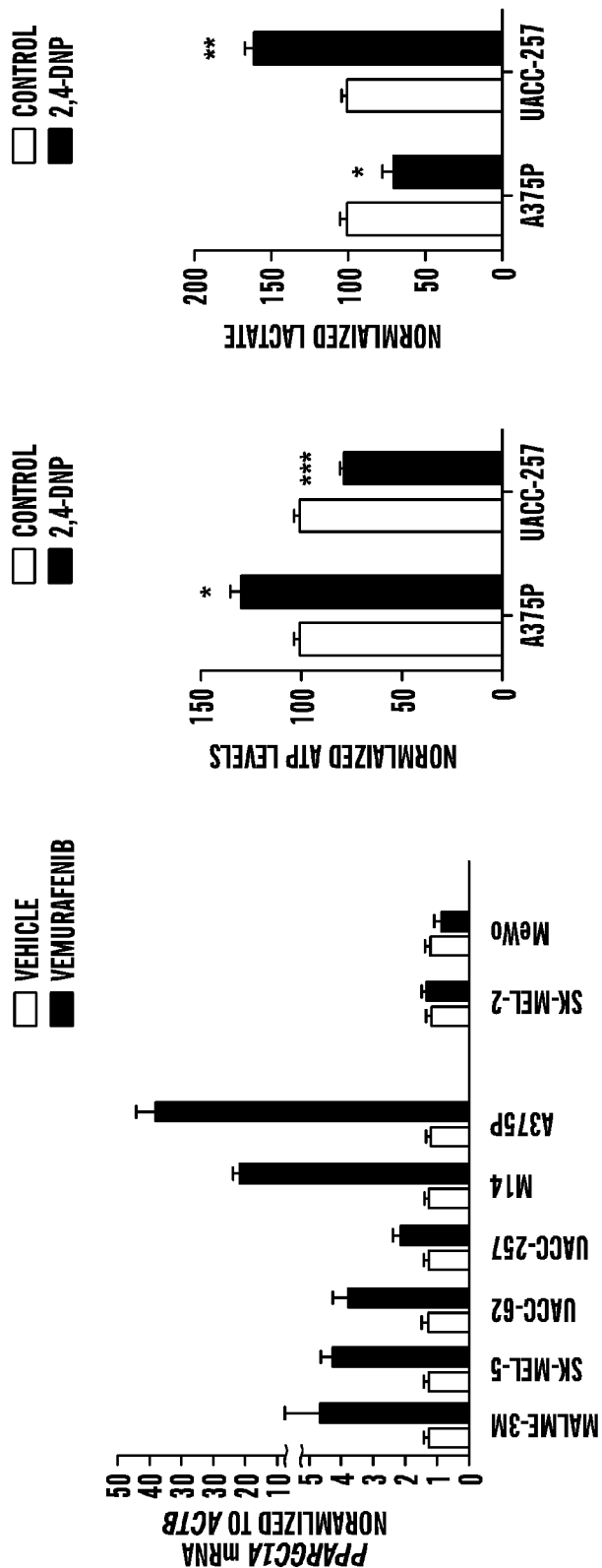

The inventors also evaluated the magnitude of bioenergetic compensation in 8 patient-derived melanoma cell lines. As shown in FIG. 7C, in all cases there was induction of PGC1α following vemurafenib treatment, which varied in magnitude by cell line. The ATP levels were also measured before and after treatment with vemurafenib, and it was observed that there was a significant correlation between induction of PGC1α and ATP levels in BRAF mutant cells (R=0.72, p=0.03; FIG. 7B). Strikingly, the two lines with highest ATP levels following BRAF inhibition are the ones with the strongest induction of PGC1α (see FIG. 7C). These data indicated that the metabolic switch to "normal" varies in magnitude among different melanoma cell lines and suggest that the inhibition of BRAF leads to a bioenergetic crisis that can be variably rescued by induction of the MITF/PGC1α pathway.

Figure 7G:
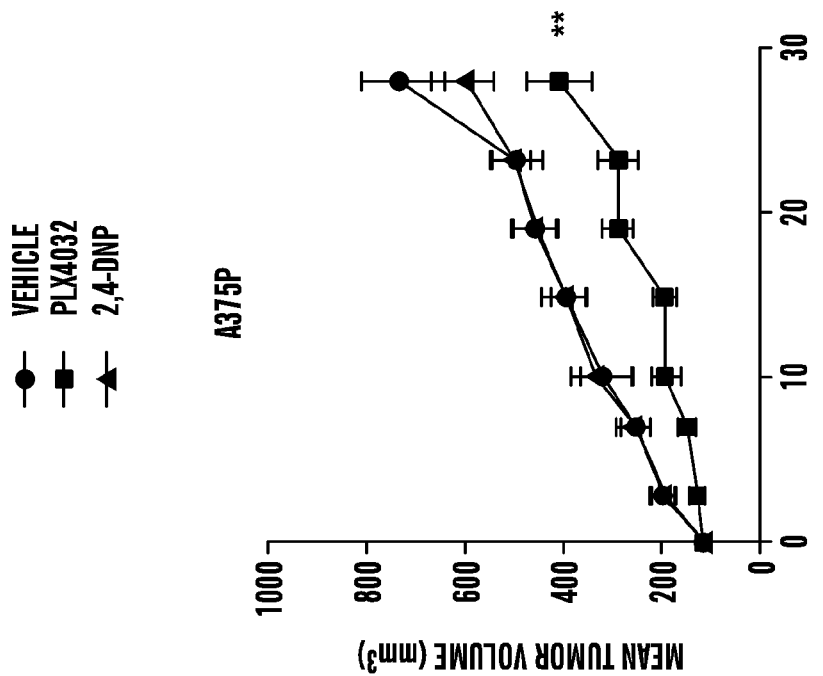
Figure 7F:
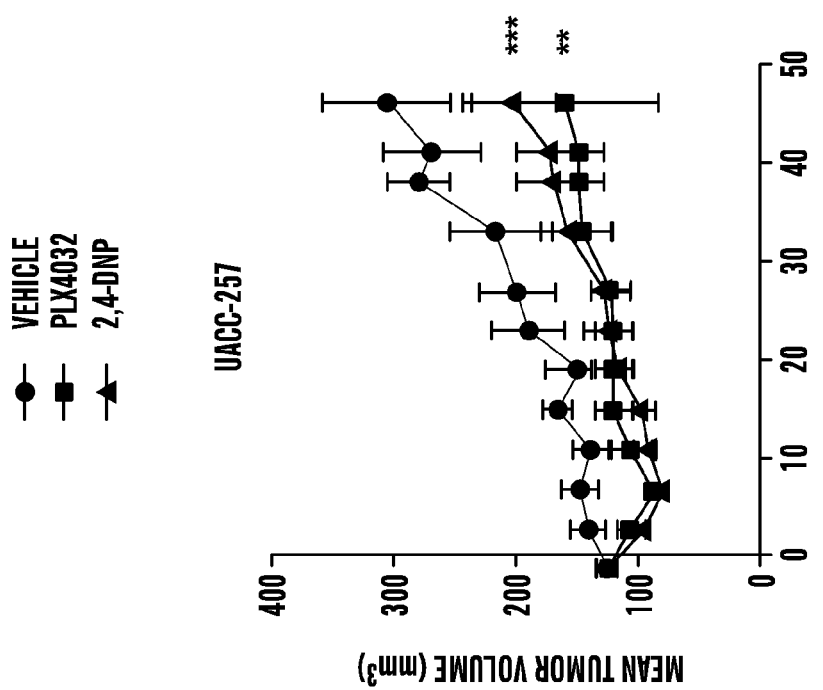
Figure 13:
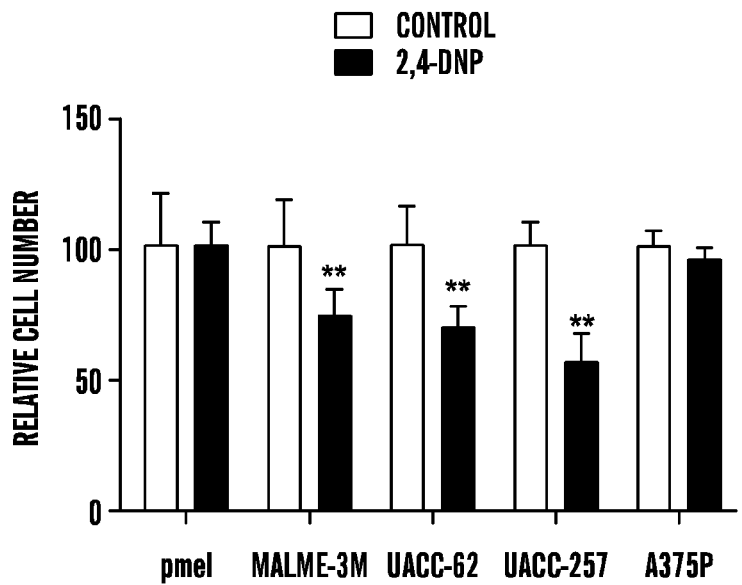
FIG. 13 are histograms showing the number of melanoma cells or primary human melanocytes following treatment with 2,4-DNP (50 µg/mL) for 72 h. **, $p<0.01$ compared to primary melanocytes treated with 2,4-DNP. Error bars represent SEM of at least three independent replicates.

The inventor next investigated whether the oxidative metabolism could be exploited to inhibit the growth of melanoma cells. The sensitivity of melanoma cells were compared to primary melanocytes (FIG. 13A). All melanoma cells were more sensitive to DNP than primary melanocytes, except A375P. Treatment of UACC257 cells, but not A375P cells with DNP led to a decrease in ATP and increases in lactate, consistent with inhibition of OXPHOS (FIGS. 7D and 7E). To validate the effects of mitochondrial inhibitors on tumor growth in vivo, animals bearing tumor xenografts of A375P and UACC257 melanoma cells were treated with DNP. Consistent with the in vitro data, it was found that longitudinal treatment of UACC257 xenografts profoundly inhibited tumor growth, similar to the effects of PLX4032 (FIG. 7F), whereas A375P cells were insensitive to 2,4-DNP (FIG. 7G).

Melanomas Treated with BRAF Inhibitors are Addicted to Oxidative Metabolism

Figures 8A, 8B, 8C:
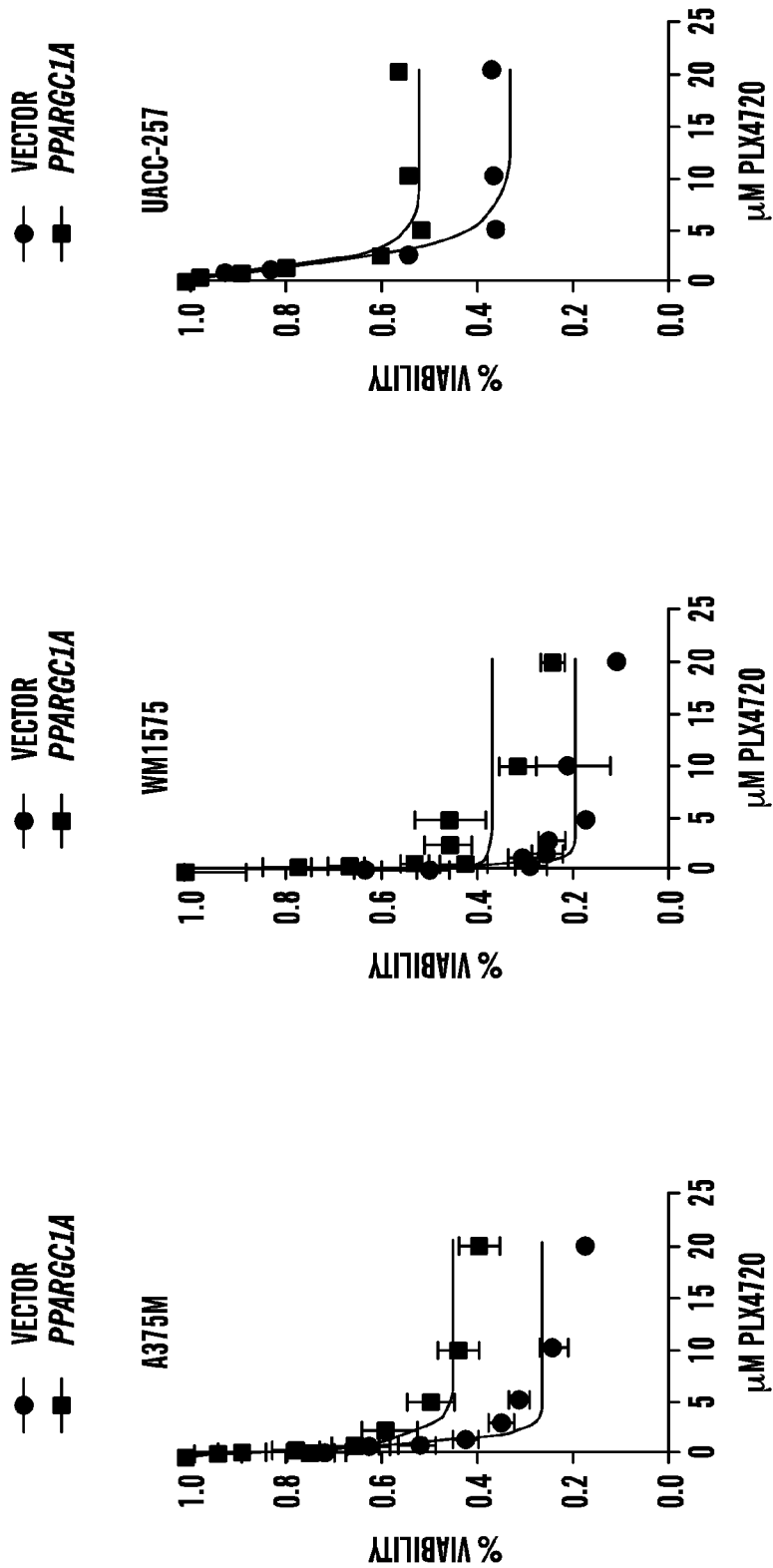
FIGS. 8A-8E show that BRAF inhibitors enhance dependence on mitochondrial metabolism.
Figure 8D:
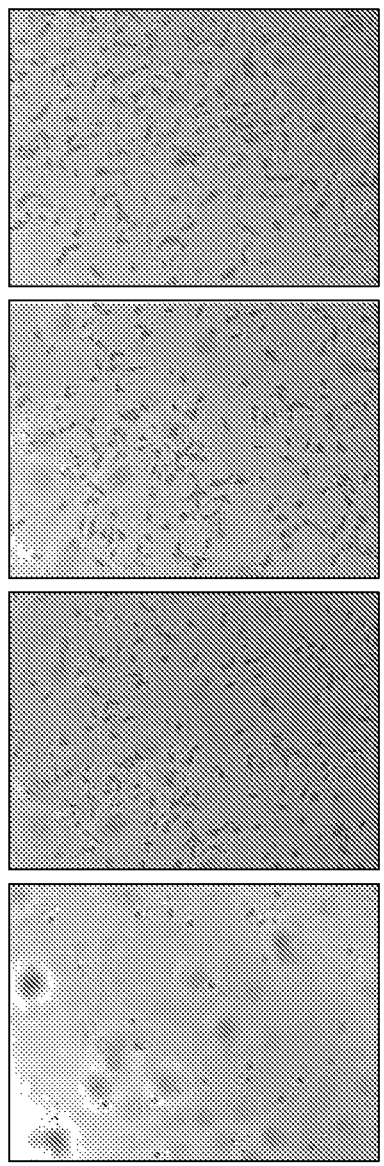
Figure 8E:
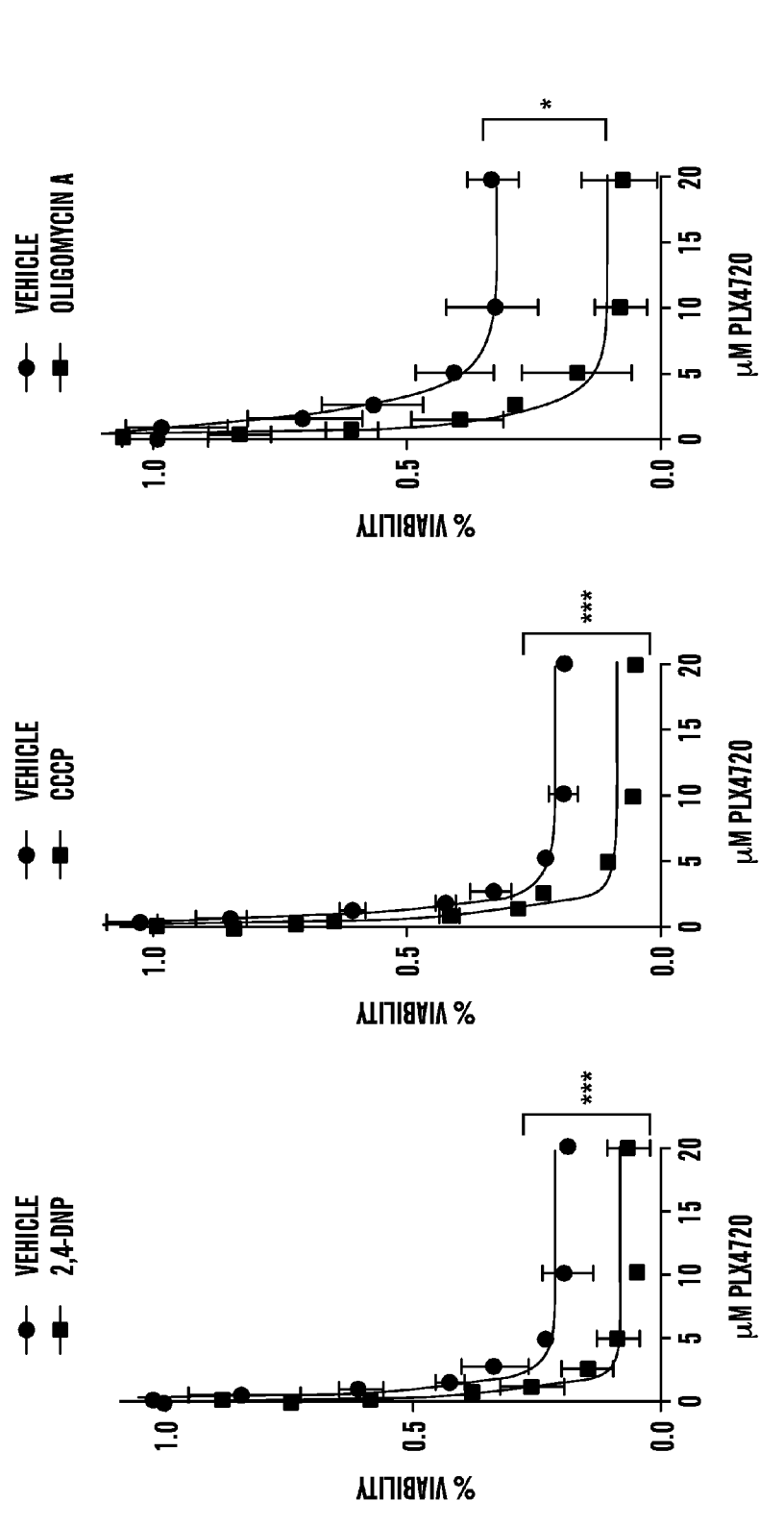
Figure 14A:
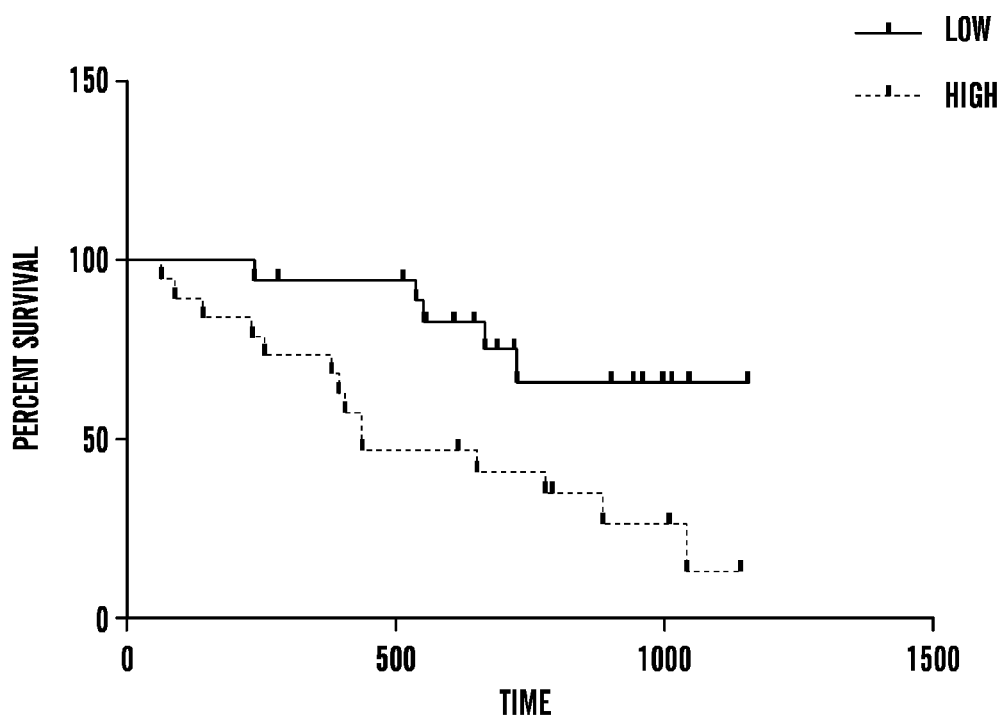
FIG. 14A is a survival graph showing the prognosis of Stage III melanoma patients with high and low levels of PGC1αmRNA derived from GSE19234.
Figure 14C:
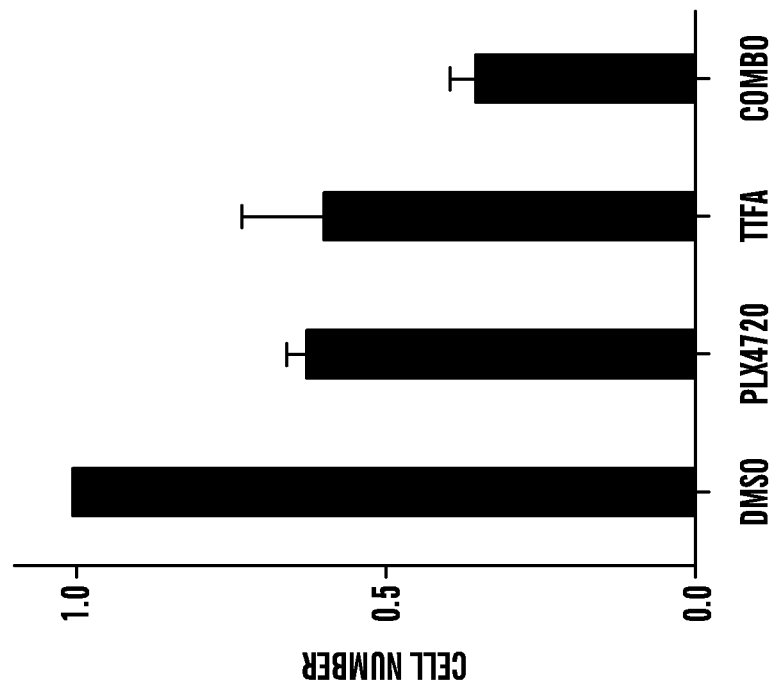
FIG. 14C are histograms showing the effects of TTFA (17504) on cytotoxicity of PLX4720 (1 µM) in the M14 melanoma cell line. Melanoma cell were treated for 24 h with PLX4720 then mitochondrial uncoupler for 48 h, prior to estimation of cell number. Error bars represent SEM of at least three independent replicates.
Figure 14B:
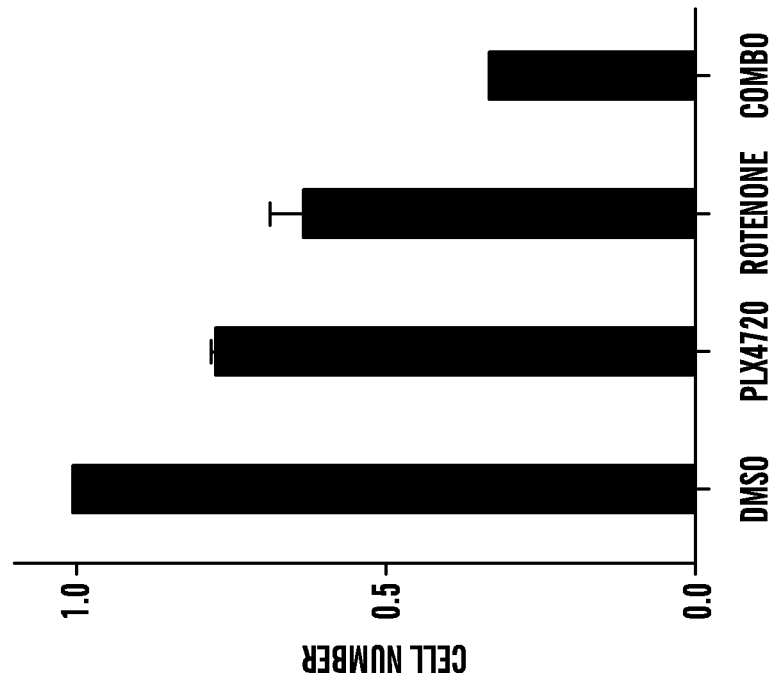
FIG. 14B are histograms showing the effects of Rotenone (75 µM) on cytotoxicity of PLX4720 (1 µM) in the M14 melanoma cell line. Melanoma cell were treated for 24 h with PLX4720 then mitochondrial uncoupler for 48 h, prior to estimation of cell number. Error bars represent SEM of at least three independent replicates.
Figures 15A, 15B:
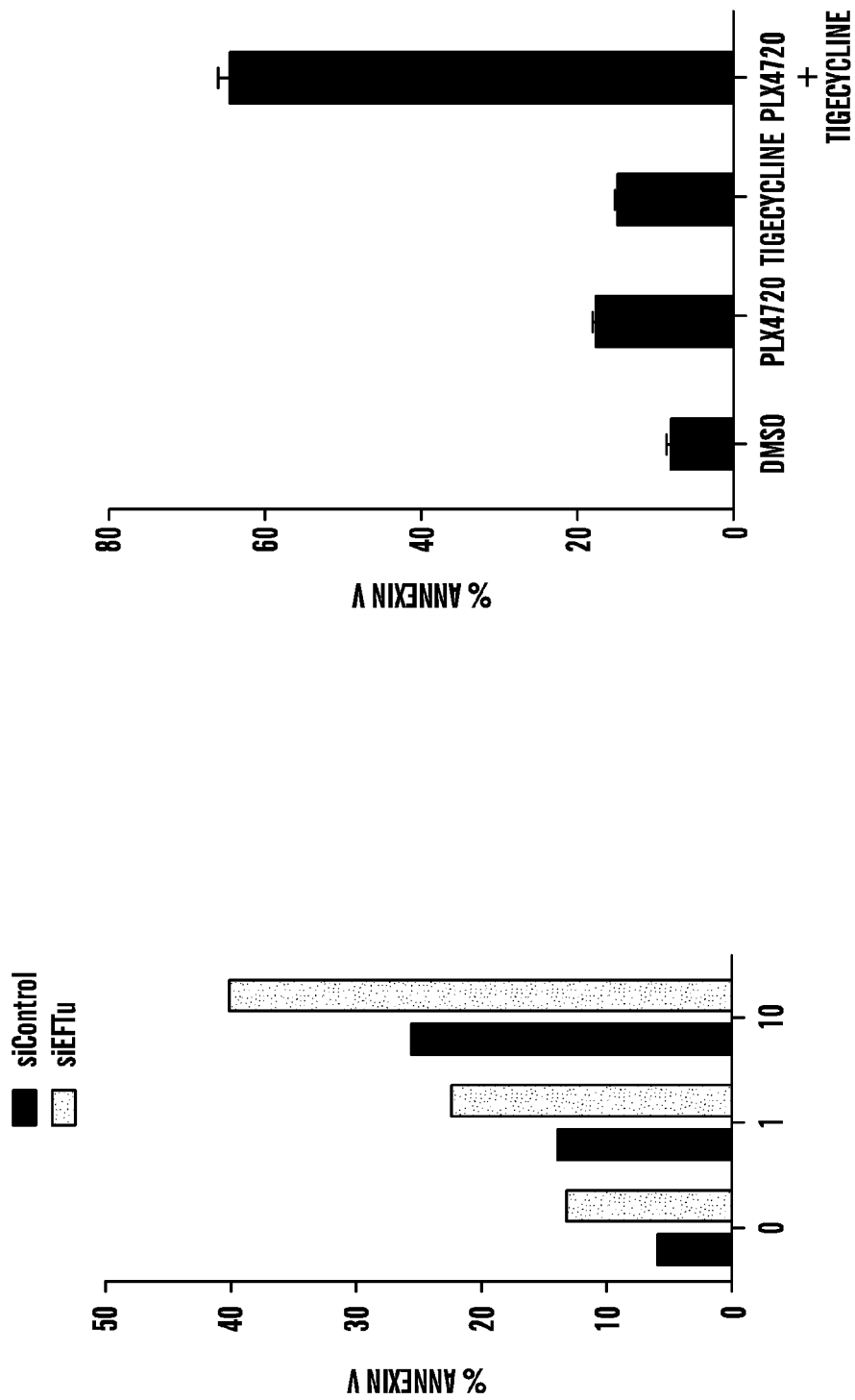
FIGS. 15A and 15B show data that was obtained by using one specific embodiment of the present combinatorial pharmaceutical compositions in practicing one specific embodiment of the present method.

The observations that BRAF and MITF regulate PGC1α expression prompted the inventors to evaluate if oxidative metabolism affected response to BRAF inhibitors. It was observed that high levels of PGC1α were associated with poorer prognosis of patients with Stage III melanoma (FIG. 14A) (Bogunovic et al., 2009). To this end, forced expression of PGC1α protected cells from PLX4720, as demonstrated using three cell lines that expressed low levels of PGC1α (FIG. 8A-8C). As the current data indicate that BRAF regulates PGC1α and oxidative phosphorylation, the effects of inhibitors of oxidative phosphorylation in combination with BRAF inhibitors were evaluated. Melanoma cells treated with 2,4-Dinitrophenol (DNP), or oligomycin A, which inhibit oxidative phosphorylation through different mechanisms additively enhanced the efficacy of PLX4720 in vitro (Combination Index=0.9; FIG. 8E). In addition, the cells were found relatively insensitive to the mitochondrial uncoupler CCCP, but the addition of PLX4720 enhanced the cytotoxicity of this drug (FIG. 8D). Similar data were also observed when rotenone and the complex II inhibitor, TTFA were used (FIGS. 14B and 14C). Together, the data indicate that adaptive induction of oxidative phosphorylation in response to BRAF inhibition limits their efficacy.

Previous studies have suggested a role of BRAF signaling in the regulation of tumor metabolism. Clinically, patients with BRAF mutant melanomas have higher levels of serum lactate consistent with diminished oxidative phosphorylation (Board et al., 2009). In addition, BRAF mutant melanomas have an order of magnitude increased uptake of glucose compared to normal tissues in vivo as assessed by functional imaging (Bollag et al., 2010). However, the mechanism by which BRAF regulates metabolism in melanoma is poorly understood. This study identifies a pathway by which the oncogenic BRAF pathway regulates energy metabolism in melanoma. Our findings show that BRAF activation is associated with diminished oxidative enzymes, diminished mitochondrial number and function and increased production of lactate. This metabolic reprogramming triggered by BRAF(V600E) is accompanied by a suppression of MITF and PGC1α, a major regulator of mitochondrial biogenesis and function.

The inventors identified the melanocyte master regulator MITF as a direct and essential mediator of BRAF-regulated PGC1α transcription. Consistent with the restricted expression of MITF to the melanocyte lineage, the ERK pathway does not appear to regulate PGC1α transcription in BRAF mutant cancers that lack MITF expression (such as colon cancer, see FIG. 2). The MITF-PGC1 connection thus explains the lineage-specific effects of BRAF activation and inhibition.

The references cited herein and throughout the specification are incorporated herein by reference in their entirety.

REFERENCES

Akinc, A., et al. (2008). A combinatorial library of lipid-like materials for delivery of RNAi therapeutics. Nature Biotechnology 26, 561-569.

Arany, Z., et al. (2008). HIF-independent regulation of VEGF and angiogenesis by the transcriptional coactivator PGC-1alpha. Nature 451, 1008-1012.

Baysal, B. E., et al. (2000). Mutations in SDHD, a mitochondrial complex II gene, in hereditary paraganglioma. Science 287, 848-851.

Bensaad, K., et al. (2006). TIGAR, a p53-Inducible Regulator of Glycolysis and Apoptosis. Cell 126, 107-120.

Bertolotto, C., et al. (2011). A SUMOylation-defective MITF germline mutation predisposes to melanoma and renal carcinoma. Nature 480, 94-98.

Bhalla, K., et al. (2011). PGC1 Promotes Tumor Growth by Inducing Gene Expression Programs Supporting Lipogenesis. Cancer Research 71, 6888-6898.

Board, R. E., et al. (2009). Detection of BRAF mutations in the tumour and serum of patients enrolled in the AZD6244 (ARRY-142886) advanced melanoma phase II study. Br J Cancer 101, 1724-1730.

Bogunovic, D., et al. (2009) Immune profile and mitotic index of metastatic melanoma lesions enhance clinical staging in predicting patient survival. Proceedings of the National Academy of Sciences 106, 20429-20434.

Bollag, G., et al. (2010). Clinical efficacy of a RAF inhibitor needs broad target blockade in BRAF-mutant melanoma. Nature 467, 596-599.

Boni, A., et al. (2010). Selective BRAFV600E Inhibition Enhances T-Cell Recognition of Melanoma without Affecting Lymphocyte Function. Cancer Research 70, 5213-5219.

Bonnet, S., et al. (2007). A mitochondria-K+ channel axis is suppressed in cancer and its normalization promotes apoptosis and inhibits cancer growth. Cancer Cell 11, 37-51.

Chapman, P. B., et al. (2011). Improved survival with vemurafenib in melanoma with BRAF V600E mutation. N. Engl. J. Med. 364, 2507-2516.

Chinsomboon, J., et al. (2009). The transcriptional coactivator PGC-1 alpha mediates exercise-induced angiogenesis in skeletal muscle. Proceedings of the National Academy of Sciences 106, 21401-21406.

Colombi, M., et al. (2010). Genome-wide shRNA screen reveals increased mitochondrial dependence upon mTORC2 addiction. Oncogene 30, 1551-1565.

Cui, R., et al. (2007). Central Role of p53 in the Suntan Response and Pathologic Hyperpigmentation. Cell 128, 853-864.

Curtin, J. A., et al. (2005). Distinct sets of genetic alterations in melanoma. N. Engl. J. Med. 353, 2135-2147.

Cutting, W. C., and Tainter, M. (1933). METABOLIC ACTIONS OF DINITROPHENOL. Journal of the American Medical Association 101, 2099-2012.

Dai, M., et al. (2005). Evolving gene/transcript definitions significantly alter the interpretation of GeneChip data. Nucleic Acids Research 33, e175.

Dang, C. V. (2012). Links between metabolism and cancer. Genes & Development 26, 877-890.

Dankort, D., et al. (2009). BrafV600E cooperates with Pten loss to induce metastatic melanoma. Nature Genetics 41, 544-552.

Davies, H., et al. (2002). Mutations of the BRAF gene in human cancer. Nature 417, 949-954.

Dhomen, N., et al. (2009). Oncogenic Braf induces melanocyte senescence and melanoma in mice. Cancer Cell 15, 294-303.

Edsall, G. (1934). Biological actions of dinitrophenol and related compounds: a review. New England Journal of Medicine 211, 385-390.

Eichner, L. J., et al. (2010). miR-378* Mediates Metabolic Shift in Breast Cancer Cells via the PGC-1β/ERRγ Transcriptional Pathway. Cell Metabolism 12, 352-361.

Fantin, V. R., and Leder, P. (2006). Mitochondriotoxic compounds for cancer therapy. Oncogene 25, 4787-4797.

Fantin, V. R., St-Pierre, J., and Leder, P. (2006). Attenuation of LDH-A expression uncovers a link between glycolysis, mitochondrial physiology, and tumor maintenance. Cancer Cell 9, 425-434.

Finck, B. N. (2006). PGC-1 coactivators: inducible regulators of energy metabolism in health and disease. J. Clin. Invest. 116, 615-622.

Flaherty, K. T., et al. (2010). Inhibition of mutated, activated BRAF in metastatic melanoma. N. Engl. J. Med. 363, 809-819.

Garraway, L. A., et al. (2005). Integrative genomic analyses identify MITF as a lineage survival oncogene amplified in malignant melanoma. Nature 436, 117-122.

Girnun, G. D. (2012). The diverse role of the PPARγ coactivator 1 family of transcriptional coactivators in cancer. Seminars in Cell & Developmental Biology 23, 381-388.

Gray-Schopfer, V., et al. (2007). Melanoma biology and new targeted therapy. Nature 445, 851-857.

Greger, J. G., et al. (2012). Combinations of BRAF, MEK, and PI3K/mTOR Inhibitors Overcome Acquired Resistance to the BRAF Inhibitor GSK2118436 Dabrafenib, Mediated by NRAS or MEK Mutations. Molecular Cancer Therapeutics 11, 909-920.

Handschin, C. (2009). The biology of PGC-1a and its therapeutic potential. Trends in Pharmacological Sciences 30, 322-329.

Handschin, C., et al. (2003). An autoregulatory loop controls peroxisome proliferator-activated receptor gamma coactivator 1alpha expression in muscle. Proc. Natl. Acad. Sci. U.S.A. 100, 7111-7116.

Haq, R., and Fisher, D. E. (2011). Biology and Clinical Relevance of the Micropthalmia Family of Transcription Factors in Human Cancer. Journal of Clinical Oncology 29, 3474-3482.

Hemesath, T. J., et al. (1998). MAP kinase links the transcription factor Microphthalmia to c-Kit signaling in melanocytes. Nature 391, 298-301.

Herzig, S., et al. (2001). CREB regulates hepatic gluconeogenesis through the coactivator PGC-1. Nature 413, 179-183.

Hingorani, S. R., et al. (2003). Suppression of BRAF (V599E) in human melanoma abrogates transformation. Cancer Research 63, 5198-5202.

Hoeflich, K. P. (2006). Oncogenic BRAF Is Required for Tumor Growth and Maintenance in Melanoma Models. Cancer Research 66, 999-1006.

Hoek, K. S., et al. (2006). Metastatic potential of melanomas defined by specific gene expression profiles with no BRAF signature. Pigment Cell Research 19, 290-302.

Irizarry, R. A., et al. (2003). Summaries of Affymetrix GeneChip probe level data. Nucleic Acids Research 31, e15.

Johannessen, C. M., et al. (2010). COT drives resistance to RAF inhibition through MAP kinase pathway reactivation. Nature 468, 968-972.

Joseph, E. W., et al. (2010). The RAF inhibitor PLX4032 inhibits ERK signaling and tumor cell proliferation in a V600E BRAF-selective manner. Proceedings of the National Academy of Sciences 107, 14903-14908.

Karasarides, M., et al. (2004). B-RAF is a therapeutic target in melanoma. Oncogene 23, 6292-6298.

Kelly, D. P. (2004). Transcriptional regulatory circuits controlling mitochondrial biogenesis and function. Genes & Development 18, 357-368.

King, A., et al. (2006). Succinate dehydrogenase and fumarate hydratase: linking mitochondrial dysfunction and cancer. Oncogene 25, 4675-4682.

Klimcakova, E., et al. (2012). PGC-1 Promotes the Growth of ErbB2/Neu-Induced Mammary Tumors by Regulating Nutrient Supply. Cancer Research 72, 1538-1546.

Lehman, J. J., et al. (2000). Peroxisome proliferator-activated receptor gamma coactivator-1 promotes cardiac mitochondrial biogenesis. J. Clin. Invest. 106, 847-856.

Leone, T. C., and Kelly, D. P. (2011). Transcriptional Control of Cardiac Fuel Metabolism and Mitochondrial Function. Cold Spring Harb. Symp. Quant. Biol. LXXXVI, 1-7.

Lerin, C., et al. (2006). GCN5 acetyltransferase complex controls glucose metabolism through transcriptional repression of PGC-1alpha. Cell Metabolism 3, 429-438.

Li, J., et al. (2012). YY1 Regulates Melanocyte Development and Function by Cooperating with MITF. PLoS Genet 8, e1002688.

Lin, J., et al. (2005a). Metabolic control through the PGC-1 family of transcription coactivators. Cell Metabolism 1, 361-370.

Lin, J., et al. (2002). Transcriptional co-activator PGC-1 alpha drives the formation of slow-twitch muscle fibres. Nature 418, 797-801.

Lin, J., et al. (2005b). Hyperlipidemic Effects of Dietary Saturated Fats Mediated through PGC-1β Coactivation of SREBP. Cell 120, 261-273.

Lin, W. M., et al. (2008). Modeling Genomic Diversity and Tumor Dependency in Malignant Melanoma. Cancer Research 68, 664-673.

Matoba, S. (2006). p53 Regulates Mitochondrial Respiration. Science 312, 1650-1653.

Miura, S., et al. (2008). Isoform-specific increases in murine skeletal muscle peroxisome proliferator-activated receptor-gamma coactivator-1alpha (PGC-1alpha) mRNA in response to beta2-adrenergic receptor activation and exercise. Endocrinology 149, 4527-4533.

Mootha, V. K., et al. (2003). PGC-1alpha-responsive genes involved in oxidative phosphorylation are coordinately downregulated in human diabetes. Nature Genetics 34, 267-273.

Niemann, S., and Müller, U. (2000). Mutations in SDHC cause autosomal dominant paraganglioma, type 3. Nature Genetics 26, 268-270.

Poulikakos, P. I., and Rosen, N. (2011). Mutant BRAF melanomas--dependence and resistance. Cancer Cell 19, 11-15.

Pratilas, C. A., et al. (2009). (V600E) BRAF is associated with disabled feedback inhibition of RAF-MEK signaling and elevated transcriptional output of the pathway. Proceedings of the National Academy of Sciences 106, 4519-4524.

Prickett, T. D., et al. (2009). Analysis of the tyrosine kinome in melanoma reveals recurrent mutations in ERBB4. Nature Genetics 41, 1127-1132.

Rodgers, J. T., et al. (2005). Nutrient control of glucose homeostasis through a complex of PGC-1alpha and SIRT1. Nature 434, 113-118.

Rowe, G. C., et al. (2010). PGC-1 coactivators in cardiac development and disease. Circ. Res. 107, 825-838.

Sahin, E., et al. (2011). Telomere dysfunction induces metabolic and mitochondrial compromise. Nature 470, 359-365.

Selak, M. A., et al. (2005). Succinate links TCA cycle dysfunction to oncogenesis by inhibiting HIF-alpha prolyl hydroxylase. Cancer Cell 7, 77-85.

Shoag, J., and Arany, Z. (2010). Regulation of hypoxia-inducible genes by PGC-1 alpha. Arterioscler. Thromb. Vasc. Biol. 30, 662-666.

Sosman, J. A., et al. (2012). Survival in BRAF V600-mutant advanced melanoma treated with vemurafenib. N. Engl. J. Med. 366, 707-714.

Stark, M. S., et al. (2012). Frequent somatic mutations in MAP3K5 and MAP3K9 in metastatic melanoma identified by exome sequencing. Nature Genetics 44, 165-169.

Straussman, R., et al. (2012). Tumour micro-environment elicits innate resistance to RAF inhibitors through HGF secretion. Nature 487, 500-504.

Tainter, M., and Wood, D. (1934). A Case of Fatal Dinitrophenol Poisoning. Journal of the American Medical Association 102, 1147-1149.

Tainter, M. L., et al. (1934). Use of Dinitrophenol in Nutritional Disorders: A Critical Survey of Clinical Results. Am J Public Health Nations Health 24, 1045-1053.

Tomlinson, I. P. M., et al. (2002). Germline mutations in FH predispose to dominantly inherited uterine fibroids, skin leiomyomata and papillary renal cell cancer. Nature Genetics 30, 406-410.

Tsai, J., et al. (2008). Discovery of a selective inhibitor of oncogenic B-Raf kinase with potent antimelanoma activity. Proceedings of the National Academy of Sciences 105, 3041-3046.

Uldry, M., et al. (2006). Complementary action of the PGC-1 coactivators in mitochondrial biogenesis and brown fat differentiation. Cell Metabolism 3, 333-341.

Vachtenheim, J., and Borovanský, J. (2010). "Transcription physiology" of pigment formation in melanocytes: central role of MITF. Experimental Dermatology 19, 617-627.

Vander Heiden, M. G., et al. (2009). Understanding the Warburg Effect: The Metabolic Requirements of Cell Proliferation. Science 324, 1029-1033.

Wan, P. T. C., et al. (2004). Mechanism of activation of the RAF-ERK signaling pathway by oncogenic mutations of B-RAF. Cell 116, 855-867.

Wang, X., and Moraes, C. T. (2011). Increases in mitochondrial biogenesis impair carcinogenesis at multiple levels. Molecular Oncology 1-11.

Warburg, O. (1956). On the origin of cancer cells. Science 123, 309-314.

Weinberg, F., et al. (2010). Mitochondrial metabolism and ROS generation are essential for Kras-mediated tumorigenicity. Proceedings of the National Academy of Sciences 107, 8788-8793.

Wellbrock, C. (2005). Elevated expression of MITF counteracts B-RAF-stimulated melanocyte and melanoma cell proliferation. The Journal of Cell Biology 170, 703-708.

Wellbrock, C., et al. (2008). Oncogenic BRAF regulates melanoma proliferation through the lineage specific factor MITF. PLoS ONE 3, e2734.

Wise, D. R., and Thompson, C. B. (2010). Glutamine addiction: a new therapeutic target in cancer. Trends in Biochemical Sciences 35, 427-433.

Wolfrum, C., and Stoffel, M. (2006). Coactivation of Foxa2 through Pgc-1beta promotes liver fatty acid oxidation and triglyceride/VLDL secretion. Cell Metabolism 3, 99-110.

Wu, M., et al. (2000). c-Kit triggers dual phosphorylations, which couple activation and degradation of the essential melanocyte factor Mi. Genes & Development 14, 301-312.

Wu, Z., et al. (1999). Mechanisms controlling mitochondrial biogenesis and respiration through the thermogenic coactivator PGC-1. Cell 98, 115-124.

Yokoyama, S., et al. (2011). A novel recurrent mutation in MITF predisposes to familial and sporadic melanoma. Nature 480, 99-103.

Yoon, J. C., et al. (2001). Control of hepatic gluconeogenesis through the transcriptional coactivator PGC-1. Nature 413, 131-138.

Yun, J., et al. (2009). Glucose Deprivation Contributes to the Development of KRAS Pathway Mutations in Tumor Cells. Science 325, 1555-1559.

TABLE 1A

Signatures enriched in PLX4032 (vemurafenib) treated cell lines (n = 6)

| Name | Size | ES | NES | p-value | FDR, q-value | FWER, p |
|---|---|---|---|---|---|---|
| CITRATE_CYCLE_TCA_CYCLE | 20 | −0.8826642 | −2.0174827 | 0 | 0.026660766 | 0.041 |
| HSA000280_VALINE_LEUCINE_AND_ISOLEUCINE_DEGRADATION | 42 | −0.5626841 | −1.9446014 | 0 | 0.051109686 | 0.148 |
| HSA00020_CITRATE_CYCLE | 25 | −0.63026077 | −1.9404864 | 0 | 0.037463266 | 0.18 |
| OXIDATIVE_PHOSPHORYLATION | 55 | −0.5113584 | −1.8906622 | 0 | 0.052854355 | 0.287 |
| HSA00190_OXIDATIVE_PHOSPHORYLATION | 100 | −0.45311812 | −1.8448951 | 0 | 0.077338466 | 0.463 |
| CAMPTOTHECIN_PROBCELL_UP | 17 | −0.6505533 | −1.8020581 | 0.003590664 | 0.109991774 | 0.644 |
| FLAGELLAR_ASSEMBLY | 19 | −0.6141013 | −1.7995689 | 0 | 0.097633764 | 0.653 |
| PHOTOSYNTHESIS | 20 | −0.618073 | −1.7965853 | 0 | 0.089019455 | 0.664 |
| CANCERDRUGS_PROBCELL_UP | 15 | −0.65977335 | −1.7908636 | 0.003724395 | 0.08555614 | 0.691 |
| PENG_GLUTAMINE_UP | 227 | −0.38959652 | −1.7774848 | 0 | 0.09194197 | 0.764 |
| BRENTANI_TRANSPORT_OF_VESICLES | 23 | −0.6039639 | −1.7719051 | 0.003496504 | 0.0894655 | 0.791 |
| ATP_SYNTHESIS | 19 | −0.6141013 | −1.7496784 | 0.007366483 | 0.105593154 | 0.888 |
| TYPE_III_SECRETION_SYSTEM | 19 | −0.6141013 | −1.7393444 | 0.005190312 | 0.109290734 | 0.891 |
| HSA00640_PROPANOATE_METABOLISM | 29 | −0.54715717 | −1.7328124 | 0 | 0.10970077 | 0.906 |
| VALINE_LEUCINE_AND_ISOLEUCINE_DEGRADATION | 35 | −0.52305466 | −1.7323055 | 0.003514939 | 0.10280863 | 0.906 |

Gene expression sets enriched after treatment of melanoma cell lines (N=6) with vemurafenib. FDR, false-discovery rate; FWER, family-wise error rate; ES, enrichment score; NES, normalized enrichment score; Size refers to gene set size. Details of statistical methods are described in (Mootha et al., 2003).

TABLE 1B

Signatures enriched in MEK inhibitor PD0325901 treated cell lines (n = 5)

| Name | Size | ES | NES | p-value | FDR, q-value | FWER, p |
|---|---|---|---|---|---|---|
| OXIDATIVE_PHOSPHORYLATION | 55 | −0.5313751 | −1.7654682 | 0.019455252 | 1 | 0.506 |
| BRENTANI_CYTOSKELETON | 22 | −0.55218005 | −1.7624917 | 0.015533981 | 0.71292704 | 0.546 |
| TYROSINE_METABOLISM | 28 | −0.56091315 | −1.6678647 | 0.026974952 | 1 | 0.876 |
| TIS7_OVEREXP_DN | 17 | −0.6059337 | −1.6660074 | 0.026690552 | 1 | 0.876 |
| ATP_SYNTHESIS | 19 | −0.58863074 | −1.6509762 | 0.015238095 | 1 | 0.921 |
| TYPE_III_SECRETION_SYSTEM | 19 | −0.58863074 | −1.6509762 | 0.015238095 | 0.6565464 | 0.921 |
| FLAGELLAR_ASSEMBLY | 19 | −0.58863074 | −1.6508762 | 0.015238095 | 0.7341844 | 0.921 |
| PHENYLALANINE_METABOLISM | 21 | −0.56528217 | −1.643656 | 0.02734375 | 0.6949159 | 0.938 |
| SARCOMAS_LEIOMYOSARCOMA_CALP_UP | 15 | −0.5939497 | −1.6180929 | 0.02851711 | 0.7866653 | 0.974 |
| PHOTOSYNTHESIS | 20 | −0.56751925 | −1.595545 | 0.026717557 | 0.8664833 | 0.979 |
| TPA_RESIST_MIDDLE_DN | 107 | −0.39462328 | −1.5864242 | 0 | 0.8576306 | 0.991 |
| HPV31_DN | 44 | −0.51095927 | −1.5835407 | 0.045816734 | 0.808037 | 0.991 |
| LIAN_MYELOID_DIFF_GRANULE | 24 | −0.61149573 | −1.564989 | 0.013944224 | 0.8887548 | 1 |
| VANASSE_BCL2_TARGETS | 76 | −0.39814150 | −1.5503082 | 0.034883723 | 0.9394353 | 1 |
| GLUCONEOGENESIS | 49 | −0.45502195 | −1.547516 | 0.02970297 | 0.9010121 | 1 |

Gene expression sets enriched after treatment of melanoma cell lines (N=5) with MEK inhibitor PD0325901. FDR, false-discovery rate; FWER, family-wise error rate; ES, enrichment score; NES, normalized enrichment score; Size refers to gene set size. Details of statistical methods are described in (Mootha et al., 2003).

TABLE 1C

Signatures enriched in MEK inhibitor PD0325901 non-treated cell lines (n = 7)

| Name | Size | ES | NES | p-value | FDR, q-value | FWER, p |
|---|---|---|---|---|---|---|
| HSA04370_VEGF_SIGNALING_PATHWAY | 66 | −0.49320316 | −1.9460483 | 0 | 0.091074355 | 0.055 |
| LOTEM_LEUKEMIA_UP | 21 | −0.6144097 | −1.9349262 | 0.001945525 | 0.054897256 | 0.064 |
| INSULIN_NIH3T3_UP | 16 | −0.65346473 | −1.926296 | 0 | 0.04251103 | 0.077 |
| HSA00591_LINOLEIC_ACID_METABOLISM | 27 | −0.6261818 | −1.8495042 | 0.003809524 | 0.120073654 | 0.24 |
| HSA00566_ETHER_LIPID_METABOLISM | 27 | −0.60989857 | −1.8358979 | 0.002028398 | 0.1151601 | 0.274 |
| MUNSHI_MM_UP | 65 | −0.45032862 | −1.8108876 | 0.002008032 | 0.14449073 | 0.364 |
| MPRPATHWAY | 22 | −0.5725521 | −1.7240024 | 0 | 0.41018453 | 0.719 |
| HDACI_COLON_CLUSTER9 | 53 | −0.45657748 | −1.7158966 | 0.002 | 0.39486316 | 0.752 |
| HSA04664_FC_EPSILON_RI_SIGNALING_PATHWAY | 73 | −0.45155552 | −1.7113812 | 0.016528925 | 0.37106347 | 0.765 |
| HDACPATHWAY | 29 | −0.524003 | −1.6945506 | 0.003802281 | 0.40905857 | 0.839 |
| ST_GA12_PATHWAY | 21 | −0.55117834 | −1.6834962 | 0.001930502 | 0.42459038 | 0.865 |
| SCHURINGA_STAT5A_DN | 17 | −0.6395701 | −1.6696184 | 0.003960396 | 0.45600265 | 0.899 |

TABLE 1C-continued

Signatures enriched in MEK inhibitor PD0325901 non-treated cell lines (n = 7)

| Name | Size | ES | NES | p-value | FDR, q-value | FWER, p |
|---|---|---|---|---|---|---|
| PASSERINI_OXIDATION | 19 | −0.53578943 | −1.6567032 | 0.014522822 | 0.48720393 | 0.919 |
| HSA00010_GLYCOLYSIS_AND_GLUCONEOGENESIS | 55 | −0.4307168 | −1.6512356 | 0.012295082 | 0.47958305 | 0.928 |
| ERK5PATHWAY | 17 | −0.48306164 | −1.6387306 | 0.0990099 | 0.50899017 | 0.942 |

Gene expression sets enriched after treatment of non-melanomas with PD0325901 (N=7). FDR, false-discovery rate; FWER, family-wise error rate; ES, enrichment score; NES, normalized enrichment score; Size refers to gene set size. Details of statistical methods are described in (Mootha et al., 2003).

TABLE 2

Primer sequences used for quantitative PCR.

| Gene | Forward Primer | Reverse Primer |
|---|---|---|
| ACTB | GTTGTCGACGACGAGCG | GCACAGAGCCTCGCCTT |
| ATP5D | CAGGTCCAACATGTCCAGC | ACGGCACCACCTCCAAATAC |
| ATP5G1 | GCCTGATTAGACCCCTGGTA | GGCTAAAGCTGGGAGACTGA |
| NDUFA8 | CTCCTTGTTGGGCTTATCACA | GCCCACTCTAGAGGAGCTGA |
| ATP5B | CAAGTCATCAGCAGGCACAT | TGGCCACTGACATGGGTACT |
| PPARGC1A | CTGCTAGCAAGTTTGCCTCA | AGTGGTGCAGTGACCAATCA |
| SDHB | AAGCATCCAATACCATGGGG | TCTATCGATGGGACCCAGAC |
| SLC25A4 | CCCTGCTCCTTAGGGATTCT | AGAGGGTCAAACTGCTGCTG |
| PPRC1 | TGACAAAGCCAGAATCACCC | GTGGTTGGGGAAGTCGAAG |
| CAT | ACGGGGCCCTACTGTAATAA | AGATGCAGCACTGGAAGGAG |
| SOD2 | TAGGGCTGAGGTTTGTCCAG | GGAGAAGTACCAGGAGGCGT |
| M-MITF | CCGTCTCTCACTGGATTGGT | TACTTGGTGGGGTTTTCGAG |
| TFEB | GGGAGTTGGATGATGTCATTG | GGCATCTGCATTTCAGGATTG |
| TFE3 | GCAGGCGATTCAACATTAACG | ATAATCCACAGAGGCCTTCAG |
| PPARGC1B | CAGACAGAACGCCAAGCATC | TCGCACTCCTCAATCTCACC |
| TRPM1 | CAAAGATACATTCCCGTTTGC | GCTGAAAGAGCCTGAGCTGT |
| PKM1 | CTGAAGGCAGTGATGTGGCC | CTCCGTCAGAACTATCAAAGC |

Primers Sequences Used for Mutagenesis of PPARGC1A Promoter

| Mutation | Forward Primer | Reverse Primer |
|---|---|---|
| E-box 1 | CCTACTTTTTAATAGCTT TGTGAAGTGACTGGGGAC TGTAGTAAG | CTTACTACAGTCCCCAGTCACTT CACAAAGCTATTAAAAAGTAGG |
| E-box 2 | TCTCATGAAAATGTATCA CTTCAGGAGCGCTTGCTT CAGTTC | GAACTGAAGCAAGCGCTCCTGAA GTGATACATTTTCATGAGA |

Primer Sequences Used for Chromatin Immunoprecipitation

| Gene | Forward Primer | Reverse Primer |
|---|---|---|
| PPARGC1A | GACGCCAGTCAAGCTTTTTC | CGTCACGAGTTAGAGCAGCA |
| TYR | GTGGGATACGAGCCAATTCG AAAG | GTGGGATACGAGCCAATTCG AAAG |
| PPARGC1A (alt) | TCCCGGGATAAAGTGTCATC | TCGAGGGAGCTCTCTGACAT |
| GAPDH | ATGGTTGCCACTGGGGATCT | TGCCAAAGCCTAGGGGAAGA |

Lentiviral shRNAs in pLKO.Puro

| Gene | Target Sequence | TRC clone name |
|---|---|---|
| PKM | GCTGTGGCTCTAGACACTAAA | NM_182471.1-566s21c1 (#566) |
|  | CGCAAGCTGTTTGAAGAACTT | NM_182471.1-1415s1c1 (#1415) |

What is claimed:

1. A method for treating melanoma in a subject in need thereof, the method comprising administering to the subject a therapeutically effective amount of a composition consisting of:
   (a) at least one inhibitor of B-Raf consisting of vemurafenib, GDC-0879, PLX-4720, Sorafenib Tosylate, Regorafenib, RAF265 and derivatives, NVP-BHG712, AZ628, ZM 336372, SB590885, dabrafenib, and LGX818; and
   (b) at least one mitochondrial inhibitor consisting of oligomycin, malonate, oxaloacetate, barbiturates, rotenone, antimycin-A, arsenate, NV-128, ME-344, TTFA, rotenone, 2,4-Dinitrophenol (DNP), and oligomycin A in a pharmaceutically acceptable carrier,
   wherein the melanoma comprises at least one mutation in the B-RAF gene therein.

2. The method of claim 1, wherein the inhibitor of B-Raf is PLX-4720 and the mitochondrial inhibitor is DNP.

3. The method of claim 1, further comprising selecting a subject who has been diagnosed with melanoma.

4. The method of claim 1, wherein the at least one B-RAF gene mutation is a substitution of valine at the 600 amino acid residue of the encoded B-Raf polypeptide.

5. The method of claim 4, wherein the substitution is selected from the group consisting of V600E, V600D, V600K and V600R.

* * * * *

SEQUENCE LISTING

```
<160> NUMBER OF SEQ ID NOS: 61

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 1
gttgtcgacg acgagcg                                                    17
```

<210> SEQ ID NO 2
<211> LENGTH: 17
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 2
gcacagagcc tcgcctt                                                    17

<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 3
caggtccaac atgtccagc                                                  19

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 4
acggcaccac ctccaaatac                                                 20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 5
gcctgattag acccctggta                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 6
ggctaaagct gggagactga                                                 20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 7
ctccttgttg ggcttatcac a                                               21

```
<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 8
gcccactcta gaggagctga                                                20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 9
caagtcatca gcaggcacat                                                20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 10
tggccactga catgggtact                                                20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 11
ctgctagcaa gtttgcctca                                                20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 12
agtggtgcag tgaccaatca                                                20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 13
aagcatccaa taccatgggg                                                20

<210> SEQ ID NO 14
```

```
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 14
tctatcgatg ggacccagac                                                  20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 15
ccctgctcct tagggattct                                                  20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 16
agagggtcaa actgctgctg                                                  20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 17
tgacaaagcc agaatcaccc                                                  20

<210> SEQ ID NO 18
<211> LENGTH: 19
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 18
gtggttgggg aagtcgaag                                                   19

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 19
acggggccct actgtaataa                                                  20

<210> SEQ ID NO 20
<211> LENGTH: 20
```

```
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 20
agatgcagca ctggaaggag                                                    20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 21
tagggctgag gtttgtccag                                                    20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 22
ggagaagtac caggaggcgt                                                    20

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 23
ccgtctctca ctggattggt                                                    20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 24
tacttggtgg ggttttcgag                                                    20

<210> SEQ ID NO 25
<211> LENGTH: 21
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 25
gggagttgga tgatgtcatt g                                                  21

<210> SEQ ID NO 26
<211> LENGTH: 21
<212> TYPE: DNA
```

```
<213> ORGANISM: Artificial Sequence
<220> FEATURE:
<223> OTHER INFORMATION: Description of Artificial Sequence: Synthetic
      reverse primer

<400> SEQUENCE: 26
ggcatctgca tttcaggatt g                                                 21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 27
gcaggcgatt caacattaac g                                                 21

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 28
ataatccaca gaggccttca g                                                 21

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 29
cagacagaac gccaagcatc                                                   20

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 30
tcgcactcct caatctcacc                                                   20

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 31
caaagataca ttcccgtttg c                                                 21

<210> SEQ ID NO 32
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      reverse primer

<400> SEQUENCE: 32
gctgaaagag cctgagctgt                                                   20

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 33
ctgaaggcag tgatgtggcc                                                   20

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 34
ctccgtcaga actatcaaag c                                                 21

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 35 cctactttt aatagctttg tgaagtgact ggggactgta gtaag                        45

<210> SEQ ID NO 36
<211> LENGTH: 45
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 36
cttactacag tccccagtca cttcacaaag ctattaaaaa gtagg                       45

<210> SEQ ID NO 37
<211> LENGTH: 42
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 37
tctcatgaaa atgtatcact tcaggagcgc ttgcttcagt tc                          42

<210> SEQ ID NO 38
<211> LENGTH: 42
<212> TYPE: DNA
<213> ORGANISM: Artificial Sequence
<220> FEATURE:
```

```
<223> OTHER INFORMATION: Description of Artificial Sequence: Synthetic
      reverse primer

<400> SEQUENCE: 38
gaactgaagc aagcgctcct gaagtgatac attttcatga ga                              42

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 39
gacgccagtc aagcttttc                                                         20

<210> SEQ ID NO 40
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 40
cgtcacgagt tagagcagca                                                        20

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 41
gtgggatacg agccaattcg aaag                                                   24

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 42
gtgggatacg agccaattcg aaag                                                   24

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 43
tcccgggata aagtgtcatc                                                        20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthetic
``` reverse primer

<400> SEQUENCE: 44
tcgagggagc tctctgacat                                               20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      forward primer

<400> SEQUENCE: 45
atggttgcca ctgggatct                                                20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthetic
      reverse primer

<400> SEQUENCE: 46
tgccaaagcc tagggaaga                                                20

<210> SEQ ID NO 47
<211> LENGTH: 21
<212> TYPE: DNA
<213> ORGANISM: Artificial Sequence
<220> FEATURE:
<223> OTHER INFORMATION: Description of Artificial Sequence: Synthetic
      PKM target sequence

<400> SEQUENCE: 47
gctgtggctc tagacactaa a                                             21

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthetic
      PKM target sequence

<400> SEQUENCE: 48
cgcaagctgt ttgaagaact t                                             21

<210> SEQ ID NO 49
<211> LENGTH: 70
<212> TYPE: DNA
<213> ORGANISM: Unknown
<220> FEATURE:
<223> OTHER INFORMATION: Description of Unknown:
      PGC1alpha oligonucleotide

<400> SEQUENCE: 49
tgtcatgtga ctggggactg tagtaagaca ggtgccttca gttcactctc agtaaggggc   60
tggttgcctg                                                          70

<210> SEQ ID NO 50
<211> LENGTH: 19
<212> TYPE: DNA
<213> ORGANISM: Mus sp.

```
<400> SEQUENCE: 50
tgtatcacat gaggagcgc                                         19

<210> SEQ ID NO 51
<211> LENGTH: 46
<212> TYPE: DNA
<213> ORGANISM: Mus sp.

<400> SEQUENCE: 51
agcctacttt ttaatagctt tgtcatgtga ctggggactg tagtaa            46

<210> SEQ ID NO 52
<211> LENGTH: 19
<212> TYPE: DNA
<213> ORGANISM: Rattus sp.

<400> SEQUENCE: 52
cgtatcacat gaggagctt                                         19

<210> SEQ ID NO 53
<211> LENGTH: 46
<212> TYPE: DNA
<213> ORGANISM: Rattus sp.

<400> SEQUENCE: 53
agcctacttt ttaatagctt tgtcatgtga ctggggactg tagtaa            46

<210> SEQ ID NO 54
<211> LENGTH: 19
<212> TYPE: DNA
<213> ORGANISM: Homo sapiens

<400> SEQUENCE: 54
tgcatcatgt gataagctc                                         19

<210> SEQ ID NO 55
<211> LENGTH: 46
<212> TYPE: DNA
<213> ORGANISM: Homo sapiens

<400> SEQUENCE: 55
agcctacttt ttaatagctt tgtcatgtga ctggggactg tagtaa            46

<210> SEQ ID NO 56
<211> LENGTH: 19
<212> TYPE: DNA
<213> ORGANISM: Pongo sp.

<400> SEQUENCE: 56
tgtatcatgt gataagcgc                                         19

<210> SEQ ID NO 57
<211> LENGTH: 46
<212> TYPE: DNA
<213> ORGANISM: Pongo sp.

<400> SEQUENCE: 57
agcctacttt ttaatagctt tgtcatgtga ctggggactg tagtaa            46

<210> SEQ ID NO 58
<211> LENGTH: 19
<212> TYPE: DNA
<213> ORGANISM: Canis lupus
```

```
<400> SEQUENCE: 58
tgtatcatgt gataagcgc                                              19

<210> SEQ ID NO 59
<211> LENGTH: 46
<212> TYPE: DNA
<213> ORGANISM: Canis lupus

<400> SEQUENCE: 59
agcctacttt ttaatagctt tgtcatgtga ctgggaactg tagtaa                46

<210> SEQ ID NO 60
<211> LENGTH: 19
<212> TYPE: DNA
<213> ORGANISM: Equus caballus

<400> SEQUENCE: 60
tgtatcatgt gataagcgc                                              19

<210> SEQ ID NO 61
<211> LENGTH: 46
<212> TYPE: DNA
<213> ORGANISM: Equus caballus

<400> SEQUENCE: 61
agcctacttt ttaatagctt tgtcatgtga ctggggactg tagtaa                46
```